US007326701B2

(12) United States Patent
Iino et al.

(10) Patent No.: US 7,326,701 B2
(45) Date of Patent: *Feb. 5, 2008

(54) LACTAM COMPOUNDS AND PHARMACEUTICAL USE THEREOF

(75) Inventors: Yukio Iino, Kawasaki (JP); Takao Ikenoue, Kawasaki (JP); Nobuo Kondo, Kawasaki (JP); Hiroyuki Matsueda, Kawasaki (JP); Toshihiro Hatanaka, Kawasaki (JP); Ryusuke Hirama, Kawasaki (JP); Yoko Masuzawa, Kawasaki (JP); Fumio Ohta, Kawasaki (JP); Akiyo Yamazaki, Cambridge, MA (US); Seiji Niwa, Kawasaki (JP); Takashi Yamamoto, Tucson, AZ (US)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/398,675

(22) Filed: Apr. 6, 2006

(65) Prior Publication Data

US 2006/0189597 A1 Aug. 24, 2006

Related U.S. Application Data

(63) Continuation of application No. 10/449,774, filed on Jun. 2, 2003, now Pat. No. 7,153,850, which is a continuation-in-part of application No. PCT/JP01/10435, filed on Nov. 29, 2001.

(30) Foreign Application Priority Data

Dec. 1, 2000 (JP) .............................. 2000-367175

(51) Int. Cl.
*C07D 487/04* (2006.01)
*A61K 31/5517* (2006.01)
*A61P 3/10* (2006.01)

(52) U.S. Cl. ...................... 514/220; 540/557
(58) Field of Classification Search ............... 540/557; 514/220
See application file for complete search history.

(56) References Cited

U.S. PATENT DOCUMENTS

2004/0048847 A1 3/2004 Iino et al.

2005/0272641 A1 12/2005 Ikenoue et al.
2006/0189597 A1 8/2006 Iino et al.

FOREIGN PATENT DOCUMENTS

HU       P0003394     8/2001
JP       11-171776    6/1999
WO       99/06403     2/1999

OTHER PUBLICATIONS

U.S. Appl. No. 11/486,213, filed Jul. 14, 2006, Hirama et al.
U.S. Appl. No. 11/398,675, filed Apr. 6, 2006, Iino et al.
U.S. Appl. No. 11/414,499, filed May 1, 2006, Hirama et al.
Sorokina, et al., "Synthesis and Pharmacological Study of Derivatives of Pyrrolo[3,4-B]Benzo[1,5]Diazepine", Pharmaceutical Chemistry Journal, vol. 25, No. 11, 1991, pp. 768-770.
Matsuo, et al., "Synthesis and Reaction of Dihydrofuro[3,4-B][1,5]Benzodiazepinones and Dihydropyrrolo[3,4-B][1,5]Benzodiazepinones", Journal of the Pharmaceutical Society of Japan, vol. 106, No. 8, 1986, pp. 715-720.
Matsuo, et al., "Syntheses of the Novel Furo[3,4-B][1,5]Benzodiazepinone and Pyrrolo[3,4-B][1,5] Benzodiazepinone Systems", Chem. Pharm. Bull., vol. 32, No. 9, pp. 3724-3729, 1984.
Augustin, et al., "A Simple Synthesis of Some New 2-Aryl-Substituted 2,5-Dihydro-1-H-1,5-Benzodiazepine-and 2,5-Dihydro-1,5-Benzothiaepin-3,4-Dicarboxylic N-Arylimides", Communications, 1987, pp. 937-938.
Matsuo, et al., "10-Aryl-3,3-Dimethyl-2,3,4,10-Tetrahydro-1H-Pyrrolo[3,4-C] [,5]Benzothiazepin-1-One", Journal of the Pharmaceutical Society of Japan, vol. 104, No. 9, 1984, pp. 1004-1008.
Schmidt, et al., "Ring Construction Using 3-(Arylmethylene)-2,4(3H,5H)-Furandione: Synthesis of Pyrazolones and Furo[3,4-C][1,5]Benzothiazepinones", J. Org. Chem., vol. 48, No. 23, 1983, pp. 4367-4370.
K. Matsuo, et al., "Synthesis and Reaction of 10-Aryl-3,4,9,10-Tetrahydro-1H-Thieno-[4,3-B][1,5]Benzodiazepin-1-Ones", Chemistry Express, vol. 6, No. 7, 1991, pp. 495-498.

*Primary Examiner*—Bruck Kifle
(74) *Attorney, Agent, or Firm*—Oblon, Spivak, McClelland, Maier & Neustadt, P.C.

(57) ABSTRACT

An agent for increasing the sugar-transporting capacity and an agent for preventing and/or treating diabetes, diabetic peripheral neuropathy, diabetic nephropathy, diabetic retinopathy, diabetic macroangiopathy, impaired glucose tolerance or adiposis, which contains a lactam compound or a pharmaceutically acceptable salt thereof as the active ingredient.

36 Claims, No Drawings

LACTAM COMPOUNDS AND PHARMACEUTICAL USE THEREOF

CROSS-REFERENCE TO RELATED APPLICATIONS

The present application is a continuation of U.S. Ser. No. 10/449,774, filed on Jun. 2, 2003, now U.S. Pat. No. 7,153,850 which is a continuation-in-part of PCT/JP01/10435, filed on Nov. 29, 2001, which claims priority to JP 2000-367175, filed on Dec. 1, 2000.

BACKGROUND OF THE INVENTION

The present invention relates to lactam compounds and a therapeutic agent for diabetes which contains the compound(s) as the active ingredient.

The medicinal treatment for type II diabetes is employed when a sufficient improvement of a patient cannot be attained by dietetic treatment or kinetotherapy, and there have been developed pharmaceutical preparations containing insulin that is an endogenous hormone for controlling the hypoglycemic function and also peroral hypoglycemic agents having an effect of accelerating insulin secretion or improving peripheral insulin resistance. At present, the main medicinal treatment for type II diabetes comprises using a peroral hypoglycemic agent for strictly controlling the blood sugar level. However, when insulin-like effect sufficient for controlling the blood sugar cannot be obtained, the insulin therapy is mainly employed. On the other hand, the insulin therapy is the only treatment for patients with type I diabetes because they have lost the insulin secretion capacity.

Although the insulin therapy is thus an important treatment method, use of injection causes problems that the treatment technique is complicated and that the patient must be trained. Under these conditions, an improvement in the administration method is eagerly demanded from the viewpoint of the compliance. Recently, it was tried to develop methods for administering insulin in the form of non-injection preparations instead of the insulin injection. However, those methods have not been practically employed because of a low absorption efficiency or unstable absorption.

It is one of the important hypoglycemic functions of insulin that it increases the sugar-transporting capacity of peripheral cells to incorporate the sugar in the blood into the cells and, as a result, the blood sugar level is lowered. If a new oral medicine capable of lowering the blood sugar level by increasing the sugar-transporting capacity of peripheral cells is found, it would became the therapy in favor of the patients. However, such a medicine has not yet been developed.

On the other hand, as for the lactam compound, Khim.-Farm. Zh., 25 (11), (1991) and Pharmaceutical Chemical Journal. 25 (11), 768 (1991) disclose compounds of general formula (I) given below, wherein B represents a benzene ring, —X— and —Y— each represent —NH—Z—, represents —CH$_2$—, —W— represents —NH— and -A(R$^2$)(R$^3$)(R$^4$) represents a phenyl group, 4-bromophenyl group, 4-hydroxyphenyl group, 4-methoxyphenyl group, 2-hydroxyphenyl group, 3,4-dimethoxyphenyl group or 3-methoxy-4-hydroxyphenyl group. It is described therein that those compounds have no anxiolytic effect, antispasmodic effect or cardiotonic effect.

Journal of the Pharmaceutical Society of Japan, 715-20 (1986) and Chem. Pharm. Bull., 3724-9 (1984) disclose compounds of general formula (I) given below, wherein B represents a benzene ring, —X— represents —NH—, —Z—represents —CR$^6$R$^7$—, —W— represents —NH— and R$^6$ and R$^7$ each represent a methyl group. It is described therein that those compounds have a weak analgesic effect.

Synthesis, 937-8 (1987) discloses a compound of general formula (I) given below, wherein B represents a benzene ring, —X— represents —NH—, —Z— represents —CO—, —W— represents —NR$^1$— and R$^1$ represents p-tolyl group. However, the activity of this compound is not described therein.

Journal of the Pharmaceutical Society of Japan, 1004-8 (1984) discloses compounds of general formula (I) given below, wherein B represents a benzene ring, —X— represents —NH—, —Y— represents —S—, —Z— represents —CR$^6$R$^7$—, W represents —NH— and R$^6$ and R$^7$ each represent a methyl group. It is described therein that those compounds have a weak sterilizing effect.

Journal of Organic Chemistry, 4367-70 (1983) also discloses compounds of general formula (I) given below, wherein B represents a benzene ring, —X— represents —NH—, —Y— represents —S—, —Z— represents —CH$_2$— and —W— represents —O—. However, the activity of this compound is not described therein.

DISCLOSURE OF THE INVENTION

An object of the present invention is to provide newly developed therapeutic agent for diabetes having a high medicinal effect and slight side effects.

Another object of the present invention is to provide an agent for increasing the sugar-transporting capacity.

A still another object of the present invention is to provide a hypoglycemic agent.

A still another object of the present invention is to provide an agent for preventing and/or treating diabetes, diabetic peripheral neuropathy, diabetic nephropathy, diabetic retinopathy, diabetic macroangiopathy, impaired glucose tolerance or adiposis.

A further object of the present invention is to provide new lactam compounds.

Another object of the present invention is to provide a pharmaceutical composition.

After intensive investigations made for the purpose of finding compounds having an effect of increasing the sugar-transporting capacity and useful for treating diabetes, the present inventors have found compounds of the following general formula (I). The present invention has been completed on the basis of this finding.

Namely, the present invention provides an agent for increasing the sugar-transporting capacity, which contains a lactam compound(s) of the following general formula (I) or a pharmaceutically acceptable salt(s) thereof as the active ingredient:

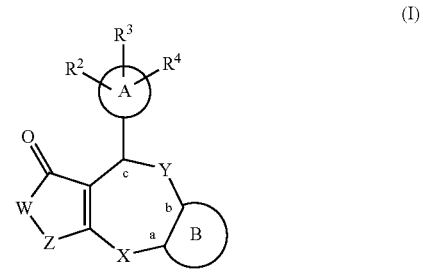

(I)

wherein A represents an aromatic ring, a heterocyclic ring or an aliphatic ring; R$^2$, R$^3$ and R$^4$ may be the same or different from one another and independently represent a hydrogen atom, a halogen atom, a hydroxyl group, an alkyl group, a mercapto group, an alkoxyl group, an alkylthio group, an alkylsulfonyl group, an acyl group, an acyloxyl group, an amino group, an alkylamino group, a carboxyl group, an alkoxycarbonyl group, a carbamoyl group, a nitro group, a cyano group, a trifluoromethyl group, an alkenyl group which may have a substituent(s), an alkynyl group which may have a substituent(s), an aryl group which may have a substituent(s), a heteroaryl group which may have a substituent(s), a benzyloxyl group which may have a substituent(s), an aryloxyl group which may have a substituent(s), a heteroaryloxyl group which may have a substituent(s), an arylamino group which may have a substituent(s), an arylvinyl group which may have a substituent(s) or an arylethynyl group which may have a substituent(s); B represents an aromatic ring which may have a substituent(s), a heterocyclic ring which may have a substituent(s) or an aliphatic ring which may have a substituent(s); —X—, —Y— and —Z— may be the same or different from one another and they independently represent —O—, —NH—, —NR$^5$—, —S—, —SO—, —SO$_2$—, —CH$_2$—, —CR$^6$R$^7$— or —CO— wherein R$^5$ represents a lower alkyl group which may have a substituent(s), an acyl group which may have a substituent(s), an alkoxycarbonyl group which may have a substituent(s), a carbamoyl group which may have a substituent(s) or sulfonyl group which may have a substituent(s), R$^6$ and R$^7$ may be the same or different from each other and they independently represent a hydrogen atom, a halogen atom, a hydroxyl group, an alkyl group which may have a substituent(s), a mercapto group, an alkoxyl group, an alkylthio group, an alkylsulfonyl group, an acyl group, an acyloxyl group, an amino group, an alkylamino group, a carboxyl group, an alkoxycarbonyl group, a carbamoyl group, a nitro group, a cyano group or trifluoromethyl group; —W— represents —NR$^1$—, —O— or —CR$^8$R$^9$— wherein R$^1$ represents a hydrogen atom, a lower alkyl group which may have a substituent(s) or an aryl group which may have a substituent(s), and R$^8$ and R$^9$ may be the same or different from each other and they independently represent a hydrogen atom, a halogen atom, a hydroxyl group, an alkyl group, an aryl group, a mercapto group, an alkoxyl group, an alkylthio group, an alkylsulfonyl group, an acyl group, an acyloxyl group, an amino group, an alkylamino group, a carboxyl group, an alkoxycarbonyl group, a carbamoyl group, a nitro group, a cyano group or trifluoromethyl group; and a, b and c each represent the position of carbon atom, with the proviso that:

(i) the substituent(s) is selected from the group consisting of halogen atoms, hydroxyl group, alkyl groups, aryl groups, mercapto group, alkoxyl groups, alkylthio groups, alkylsulfonyl groups, acyl groups, acyloxyl groups, amino group, alkylamino groups, carboxyl group, alkoxycarbonyl groups, carbamoyl groups, nitro group, cyano group, trifluoromethyl group, aryl groups and heteroaryl groups.

The present invention also provides new lactam compounds of the above general formula (1) wherein:

(ii) when B is a benzene ring, —X— and —Y— are each —NH—, —Z— is —CH$_2$— and —W— is —NH—, —A(R$^2$)(R$^3$)(R$^4$) cannot be a phenyl group, 4-bromophenyl group, 4-hydroxyphenyl group, 4-methoxyphenyl group, 2-hydroxyphenyl group, 3,4-dimethoxyphenyl group or 3-methoxy-4-hydroxyphenyl group, (iii) when B is a benzene ring, —X— is —NH—, —Z— is —CR$^6$R$^7$— and —W— is —NH—, both R$^6$ and R$^7$ cannot be methyl group, (iv) when B is a benzene ring, —X— is —NH—, —Z— is —CO— and —W— is —NR$^1$—, R$^1$ cannot be a p-tolyl group, (v) when B is a benzene ring, —X— is —NH—, —Y— is —S—, —Z— is —CR$^6$R$^7$— and —W— is —NH—, both R$^6$ and R$^7$ cannot be methyl group, and (vi) when B is a benzene ring, —X— is —NH—, —Y— is —S— and —Z— is —CH$_2$—, —W— cannot be —O— or pharmaceutically acceptable salts thereof.

The present invention also provides a hypoglycemic agent and also an agent for preventing and/or treating diabetes, diabetic peripheral neuropathy, diabetic nephropathy, diabetic retinopathy, diabetic macroangiopathy, impaired glucose tolerance or adiposis, which contains the above-described lactam compound(s) or a pharmaceutically acceptable salt(s) thereof as the active ingredient.

BEST MODE FOR CARRYING OUT THE INVENTION

The detailed description on the present invention will be given below.

The term "effect of increasing the sugar-transporting capacity" as used herein indicates the effect of increasing the capacity of transporting sugar through a biological membrane. This effect includes both the transportation of sugar from the outside of the biological membrane to the inside thereof and the transportation thereof from the inside to the outside of the biological membrane. Concretely, this effect includes, for example, insulin effect of reinforcing the transportation of glucose into the muscular cells and adipose cells.

The sugars to be transported indicate pentoses and hexoses existing in a living body such as glucose, mannose, arabinose, galactose and fructose. The sugar is preferably glucose.

The term "lower alkyl group(s)" as used herein indicates a linear, branched or cyclic alkyl group(s) having 1 to 6 carbon atoms, preferably 1 to 3 carbon atoms. They include, for example, methyl group, ethyl group, n-propyl group, n-butyl group, n-pentyl group, n-hexyl group, isopropyl group, isobutyl group, sec-butyl group, tert-butyl group, isopentyl group, tert-pentyl group, neopentyl group, 2-pentyl group, 3-pentyl group, 3-hexyl group, 2-hexyl group, cyclopropyl group, cyclobutyl group, cyclopentyl group and cyclohexyl group. In them, methyl group, ethyl group, etc. are preferred.

The term "aryl group(s)" as used herein indicates a monocyclic or bicyclic aromatic substituent(s) composed of 5 to 12 carbon atoms, such as phenyl group, indenyl group, naphthyl group and fluorenyl group. In them, phenyl group is preferred.

The halogen atom(s) include fluorine atom, chlorine atom, bromine atom and iodine atom.

The term "alkyl group(s)" as used herein indicates a linear, branched or cyclic alkyl group(s) having 1 to 18 carbon atoms, such as methyl group, ethyl group, n-propyl group, n-butyl group, n-pentyl group, n-hexyl group, n-heptyl group, n-octyl group, n-nonyl group, n-decyl group, n-undecyl group, n-dodecyl group, isopropyl group, isobutyl group, sec-butyl group, tert-butyl group, isopentyl group, tert-pentyl group, neopentyl group, 2-pentyl group, 3-pentyl group, 3-hexyl group, 2-hexyl group, tert-octyl group, cyclopropyl group, cyclobutyl group, cyclopentyl group, cyclohexyl group and 1-adamantyl group. In them, preferred alkyl groups are n-hexyl group, n-heptyl group, n-octyl group, n-nonyl group, n-decyl group, n-undecyl group, n-dodecyl group, isopropyl group, isobutyl group, sec-butyl group, tert-butyl group, isopentyl group, tert-pentyl group, neopentyl group, 2-pentyl group, 3-pentyl group, 3-hexyl group, 2-hexyl group, tert-octyl group, cyclopropyl group, cyclobutyl group, cyclopentyl group, cyclohexyl group, 1-adamantyl group, etc. More preferred alkyl groups are isopropyl group, tert-butyl group, tert-octyl group, 1-adamantyl group, etc.

The term "alkenyl group(s)" as used herein indicates a linear, branched or cyclic alkenyl group(s) having 1 to 6 carbon atoms such as vinyl group, 1-propenyl group, 2-propenyl group, isopropenyl group, 1-butenyl group, 2-butenyl group and 3-butenyl group. The term "alkynyl group(s)" indicates a linear or branched alkynyl group(s) having 1 to 6 carbon atoms such as ethynyl group, 1-propynyl group, 2-propynyl group, 1-butynyl group, 2-butynyl group and 3-butynyl group.

The term "alkoxyl group(s)" as used herein indicates an alkoxyl group(s) having a linear, branched or cyclic alkyl group having 1 to 18 carbon atoms, preferably 1 to 8 carbon atoms, such as methoxyl group, ethoxyl group, n-propoxyl group, n-butoxyl group, n-pentyloxyl group, n-hexyloxyl group, n-heptyloxyl group, n-octyloxyl group, n-nonyloxyl group, n-decyloxyl group, n-undecyloxyl group, n-dodecyloxyl group, isopropoxyl group, isobutoxyl group, sec-butoxyl group, tert-butoxyl group, cyclopropyloxyl group, cyclobutoxyl group, cyclopentyloxyl group, cyclohexyloxyl group, cycloheptyloxyl group, 2-cyclohexylethoxyl group, 1-adamantyloxyl group, 2-adamantyloxyl group, 1-adamantylmethyloxyl group, 2-(1-adamantyl)ethyloxyl group and trifluoromethoxyl group. In them, preferred alkoxyl groups include methoxyl group, ethoxyl group, n-propoxyl group, isopropoxyl group, n-butoxyl group, tert-butoxyl group, n-pentyloxyl group and n-hexyloxyl group.

The term "alkylthio group(s)" as used herein indicates an alkylthio group(s) having a linear, branched or cyclic alkyl group having 1 to 12 carbon atoms, preferably 1 to 6 carbon atoms, such as methylthio group, ethylthio group, n-propylthio group, isopropylthio group, n-butylthio group, isobutylthio group, sec-butylthio group, tert-butylthio group, cyclopropylthio group, cyclobutylthio group, cyclopentylthio group and cyclobutylthio group.

The term "alkylsulfonyl group(s)" as used herein indicates an alkylsulfonyl group(s) having a linear, branched or cyclic alkyl group having 1 to 12 carbon atoms, such as methanesulfonyl group, ethanesulfonyl group, propanesulfonyl group, butanesulfonyl group, pentanesulfonyl group, hexanesulfonyl group, heptanesulfonyl group, octanesulfonyl group, nonanesulfonyl group, decanesulfonyl group, undecanesulfonyl group and dodecanesulfonyl group.

The term "acyl group(s)" as used herein indicates a formyl group, an acyl group(s) having a linear, branched or cyclic alkyl group having 1 to 6 carbon atoms, acyl group(s) having a linear, branched or cyclic alkenyl group having 1 to 6 carbon atoms, acyl group(s) having a linear, branched or cyclic alkynyl group having 1 to 6 carbon atoms or acyl group(s) having an aryl group which may be substituted, such as formyl group, acetyl group, propionyl group, butyryl group, isobutyryl group, valeryl group, isovaleryl group, pivaloyl group, hexanoyl group, acryloyl group, methacryloyl group, crotonoyl group, isocrotonoyl group, benzoyl group and naphthoyl group. Acyl groups having a heterocyclic ring can also be used, for example, furanyl carbonyl group, thienyl carbonyl group, isoxazolyl carbonyl group and thiazolyl carbonyl group.

The term "acyloxyl group(s)" as used herein indicates a formyloxyl group, an acyloxyl group(s) having a linear, branched or cyclic alkyl group having 1 to 6 carbon atoms or an acyloxyl group(s) having an aryl group which may be substituted, such as formyloxyl group, acetyloxy group, propionyloxyl group, butyryloxyl group, isobutyryloxyl group, valeryloxyl group, isovaleryloxyl group, pivaloyloxyl group, hexanoyloxyl group, acryloyloxyl group, methacryloyloxyl group, crotonoyloxyl group, isocrotonoyloxyl group, benzoyloxyl group and naphthoyloxyl group.

The term "alkylamino group(s)" as used herein indicates an amino group(s) monosubstituted or disubstituted with an alkyl group(s). Examples of the alkyl groups are those listed above for the "alkyl group(s)". The alkylamino group(s) include, for example, amino group, methylamino group, ethylamino group, propylamino group, isopropylamino group, dimethylamino group, diethylamino group, dipropylamino group, diisopropylamino group and methylethylamino group. Preferred alkylamino groups are those having 1 to 6 carbon atoms.

The term "alkoxycarbonyl group(s)" as used herein indicates an alkoxycarbonyl group(s) having a linear, branched or cyclic alkyl group having 1 to 8 carbon atoms, such as methoxycarbonyl group, ethoxycarbonyl group, propoxycarbonyl group, isopropoxycarbonyl group, n-butoxycarbonyl group, isobutoxycarbonyl group, sec-butoxycarbonyl group, tert-butoxycarbonyl group and benzyloxycarbonyl group.

The term "carbamoyl group(s)" as used herein indicates a carbamoyl group(s) which may have a linear, branched or cyclic alkyl group having 1 to 6 carbon atoms on the nitrogen atom, such as carbamoyl group, N-methylcarbamoyl group, N-ethylcarbamoyl group, N,N-dimethylcarbamoyl group, N-pyrrolidylcarbonyl group, N-piperidylcarbonyl group and N-morpholinylcarbonyl group.

The term "sulfonyl group(s)" as used herein indicates a sulfonyl group(s) which may have a linear, branched or cyclic alkyl group having 1 to 6 carbon atoms on the sulfur atom, such as methylsulfonyl group, ethylsulfonyl group, propylsulfonyl group and butylsulfonyl group.

The term "aromatic ring(s)" as used herein indicates a monocyclic or bicyclic aromatic ring(s) composed of carbon atoms, such as benzene ring, naphthalene ring, indene ring and fluorene ring. Benzene ring, naphthalene ring, etc. are preferred.

The term "heterocyclic ring(s)" as used herein indicates a heterocyclic ring(s) composed of 1 to 3 rings each comprising 5 to 7 members such as carbon and nitrogen, oxygen, sulfur or the like. They are, for example, pyridine ring, dihydropyran ring, pyridazine ring, pyrimidine ring, pyrazine ring, pyrrole ring, furan ring, thiophene ring, oxazole ring, isoxazole ring, pyrazole ring, imidazole ring, thiazole ring, isothiazole ring, thiadiazole ring, pyrrolidine ring, piperidine ring, piperazine ring, indole ring, isoindole ring, benzofuran ring, isobenzofuran ring, benzothiophene ring, benzopyrazole ring, benzoimidazole ring, benzoxazole ring, benzothiazole ring, purine ring, pyrazolopyridine ring, quinoline ring, isoquinoline ring, naphthyridine ring, quinazoline ring, benzodiazepine ring, carbazole ring and dibenzofuran ring. The heterocyclic rings are preferably pyridine ring, pyrimidine ring, pyridazine ring, pyrimidine ring, furan ring and thiophene ring. The heterocyclic rings are more preferably pyridine ring, pyrimidine ring and thiophene ring.

The term "aliphatic ring(s)" as used herein indicates a monocyclic or bicyclic aliphatic ring(s) composed of carbon atoms, such as cyclopropane ring, cyclobutane ring, cyclopentane ring, cyclohexane ring, cycloheptane ring, cyclooctane ring, decalin ring and norbornane ring. The aliphatic ring is preferably cyclohexane ring.

The term "heteroaryl group(s)" as used herein indicates a heteroaromatic substituent(s) composed of 1 to 3 rings each comprising 5 to 7 members of carbon, and nitrogen, oxygen, sulfur atoms or the like such as pyridyl group, pyridazinyl group, pyrimidinyl group, pyrazinyl group, pyrrolyl group, furanyl group, thienyl group, oxazolyl group, isoxazolyl group, pyrazolyl group, imidazolyl group, thiazolyl group, isothiazolyl group, thiadiazolyl group, indolyl group, isoindolyl group, benzofuryl group, isobenzofuryl group, benzothienyl group, benzopyrazolyl group, benzoimidazolyl group, benzoxazolyl group, benzothiazolyl group, quinolyl group, isoquinolyl group, naphthylidinyl group and quinazolyl group. In addition, oxadiazolyl group and pyridonyl group can be used. The heteroaryl groups are preferably thiazolyl group, 2-pyridyl group, 3-pyridyl group, 4-pyridyl group and 1-pyrazolyl group.

The term "aryloxyl group(s)" as used herein are those having an aryl group on the oxygen atom. Examples of the aryl groups are those listed above with reference to "aryl group(s)". Examples of the aryloxy groups are phenoxyl group, 1-naphthyloxyl group and 2-naphthyloxyl group.

The term "heteroaryloxyl group(s)" as used herein are those having a heteroaryl group on the oxygen atom. Examples of the heteroaryl groups are those listed above with reference to "heteroaryl group(s)". Examples of the heteroaryl groups are 2-pyridyloxyl group, 3-pyridyloxyl group, 4-pyridyloxyl group and 2-pyrimidinyloxyl group.

The term "arylamino group(s)" as used herein are those having an aryl group on the nitrogen atom. Examples of the aryl groups are those listed above with reference to "aryl group(s)". Examples of the arylamino groups are phenylamino group, 1-naphthylamino group and 2-naphthylamino group.

The arylvinyl groups are vinyl groups substituted with an aryl group at the 1-position or 2-position. Examples of the aryl groups are those listed above with reference to "aryl group(s)". Examples of the arylvinyl groups are 1-phenylvinyl group and 2-phenylvinyl group.

The arylethynyl groups are ethynyl groups substituted with an aryl group at the 2-position. Examples of the aryl groups are those listed above with reference to "aryl groups". An example of the arylethynyl groups is phenylethynyl group.

The expression "which may have a substituent(s)" herein indicates that the group has no substituent or that if the group is substituted, the substituent(s) is at least one of those listed in above item (I). The substituents may be the same or different from each other. The position(s) and number of the substituent(s) are not particularly limited.

In the lactam compounds or pharmaceutically acceptable salts thereof in claim 1 are preferably those of general formula (I) wherein the symbols have the following meanings:

$R^1$ is preferably hydrogen atom, methyl group, benzyl group or methoxycarbonyl methyl group, and $R^1$ is particularly preferably hydrogen atom or methyl group.

$R^2$, $R^3$ and $R^4$ are each preferably hydrogen atom, a halogen atom, hydroxyl group, an alkyl group, an alkoxyl group, an alkylthio group, an acyl group, an acyloxyl group, amino group, an alkoxycarbonyl group, carbamoyl group, nitro group, cyano group, trifluoromethyl group, an aryl group which may have a substituent(s), a heteroaryl group which may have a substituent(s), benzyloxyl group, an aryloxyl group which may have a substituent(s) or an arylethynyl group which may have a substituent(s), $R^2$, $R^3$ and $R^4$ are each more preferably hydrogen atom, a halogen atom, hydroxyl group, methyl group, ethyl group, propyl group, isopropyl group, methoxyl group, ethoxyl group, n-propoxyl group, isopropoxyl group, n-butoxyl group, benzyloxyl group or methylthio group, and $R^2$, $R^3$ and $R^4$ are each more preferably hydrogen atom, a halogen atom, methyl group, ethyl group or ethoxyl group.

—X— is preferably —NH—, —NR$^5$— wherein R$^5$ represents a lower alkyl group, —S— or —CH$_2$—, and —X— is more preferably —NH— or —NMe-.

—Y— is preferably —NH— or —NR$^5$—, wherein R$^5$ represents an acyl group which may have a substituent(s), an alkoxycarbonyl group which may have a substituent(s), carbamoyl group which may have a substituent(s) or sulfonyl group which may have a substituent(s), or —O—, —Y— is more preferably —NR$^5$—, wherein R$^5$ represents an acyl group which may have a substituent(s), an alkoxycarbonyl group which may have a substituent(s) or carbamoyl group which may have a substituent(s). In this connection, —Y— is particularly preferably —NR$^5$—, wherein R$^5$ represents an acyl group having 1 to 7 carbon atoms (preferably 2 to 6 carbon atoms, more preferably 2 or 3 carbon atoms) which may have a substituent such as halogen atoms, lower alkyloxy groups, hydroxy group, furyl group, thienyl group, oxazolyl group, isoxazolyl group, thiazolyl group, pyridyl group, pyrimidyl group and imidazolyl group. —Y— is more preferably —NAc—, —N(COCH$_2$CH$_3$)—, —N(COCH$_2$CF$_3$)—, —N(COCF$_2$CF$_3$)—, —N(COCH$_2$OEt)-, —N(COCH$_2$OH)—, —N(COOMe)- or —N(COOEt)-.

—Z— is preferably —NH— or —CH$_2$—, and —Z— is more preferably —CH$_2$—.

—W— is preferably —NH—, —NR$^1$, wherein R$^1$ represents a lower alkyl group, or —CH$_2$—, and —W— is more preferably —NH— or —NMe-.

A is preferably an aromatic ring or a heterocyclic ring. A is more preferably a benzene ring, pyridine ring, pyrimidine ring or thiophene ring. A is still more preferably a benzene ring.

B is preferably an aromatic ring which may have a substituent(s) or an aliphatic ring which may have a substituent(s). B is more preferably benzene ring which may have a substituent(s) or cyclohexane ring which may have a substituent(s). B is still more preferably cyclohexane ring which may have a substituent(s).

When B is a cyclohexane ring which may have a substituent(s), the absolute configuration of carbon atoms at a and b is preferably R or S, and it is more preferably R.

In the present invention, it is preferred that R$^5$ represents a lower alkyl group or an acyl group which may have a substituent(s), that R$^6$ and R$^7$ may be the same or different from each other and they independently represent hydrogen atom, a halogen atom, hydroxyl group, an alkyl group, an aryl group, mercapto group, an alkoxyl group, an alkylthio group, an alkylsulfonyl group, an acyl group, an acyloxyl group, amino group, an alkylamino group, carboxyl group, an alkoxycarbonyl group, carbamoyl group, nitro group, cyano group or trifluoromethyl group, and that —W— represents —NR$^1$—.

In the present invention, it is also preferred that —X— and —Y— in general formula (I) may be the same or different from each other and they each represent —NH— or —NR$^5$ wherein R$^5$ represents a lower alkyl group which may have a substituent(s), an acyl group which may have a substituent(s), an alkoxycarbonyl group which may have a substituent(s), carbamoyl group which may have a substituent(s) or sulfonyl group which may have a substituent(s), that —Z— represents —CH$_2$— or —CR$^6$R$^7$— wherein R$^6$ and R$^7$ may be the same or different from each other and they independently represent hydrogen atom, a halogen atom, hydroxyl group, an alkyl group, mercapto group, an alkoxyl group, an alkylthio group, an alkylsulfonyl group, an acyl group, an acyloxyl group, amino group, an alkylamino group, carboxyl group, an alkoxycarbonyl group, carbamoyl group, nitro group, cyano group or trifluoromethyl group and that —W— represents —NR$^1$— wherein R$^1$ represents hydrogen atom, a lower alkyl group which may have a substituent(s) or an aryl group which may have a substituent(s).

When the compounds of the present invention are sufficiently acidic, the pharmaceutically acceptable salts thereof include ammonium salts, alkali metal salts (such as, preferably, sodium salts and potassium salts), alkaline earth metal salts (such as, preferably, calcium salts and magnesium salts) and organic base salts such as dicyclohexylamine salts, benzathine salts, N-methyl-D-glucan salts, hydramine salts and amino acid salts, e.g. arginine salts and lysine salts. When the compounds of the present invention are sufficiently basic, the pharmaceutically acceptable salts thereof include acid addition salts thereof with inorganic acids such as hydrochloric acid, sulfuric acid, nitric acid and phosphoric acid, or with organic acids such as acetic acid, lactic acid, citric acid, tartaric acid, maleic acid, fumaric acid and monomethylsulfuric acid. If necessary, the salts may be hydrous or hydrated.

The present invention includes all the isomers such as optical isomers and geometric isomers, hydrates, solvates and crystal forms of the compounds. In this case, it is preferred that the absolute configurations of carbon atoms at a, b and c in general formula (I) are R or S independently from each other. It is also preferred that the absolute configuration of carbon atoms at both a and b in general formula (I) is R and the absolute configuration of carbon atom at c is R or S. It is further preferred that the absolute configurations of carbon atoms at both a and b in general formula (I) are S and the absolute configuration of carbon atom in c at R or S.

The compounds of the present invention can be synthesized by processes described below.

For example, compounds (I) of the present invention wherein —W— represents —NH—, —Z— represents —CH$_2$—, —X— and —Y— each represent —NH—, and A and B each represent benzene ring can be synthesized by condensing tetramic acid (II) with a 1,2-phenylenediamine (III) to obtain an enamine compound (IV), and reacting this compound (IV) with a corresponding aldehyde (V) as shown below:

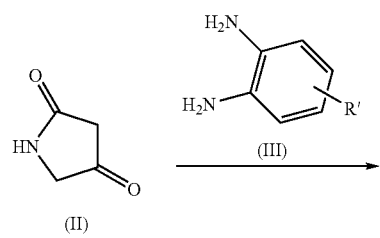

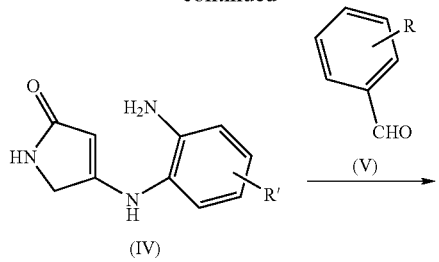

wherein R and R' each represent a substituent on the benzene ring.

The compounds (VII) wherein the amino group at the 4-position is substituted with an alkyl group can be synthesized by using an N-substituted 1,2-phenylenediamine (III') as follows:

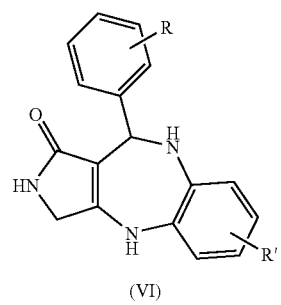

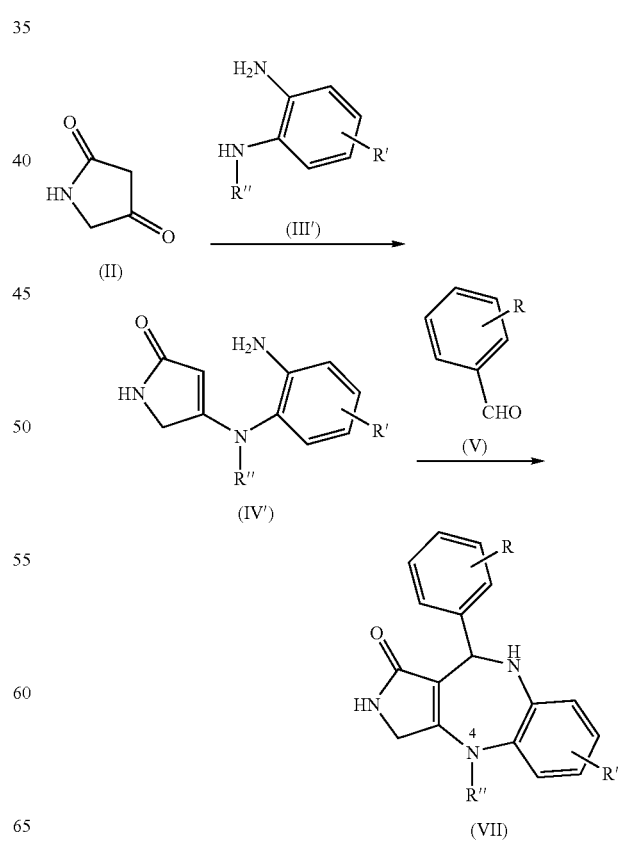

wherein R and R' each represent a substituent on the benzene ring and R" represents a substituent on the amino group at the 4-position.

The compounds (VIII) wherein the amino group at the 9-position is substituted with an alkyl group or an acyl group can be synthesized by alkylating or acylating the compounds (VI) as follows:

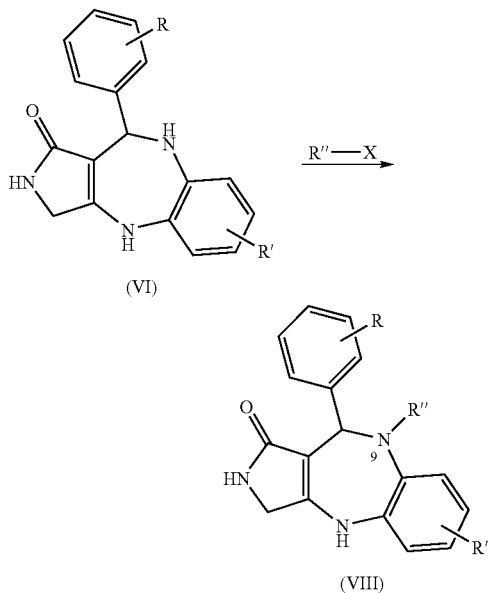

wherein R and R' each represent a substituent on the benzene ring, R" represents an alkyl or acyl group which is a substituent on the amino group at the 9-position, and X represents a leaving group such as a halogen atom.

The compounds (I) of the present invention wherein —W— represents —NH—, —Z— represents —CH$_2$—, —X— represents —NH—, —Y— represents —NAc—, A represents benzene ring and B represents cyclohexane ring can be synthesized by condensing tetramic acid (II) with a 1,2-cyclohexanediamine (III"), reacting the obtained compound with a corresponding aldehyde (V) to obtain a cyclic compound (X) and acetylating this compound (X) by an ordinary method to obtain a compound (XI). The compounds wherein —Y— is an acyl group other than —NAc— can also be synthesized by the same process as that described above or by using an acid chloride, a condensing agent or the like.

The compounds (XI) can also be synthesized by diacylating the cyclic compounds (X) to (XII) with an excess amount of an acid anhydride or the like and selectively removing the acyl group at the 4-position in the presence of a base such as potassium carbonate.

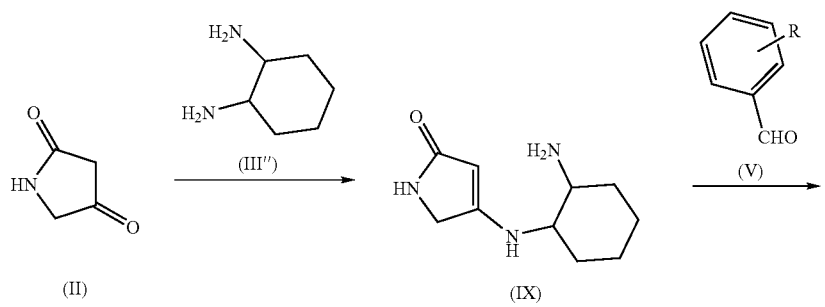

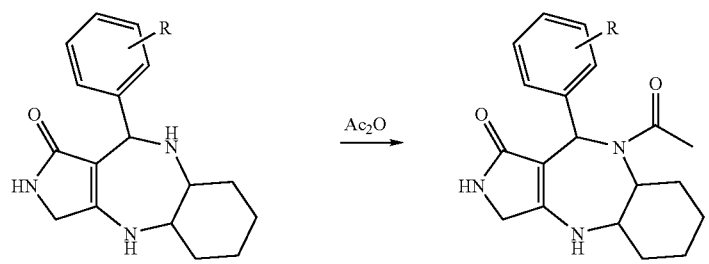

-continued

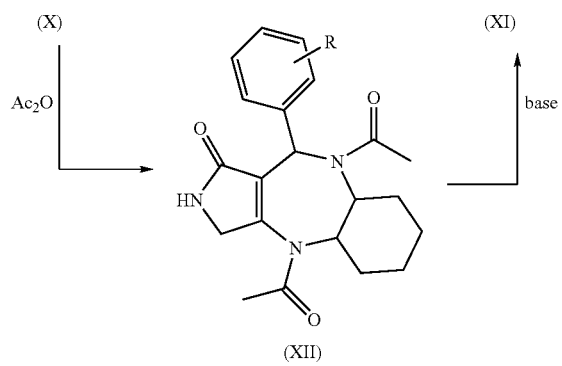

wherein R represents a substituent on the benzene ring.

The compounds of the above general formula wherein —Y— represents —NR⁵ wherein R⁵ represents an alkoxycarbonyl group can be synthesized by using a corresponding alkyl chlorocarbonate as shown by formula a) given below.

The compounds of the above general formula wherein —Y— represents —NR⁵ wherein R⁵ represents carbamoyl group can be synthesized by using a corresponding isocyanate as shown by formula b) given below.

The compounds of the above general formula wherein —Y— represents —NR⁵ wherein R⁵ represents sulfonyl group can be synthesized by using a corresponding sulfonyl chloride as shown by formula c) given below.

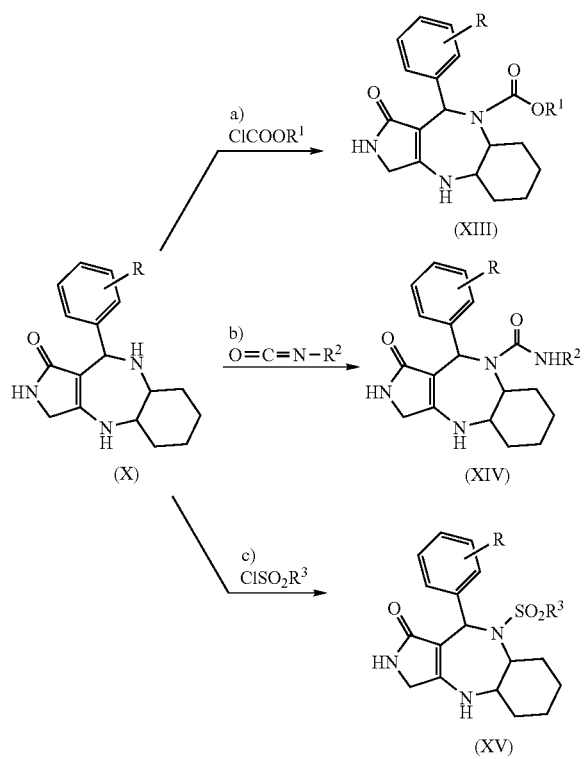

wherein R represents a substituent on the benzene ring.

The compounds (I) of the present invention wherein —W— represents —NH—, —Z— represents —CH₂—, —X— represents —S—, —Y— represents —NH— and A and B each represent benzene ring can be synthesized by condensing tetramic acid (II) with a 2-aminothiophenol (XVI) to obtain a sulfide compound (XVII) and reacting this compound with a corresponding aldehyde (V).

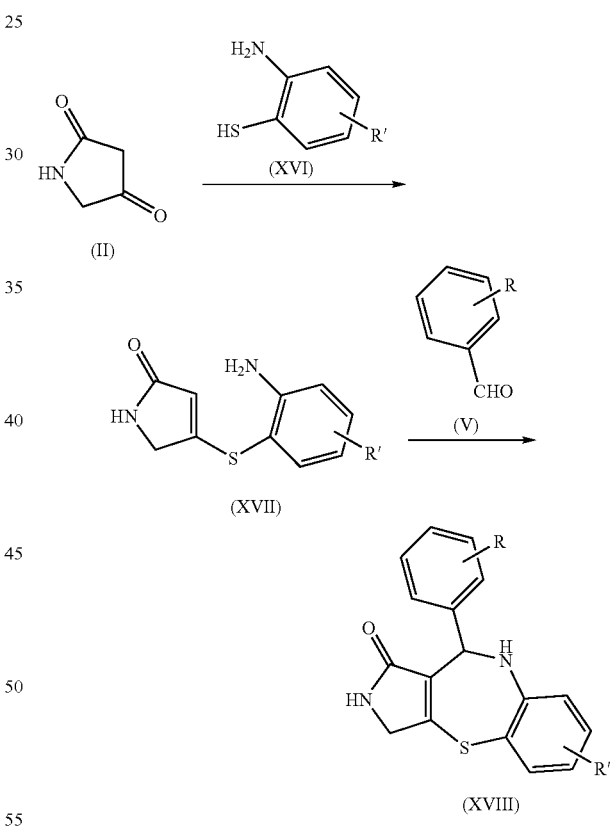

wherein R and R' each represent a substituent on the benzene ring.

The compounds (I) of the present invention wherein —W— represents —NH—, —Z— represents —CH₂—, —X— represents —NH—, —Y— represents —O— and A and B each represent benzene ring can be synthesized by condensing tetramic acid (II) with a 2-aminophenol (XIX) to obtain an enamine compound (XX) and reacting this compound with a corresponding aldehyde (V).

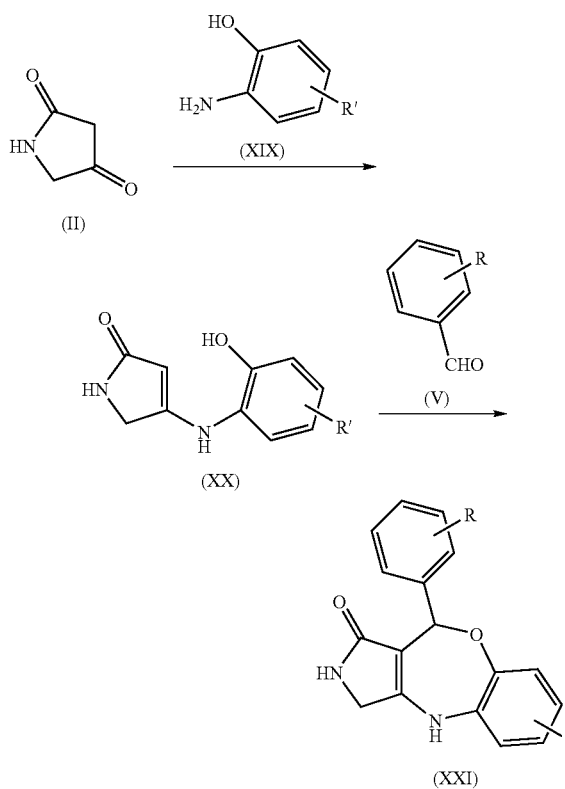

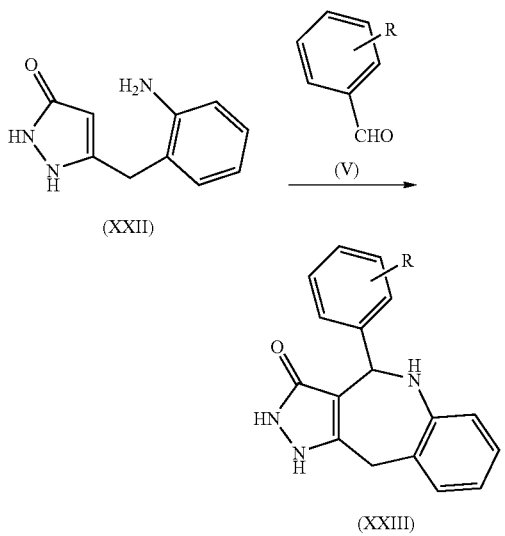

wherein R and R' each represent a substituent on the benzene ring.

The compounds (I) of the present invention wherein —W— represents —NH—, —Z— represents —NH—, —X— represents —CH$_2$—, —Y— represents —NH— and A and B each represent benzene ring can be synthesized by reacting 5-(2-aminophenyl)methyl-1,2-dihydropyrazol-3-on (XXII) described in Journal of heterocyclic chemistry, 71-5 (1989) with an aldehyde (V) as shown below:

wherein R and R' each represent a substituent on the benzene ring.

Tetramic acid used as the starting material can be synthesized by a method shown below or by a known method [Journal of chemical society, perkin trans. 1, 2907 (1973)]:

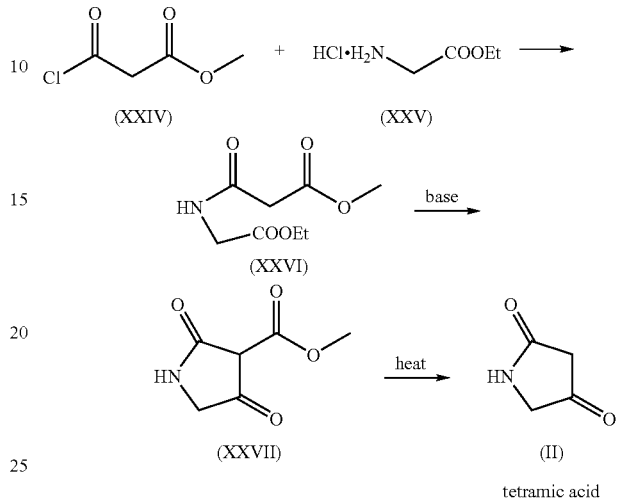

tetramic acid

The aldehydes can be synthesized by a well-known method or a method derived therefrom.

Compounds of the present invention can be synthesized by the above-described reactions as shown in Examples given below.

The compounds of the present invention obtained by the above-described processes can be purified by various purification techniques usually employed in the field of the synthesis of organic compounds, such as the extraction, distillation, crystallization and column chromatography.

The compounds of the present invention have an effect of increasing the sugar-transporting capacity, and they are effective in treating patients, taking advantage of this effect. Namely, those compounds are useful as agents for preventing and/or treating diabetes, diabetic peripheral neuropathy, diabetic nephropathy, diabetic retinopathy, diabetic macroangiopathy, impaired glucose tolerance or adiposis, because they can reduce the blood sugar level by increasing the sugar-transporting capacity.

When the compounds of the present invention are used as agents for preventing and/or treating diabetes, diabetic peripheral neuropathy, diabetic nephropathy, diabetic retinopathy, diabetic macroangiopathy, impaired glucose tolerance or adiposis, they can be administered orally, intravenously or percutaneously. The dosage of them, which varies depending on the symptoms, age and administration method of the patient, is usually 0.001 to 1,000 mg/kg/day.

The compounds of the present invention can be formulated into a pharmaceutical preparation by an ordinary method. The dosage forms of the pharmaceutical preparations are, for example, injections, tablets, granules, fine granules, powders, capsules, creams and suppositories. Carriers for the preparations are, for example, lactose, glucose, D-mannitol, starch, crystalline cellulose, calcium carbonate, kaolin, starch, gelatin, hydroxypropylcellulose, hydroxypropylmethylcellulose, polyvinylpyrrolidone, ethanol, carboxymethylcellulose, calcium salt of carboxymethylcellulose, magnesium stearate, talc, acetylcellulose, white sugar, titanium oxide, benzoic acid, para-hydroxybenzoic acid esters, sodium dehydroacetate, gum arabic, tragacanth, methylcellulose, egg yolks, surfactants, white sugar, simple syrup, citric acid, distilled water, ethanol, glycerol, propylene glycol, macrogol, disodium hydrogenphosphate, sodium dihydrogenphosphate, sodium phosphate, glucose, sodium chloride, phenol, thimerosal, para-hydroxybenzoic acid esters and sodium hydrogensulfite. The carrier is selected depending on the form of the preparation and mixed with the compound of the present invention.

The content of the active ingredient of the present invention in the preparation of the present invention is not particularly limited because it significantly varies depending on the form of the preparation. However, the active ingredient content is usually 0.01 to 100% by weight, preferably 1 to 100% by weight, based on the whole composition.

EXAMPLES

The following Examples will further specifically illustrate the present invention, which by no means limit the invention.

Example 1

(Step 1) Synthesis of pyrrolidin-2,4-dione (II: tetramic acid)

Triethylamine (72 g, 0.713 mol) was added to a solution (800 ml) of ethyl aminoacetate hydrochloride (54.68 g, 0.392 mol) in dichloromethane, and the obtained mixture was cooled at 0° C. A solution (100 ml) of methyl 3-chloro-3-oxobutanoate (48.5 g, 0.355 mol) in dichloromethane was added dropwise to the mixture during 30 minutes. The obtained mixture was stirred at room temperature for additional 4 hours. After the completion of the reaction, water (1,000 ml) was added to the reaction mixture to separate a dichloromethane layer. After the washing with aqueous sodium chloride solution followed by the drying over anhydrous sodium sulfate, the solvent was evaporated. Methanol (600 ml) and active carbon (10 g) were added to the residue, and the obtained mixture was stirred for a while and then filtered through Celite. The solvent was evaporated to obtain methyl 3-ethoxycarbonylmethylamino-3-oxobutanoate (66.9 g, 93%) in the form of a yellow oil.

1H-NMR (300 MHz, DMSO-d6) δ=1.17(3H, t, J=7.2 Hz), 3.30(2H,s), 3.60(3H, s), 3.83(2H, d, J=5.7 Hz), 4.07 (2H, q, J=7.2 Hz), 8.50(1H, broad t).

Methanol (40 ml) and toluene (400 ml) were added to the thus-obtained methyl 3-ethoxycarbonylmethylamino-3-oxobutanoate (66.9 g, 0.33 mol). 28% sodium methoxide/methanol solution (70 g, 0.363 mol) was added dropwise to the obtained mixture under thorough stirring, and they were heated at 65° C. for 1 hour. After the completion of the reaction, the reaction mixture was neutralized with 2 M hydrochloric acid (185 ml, 0.37 mol). The solid thus obtained was taken by the filtration and then dried to obtain 3-methoxycarbonylpyrrolidin-2,4-dione (39.5 g, 0.25 mol) in the form of a beige powder.

1H-NMR (300 MHz, DMSO-d6) δ=3.62(3H, s), 3.82(2H, s), 7.50(1H, broad s).

1,4-Dioxane (2,400 ml) and water (240 ml) were added to 3-methoxycarbonylpyrrolidin-2,4-dione (39.5 g, 0.25 mol) thus obtained, and they were heated under reflux for 30 minutes. After the completion of the reaction, the solvent was evaporated to obtain pyrrolidin-2,4-dione (II: tetramic acid) (24.35 g, 100%) in the form of a light yellow solid.

1H-NMR (300 MHz, DMSO-d6) ketone form δ=2.93(2H, s), 3.77(2H, s), 8.23(1H, s), enol form δ=3.74(2H, s), 4.75(1H, s), 7.07(1H, s). ketone form:enol form=about 3:2

(Step 2) Synthesis of 4-((2-aminophenyl)amino)-3-pyrrolin-2-one

A solution of pyrrolidin-2,4-dione (6.93 g, 70 mmol) produced in step 1 and 1,2-phenylenediamine (7.88 g, 70 mmol) in methanol was stirred at 60° C. for 1 hour. The reaction solution was cooled, and the crystals thus formed were taken by the filtration to synthesize 4-((2-aminophenyl) amino)-3-pyrrolin-2-one (yield: 11.6 g, 87%).

1H-NMR (300 MHz, DMSO-d6) δ=3.94(2H, s), 4.56(1H, s), 4.91(2H, broad s), 6.55(1H, dt, J=7.5, 1.5 Hz), 6.72(1H, dd, J=7.8, 1.5 Hz), 6.80(1H, s), 6.86(1H, dt, J=7.5, 1.5 Hz), 7.02(1H, dd, J=7.8, 1.5 Hz), 8.03(1H, s). MS(ESI) m/z 190(M+H)$^+$.

(Step 3) Synthesis of a Compound of Example 1

A solution of 4-((2-aminophenyl)amino)-3-pyrrolin-2-one (50 mg, 0.26 mmol) obtained in step 2 and 4-benzyloxybenzaldehyde (61 mg, 0.29 mmol) in methanol (3 ml) was stirred in the presence of acetic acid catalyst (0.01 ml) at 70° C. for 2 hours. The solvent was evaporated, and dichloromethane was added to the residue. The solid thus precipitated was taken by the filtration to synthesize the compound of Example 1 (yield: 60 mg, 54%).

1H-NMR(300 MHz, DMSO-d6) δ=3.95(2H, s), 4.98(2H, s), 4.99(1H, d, J=4.2 Hz), 5.81(1H, d, J=4.2 Hz), 6.49-6.69 (3H, m), 6.74-6.84(3H, m), 6.96-7.05(3H, m), 7.23-7.41(5H, m), 9.14(1H, s). MS(ESI) m/z 384(M+H)$^+$.

Compounds of Examples 2 to 34 were synthesized in the same manner as that in Step 3 in Example 1 except that the starting compound was replaced with a corresponding aldehyde. The aldehydes were those bought on the market or synthesized by an ordinary method.

Example 2

A compound of Example 2 (yield: 75%) was synthesized by using 4-chlorobenzaldehyde as the starting compound in the same manner as that in Step 3 in Example 1.

1H-NMR(300 MHz, DMSO-d6) δ=3.97(2H, s), 5.03(1H, d, J=4.2 Hz), 5.90(1H, d, J=4.5 Hz), 6.51(1H, dd, J=8.1, 1.5 Hz), 6.59(1H, dt, J=7.5, 1.5 Hz), 6.68(1H, dt, J=8.4, 2.1 Hz), 6.83(1H, dd, J=7.5, 1.5 Hz), 7.06(1H, s), 7.13(2H, dd, J=6.6, 1.8 Hz), 7.22(2H, dd, J=6.6, 1.8 Hz), 9.23(1H, s). MS(ESI) m/z 312(M+H)$^+$.

Example 3

A compound of Example 3 (yield: 65%) was synthesized by using 4-iodobenzaldehyde as the starting compound in the same manner as that in Step 3 in Example 1.

1H-NMR(300 MHz, DMSO-d6) δ=3.96(2H, s), 4.98(1H, d, J=4.5 Hz), 5.89(1H, d, J=4.5 Hz), 6.51(1H, d, J=7.8 Hz), 6.59(1H, t, J=7.8 Hz), 6.67(1H, t, J=7.8 Hz), 6.82(1H, d, J=7.8 Hz), 6.91(2H, d, J=7.5 Hz), 7.05(1H, s), 7.51(2H, d, J=7.5 Hz), 9.22(1H, s). MS(ESI) m/z 404(M+H)$^+$.

Example 4

A compound of Example 4 (yield: 66%) was synthesized by using 4-methylbenzaldehyde as the starting compound in the same manner as that in Step 3 in Example 1.

1H-NMR (300 MHz, DMSO-d6) δ=2.17(3H, s), 3.95(2H, s), 5.90(1H, d, J=4.5 Hz), 5.81(1H, d, J=4.5 Hz), 6.50(1H, dd, J=8.1, 1.5 Hz), 6.59(1H, dt, J=7.5, 1.5 Hz), 6.68(1H, dt, J=8.4, 2.1 Hz), 6.81(1H, dd, J=7.5, 1.5 Hz), 6.92-7.00(5H, m), 9.16(1H, s). MS(ESI) m/z 292(M+H)$^+$.

Example 5

A compound of Example 5 (yield: 34%) was synthesized by using 4-t-butylbenzaldehyde as the starting compound in the same manner as that in Step 3 in Example 1.

1H-NMR(300 MHz, DMSO-d6) δ=1.18(9H, s), 3.92(2H, s), 4.96(1H, d, J=4.5 Hz), 5.87(1H, d, J=4.5 Hz), 6.53-6.67 (3H, m), 6.80(1H, d, J=7.5 Hz), 6.96-7.05(3H, m), 7.15(2H, d, J=8.4 Hz), 9.15(1H, s). MS(ESI) m/z 334(M+H)$^+$.

Example 6

(Step 1) Synthesis of 4-(2-phenylethynyl)benzaldehyde

4-Bromobenzaldehyde (370 mg, 2 mmol), phenylacetylene (306 mg, 3 mmol) and tetrakistriphenylphosphine palladium (45 mg) were dissolved in triethylamine (4 ml), and the obtained solution was stirred at 80° C. in argon atmosphere for 24 hours. The solvent was evaporated, and the product was purified by the silica gel column chromatography to obtain 4-(2-phenylethynyl)benzaldehyde (yield: 258 mg, 63%)

1H-NMR(300 MHz, CDCl3) δ=7.30-7.40(3H, m), 7.50-7.60(2H, m), 7.68(2H, d, J=8.1 Hz), 7.87(2H, d, J=8.1 Hz), 10.02(1H, s).

(Step 2) Synthesis of a Compound of Example 6

The compound of Example 6 (yield: 34%) was synthesized by using 4-(2-phenylethynyl)benzaldehyde as the starting compound in the same manner as that in Step 3 in Example 1.

1H-NMR(300 MHz, DMSO-d6) δ=3.99(2H, s), 5.06(1H, d, J=3.9 Hz), 5.94(1H, d, J=4.5 Hz), 6.50-6.71(3H, m), 6.84(1H, d, J=7.5 Hz), 7.80(1H, s), 7.15(2H, d, J=8.1 Hz), 7.35(2H, d, J=8.1 Hz), 7.38-7.42(3H, m), 7.48-7.54(2H, m), 9.25(1H, s). MS(ESI) m/z 334(M+H)$^+$.

Example 7

A compound of Example 7 (yield: 24%) was synthesized by using 4-phenylbenzaldehyde as the starting compound in the same manner as that in Step 3 in Example 1.

1H-NMR(300 MHz, DMSO-d6) δ=3.98(2H, s), 5.07(1H, d, J=4.2 Hz), 5.95(1H, d, J=4.2 Hz), 6.56-6.71(3H, m), 6.84(1H, d, J=6.9 Hz), 7.05(1H, s), 7.20(2H, d, J=8.1 Hz), 7.26-7.49(5H, m), 7.57(2H, d, J=8.1 Hz), 9.22(1H, s). MS(ESI) m/z 354(M+H)$^+$.

Example 8

(Step 1) Synthesis of 4-(4-nitrophenyl)benzaldehyde

1 M solution (1.2 ml, 1.22 mmol) of diisobutylaluminum hydride in toluene was slowly added to a solution (10 ml) of 4-(4-nitrophenyl)benzonitrile (224 mg, 1 mmol) in toluene at room temperature, and they were stirred for 1 hour. After cooling to 0° C., methanol (0.4 ml) and water (0.4 ml) were slowly added to the obtained mixture, and they were stirred. The reaction mixture was dried over sodium sulfate. After the purification by the silica gel column chromatography (ethyl acetate/hexane), 4-(4-nitrophenyl)benzaldehyde was obtained in the form of a yellow solid (yield: 127 mg, 56%).

1H-NMR(300 MHz, CDCl3) δ=7.80(4H, d, J=8.7 Hz), 8.03(2H, d, J=8.4 Hz), 8.36(2H, d, J=9.0 Hz), 10.11(1H, s).

(Step 2) Synthesis of a Compound of Example 8

A compound of Example 8 (yield: 67%) was synthesized by using 4-(4-nitrophenyl)benzaldehyde as the starting compound in the same manner as that in Step 3 in Example 1.

1H-NMR(300 MHz, DMSO-d6) δ=3.97(2H, s), 5.08(1H, d, J=4.2 Hz), 5.98(1H, d, J=4.2 Hz), 6.55-6.70(3H, m), 6.84(1H, d, J=7.2 Hz), 7.05(1H, s), 7.25(2H, d, J=8.4 Hz), 7.59(2H, d, J=8.4 Hz), 7.87(2H, d, J=9.0 Hz), 8.23(2H, d, J=9.0 Hz), 9.24(1H, s). MS(ESI) m/z 397(M−H)$^−$.

Example 9

A compound of Example 9 (yield: 22%) was synthesized by using 2-fluorenecarboxyaldehyde as the starting compound in the same manner as that in Step 3 in Example 1.

1H-NMR(300 MHz, DMSO-d6) δ=3.77(2H, s), 4.00(2H, s), 5.12(1H, d, J=4.5 Hz), 5.90(1H, d, J=4.5 Hz), 6.50-6.69 (3H, m), 6.84(1H, d, J=7.5 Hz), 7.04(1H, s), 7.14(1H, d, J=7.5 Hz), 7.21-7.36(3H, m), 7.51(1H, d, J=7.5 Hz), 7.66 (1H, d, J=7.5 Hz), 7.77(1H, d, J=7.5 Hz), 9.21(1H, s). MS(ESI) m/z 366(M+H)$^+$.

Example 10

A compound of Example 10 (yield: 48%) was synthesized by using 4-butoxybenzaldehyde as the starting compound in the same manner as that in Step 3 in Example 1.

1H-NMR(300 MHz, DMSO-d6) δ=0.88(3H, t, J=7.4 Hz), 1.30-1.45(2H, m), 1.56-1.68(2H, m), 3.84(2H, t, J=6.3 Hz), 3.95(2H, s), 4.98(1H, d, J=4.2 Hz), 5.79(1H, d, J=4.2 Hz), 6.47-6.84(6H, m), 6.93-7.06(3H, m), 9.13(1H, s). MS(ESI) m/z 350(M+H)$^+$.

Example 11

(Step 1) Synthesis of 4-dodecyloxybenzaldehyde

4-Hydroxybenzaldehyde (673 mg, 5.5 mmol), 1-bromododecane (1.25 g, 5 mmol) and potassium carbonate (859 mg, 6.22 mmol) were added to dimethylformamide (3 ml), and they were stirred at 65° C. for 18 hours. After the completion of the reaction followed by the extraction with ethyl acetate, 4-dodecyloxybenzaldehyde (yield: 1.45 g, 99%) was obtained in the form of white crystals.

(Step 2) Synthesis of a Compound of Example 11

The compound of Example 11 (yield: 82%) was synthesized by using 4-dodecyloxyaldehyde as the starting compound in the same manner as that in Step 3 in Example 1.

1H-NMR(300 MHz, DMSO-d6) δ=0.85(3H, t, J=6.6 Hz), 1.10-1.40(18H, m), 1.55-1.68(2H, m), 3.82(2H, t, J=6.6 Hz), 3.95(2H, s), 4.98(1H, d, J=4.5 Hz), 5.78(1H, d, J=4.5 Hz), 6.49-6.72(5H, m), 6.80(1H, d, J=9.0 Hz), 6.97-7.04(3H, m), 9.13(1H, s). MS(ESI) m/z 462(M+H)$^+$.

Example 12

A compound of Example 12 (yield: 79%) was synthesized by using 4-cycloheptyloxybenzaldehyde as the starting compound in the same manner as that in Step 3 in Example 1. The starting aldehyde was synthesized from 4-hydroxybenzaldehyde and bromocycloheptane in the same manner as that in Step 1 in Example 11.

1H-NMR(300 MHz, DMSO-d6) δ=1.29-1.65(10H, m), 1.79-1.90(2H, m), 3.92(2H, s), 4.28-4.40(1H, m), 4.95(1H, d, J=3.6 Hz), 5.77(1H, d, J=4.8 Hz), 6.48-6.68(5H, m), 6.79(1H, d, J=7.8 Hz), 6.95-7.02(3H, m), 9.12(1H, s). MS(ESI) m/z 388(M−H)⁻.

Example 13

A compound of Example 13 (yield: 55%) was synthesized by using 4-(2-adamantyloxy)benzaldehyde as the starting compound in the same manner as that in Step 3 in Example 1. The starting aldehyde was synthesized from 4-hydroxybenzaldehyde and 2-bromoadamantane in the same manner as that in Step 1 in Example 11.

1H-NMR(300 MHz, DMSO-d6) δ=1.40-1.50(2H, d-like), 1.66-1.85(8H, m), 1.97(4H, s-like), 4.35(1H, s), 4.97(1H, d, J=4.2 Hz), 5.81(1H, d, J=4.2 Hz), 6.50-6.85(6H, m), 6.96-7.05(3H, m), 9.15(1H, s). MS(ESI) m/z 428(M+H)⁺.

Example 14

A compound of Example 14 (yield: 48%) was synthesized by using 4-(1-adamantylmethoxy)benzaldehyde as the starting compound in the same manner as that in Step 3 in Example 1. The starting aldehyde was synthesized from 4-hydroxybenzaldehyde and 1-adamantylmethyl trifluoromethanesulfonate in the same manner as that in Step 1 in Example 11.

1H-NMR(300 MHz, DMSO-d6) δ=1.50-1.75(12H, m), 1.90-2.00(3H, brs), 3.41(2H, s), 3.95(2H, s), 4.98(1H, d, J=4.5 Hz), 5.78(1H, d, J=4.5 Hz), 6.48-6.76(5H, m), 6.80(1H, d, J=8.1 Hz), 6.96-7.08(3H, m), 9.14(1H, s). MS(ESI) m/z 442(M+H)⁺.

Example 15

A compound of Example 15 (yield: 36%) was synthesized by using 4-(2-(1-adamantyl)ethyl)oxybenzaldehyde as the starting compound in the same manner as that in Step 3 in Example 1. The starting aldehyde was synthesized by the Mitsunobu reaction of 4-hydroxybenzaldehyde and 2-(1-adamantyl)ethanol.

1H-NMR(300 MHz, DMSO-d6) δ=1.40-1.70(14H, m), 1.90(3H, brs), 3.90(2H, t, J=7.2 Hz), 3.95(2H, s), 4.98(1H, d, J=4.5 Hz), 5.79(1H, d, J=4.5 Hz), 6.50-6.85(6H, m), 6.98-6.97-7.03(3H, m), 9.14(1H, s). MS(ESI) m/z 456(M+H)+.

Example 16

A compound of Example 16 (yield: 54%) was synthesized by using 4-(2-cyclohexylethyl)oxybenzaldehyde as the starting compound in the same manner as that in Step 3 in Example 1. The starting aldehyde was synthesized from 4-hydroxybenzaldehyde and 2-cyclohexylethyl bromide in the same manner as that in Step 1 in Example 11.

1H-NMR(300 MHz, DMSO-d6) δ=0.82-1.00(2H, m), 1.06-1.26(3H, m), 1.32-1.49(1H, m), 1.49-1.74(7H, m), 3.87 (2H, t, J=6.6 Hz), 3.95(2H, s), 4.98(1H, d, J=4.2 Hz), 5.78(1H, d, J=4.5 Hz), 6.49-6.72(5H, m), 6.80(1H, dd, J=1.5, 7.8 Hz), 6.97-7.03(3H, m), 9.13(1H, s). MS(ESI) m/z 402(M−H)⁻.

Example 17

(Step 1) Synthesis of 1-(4-formylphenyl)pyrazole

Copper acetate (91 mg, 0.5 mmol), pyridine (53 mg, 0.67 mmol) and active Molecular Sieve 4A (250 mg) were added to a solution of 4-formylphenylboronic acid (100 mg, 0.67 mmol) and pyrazole (16 mg, 0.33 mmol) in 1,4-dioxane (4 ml), and they were stirred at room temperature for 72 hours. The reaction mixture was filtered through Celite, and the obtained filtrate was concentrated and then purified by the silica gel TLC chromatography to obtain 1-(4-formylphenyl)pyrazole (yield: 38 mg, 66%) in the form of a white powder.

1H-NMR(300 MHz, CDCl₃) δ=6.53-8.04(7H, m), 10.02 (1H, s).

(Step 2) Synthesis of a Compound of Example 17

The compound of Example 17 (yield: 74%) was synthesized by using 1-(4-formylphenyl)pyrazole as the starting compound in the same manner as that in Step 3 in Example 1.

¹H-NMR(300 MHz, DMSO-d6) δ=3.99(2H, s), 5.08(1H, d, J=4.2 Hz), 5.93(1H, d, J=4.5 Hz), 6.47-8.37(11H, m), 7.07(1H, s), 9.23(1H, s). MS(ESI) m/z 344(M+H)⁺.

Example 18

A compound of Example 18 (yield: 24%) was synthesized by using 2-bromobenzaldehyde as the starting compound in the same manner as that in Step 3 in Example 1.

1H-NMR(300 MHz, DMSO-d6) δ=4.02(2H, s), 5.28(1H, d, J=4.5 Hz), 5.39(1H, d, J=4.5 Hz), 6.42(1H, d, J=7.8 Hz), 6.56(1H, t, J=7.8 Hz), 6.68-6.77(2H, m), 6.87(1H, d, J=7.8 Hz), 7.01-7.09(2H, m), 7.12(1H, s), 7.53-7.62(1H, m), 9.35 (1H, s). MS(ESI) m/z 356, 358(M+H)⁺.

Example 19

A compound of Example 19 (yield: 38%) was synthesized by using 2-methoxybenzaldehyde as the starting compound in the same manner as that in Step 3 in Example 1.

1H-NMR(300 MHz, DMSO-d6) δ=3.92(3H, s), 3.97(1H, d, J=16.5 Hz), 4.04(1H, d, J=16.5 Hz), 5.16(1H, d, J=4.5 Hz), 5.33(1H, d, J=4.5 Hz), 6.38(1H, d, J=7.5 Hz), 6.48-6.68(4H, m), 6.80(1H, d, J=7.5 Hz), 6.95(1H, d, J=7.5 Hz), 7.00-7.12(2H, m), 9.19(1H, s). MS(ESI) m/z 308(M+H)⁺.

Example 20

A compound of Example 20 (yield: 50%) was synthesized by using 2,4-dichlorobenzaldehyde as the starting compound in the same manner as that in Step 3 in Example 1.

1H-NMR(300 MHz, DMSO-d6) δ=4.02(2H, s), 5.39(1H, d, J=4.5 Hz), 5.43(1H, d, J=4.5 Hz), 6.47(1H, d, J=7.5 Hz), 6.59(1H, t, J=7.5 Hz), 6.69-6.77(2H, m), 6.88(1H, d, J=7.5 Hz), 7.07-7.16(2H, m), 7.56(1H, brs), 9.36(1H, s). MS(ESI) m/z 346(M+H)⁺.

Example 21

(Step 1) Synthesis of 4-butoxy-2-methoxybenzaldehyde

Potassium carbonate (1.50 g, 10.9 mmol) and butyl iodide (666 mg, 3.6 mmol) were added to a solution of 2,4-dihydroxybenzaldehyde (500 mg, 3.6 mmol) in dimethylformamide (5 ml), and they were stirred at room temperature for 2 hours. Then methyl iodide (2.57 ml) was added to the reaction mixture, and they were stirred at room temperature for 12 hours. After the extraction with ethyl acetate followed by the silica gel chromatography, 4-butoxy-2-methoxybenzaldehyde (yield: 233 mg, 31%) was obtained in the form of a colorless oil.

1H-NMR(300 MHz, CDCl3) δ=1.00(3H, t, J=7.5 Hz), 1.44-1.59(2H, m), 1.73-1.86(2H, m), 3.91(3H, s), 4.04(2H, t, J=6.6 Hz), 6.45(1H, brs), 6.54(1H, d, J=8.4 Hz), 7.80(1H, d, J=8.4 Hz), 10.29(1H, s).

(Step 2) Synthesis of a Compound of Example 21

The compound of Example 21 (yield: 59%) was synthesized by using 4-butoxy-2-methoxybenzaldehyde as the starting compound in the same manner as that in Step 3 in Example 1.

1H-NMR(300 MHz, DMSO-d6) δ=0.89(3H, t, J=7.8 Hz), 1.31-1.46(2H, m), 1.56-1.68(2H, m), 3.84(2H, t, J=6.3 Hz), 3.90(3H, s), 3.99(2H, brs), 5.08(1H, d, J=3.9 Hz), 5.22(1H, d, J=3.9 Hz), 6.15(1H, d, J=8.4 Hz), 6.35-6.58(4H, m), 6.64(1H, t, J=8.4 Hz), 6.79(1H, d, J=8.4 Hz), 7.02(1H, s), 9.15(1H, s). MS(ESI) m/z 380(M+H)$^+$.

Example 22

(Step 1) Synthesis of 2,4-dibutoxybenzaldehyde

Potassium carbonate (1.50 g, 10.9 mmol) and butyl iodide (1.66 g, 9.05 mmol) were added to a solution of 2,4-dihydroxybenzaldehyde (500 mg, 3.6 mmol) in dimethylformamide (5 ml), and they were stirred at room temperature for 12 hours. After the extraction with ethyl acetate followed by the silica gel chromatography, 2,4-dibutoxybenzaldehyde (yield: 833 mg, 92%) was obtained in the form of a colorless oil.

1H-NMR(300 MHz, CDCl3) δ=0.94-1.05(6H, m), 1.43-1.60(4H, m), 1.73-1.89(4H, m), 3.47-4.08(4H, m), 6.43(1H, brs), 6.52(1H, d, J=8.1 Hz), 7.80(1H, d, J=8.1 Hz), 10.33(1H, s).

(Step 2) Synthesis of a Compound of Example 22

The compound of Example 22 (yield: 12%) was synthesized by using 2,4-dibutoxybenzaldehyde as the starting compound in the same manner as that in Step 3 in Example 1.

1H-NMR(300 MHz, DMSO-d6) δ=0.89(3H, t, J=7.5 Hz), 1.02(3H, t, J=7.5 Hz), 1.30-1.46(2H, m), 1.48-1.67(4H, m), 1.80-1.94(2H, m), 3.83(2H, t, J=6.3 Hz), 3.92-4.18(4H, m), 4.89(1H, d, J=4.5 Hz), 5.23(1H, d, J=4.5 Hz), 6.15(1H, dd, J=8.7, 2.4 Hz), 6.32(1H, d, J=7.5 Hz), 6.45(1H, d, J=8.7 Hz), 6.49(1H, d, J=2.4 Hz), 6.54(1H, t, J=7.5 Hz), 6.65(1H, t, J=7.5 Hz), 6.80(1H, d, J=7.5 Hz), 7.04(1H, s), 9.17(1H, s). MS(ESI) m/z 422(M+H)$^+$.

Example 23

A compound of Example 23 (yield: 90%) was synthesized by using 4-butoxy-2-ethoxybenzaldehyde as the starting compound in the same manner as that in Step 3 in Example 1. The starting aldehyde was synthesized from 2,4-dihydroxybenzaldehyde, butyl iodide and ethyl bromide in the same manner as that in Step 1 in Example 21.

1H-NMR(300 MHz, DMSO-d6) δ=0.89(1H, t, J=7.5 Hz), 1.30-1.45(2H, m), 1.48(3H, t, J=7.2 Hz), 1.55-1.67(2H, m), 3.83(2H, t, J=6.6 Hz), 3.99(2H, brs), 4.08-4.23(2H, m), 4.98(1H, d, J=4.5 Hz), 5.23(1H, d, J=4.5 Hz), 6.15(1H, dd, J=8.4, 2.4 Hz), 6.36(1H, d, J=7.8 Hz), 6.45(1H, d, J=8.4 Hz), 6.47(1H, d, J=2.4 Hz), 6.53(1H, t, J=7.8 Hz), 6.65(1H, t, J=7.8 Hz), 6.80(1H, d, J=7.8 Hz), 7.03(1H, s), 9.16(1H, s). MS(ESI) m/z 394(M+H)$^+$.

Example 24

A compound of Example 24 (yield: 79%) was synthesized by using 4-butoxy-2-propoxybenzaldehyde as the starting compound in the same manner as that in Step 3 in Example 1. The starting aldehyde was synthesized from 2,4-dihydroxybenzaldehyde, butyl iodide and propyl iodide in the same manner as that in Step 1 in Example 21.

1H-NMR(300 MHz, DMSO-d6) δ=0.89(3H, t, J=7.5 Hz), 1.10(3H, t, J=7.5 Hz), 1.30-1.45(2H, m), 1.56-1.68(2H, m), 1.83-1.97(2H, m), 3.83(2H, t, J=6.6 Hz), 3.93-4.13(4H, m), 4.90(1H, d, J=4.5 Hz), 5.24(1H, d, J=4.5 Hz), 6.15(1H, dd, J=8.4, 2.4 Hz), 6.33(1H, d, J=7.8 Hz), 6.46(1H, d, J=8.4 Hz), 6.48(1H, d, J=2.4 Hz), 6.54(1H, t, J=7.8 Hz), 6.65(1H, t, J=7.8 Hz), 6.80(1H, d, J=7.8 Hz), 7.04(1H, s), 9.17(1H, s). MS(ESI) m/z 408(M+H)$^+$.

Example 25

A compound of Example 25 (yield: 80%) was synthesized by using 4-ethoxy-2-propoxybenzaldehyde as the starting compound in the same manner as that in Step 3 in Example 1. The starting aldehyde was synthesized from 2,4-dihydroxybenzaldehyde, ethyl bromide and propyl iodide in the same manner as that in Step 1 in Example 21.

1H-NMR(300 MHz, DMSO-d6) δ=1.10(3H, t, J=7.5 Hz), 1.25(3H, t, J=7.2 Hz), 1.83-1.97(2H, m), 3.89(2H, t, J=7.2 Hz), 3.95-4.14(4H, m), 4.91(1H, d, J=4.2 Hz), 5.24(1H, d, J=4.2 Hz), 6.15(1H, dd, J=8.4, 2.4 Hz), 6.33(1H, d, J=7.8 Hz), 6.46(1H, d, J=8.4 Hz), 6.48(1H, d, J=2.4 Hz), 6.54(1H, t, J=7.8 Hz), 6.65(1H, t, J=7.8 Hz), 6.80(1H, d, J=7.8 Hz), 7.04(1H, s), 9.17(1H, s). MS(ESI) m/z 380(M+H)$^+$.

Example 26

A compound of Example 26 (yield: 85%) was synthesized by using 2-ethoxy-4-propoxybenzaldehyde as the starting compound in the same manner as that in Step 3 in Example 1. The starting aldehyde was synthesized from 2,4-dihydroxybenzaldehyde, propyl iodide and ethyl bromide in the same manner as that in Step 1 in Example 21.

1H-NMR(300 MHz, DMSO-d6) δ=0.92(3H, t, J=7.5 Hz), 1.48(3H, t, J=7.2 Hz), 1.57-1.72(2H, m), 3.78(2H, t, J=6.6 Hz), 4.00(2H, brs), 4.06-4.24(2H, m), 4.98(1H, d, J=4.5 Hz), 5.23(1H, d, J=4.5 Hz), 6.14(1H, dd, J=8.4, 2.4 Hz), 6.36(1H, d, J=7.8 Hz), 6.45(1H, d, J=8.4 Hz), 6.47(1H, d, J=2.4 Hz), 6.54(1H, t, J=7.8 Hz), 6.65(1H, t, J=7.8 Hz), 6.79(1H, d, J=7.8 Hz), 7.03(1H, s), 9.16(1H, s). MS(ESI) m/z 380(M+H)$^+$.

Example 27

A compound of Example 27 (yield: 53%) was synthesized by using 4-hexyloxy-2-methoxybenzaldehyde as the starting compound in the same manner as that in Step 3 in Example 1. The starting aldehyde was synthesized from 2,4-dihydroxybenzaldehyde, hexyl bromide and methyl iodide in the same manner as that in Step 1 in Example 21.

1H-NMR(300 MHz, DMSO-d6) δ=0.85(3H, t, J=7.2 Hz), 1.19-1.43(6H, m), 1.56-1.69(2H, m), 3.83(2H, t, J=6.6 Hz), 3.90(3H, s), 3.99(2H, brs), 5.08(1H, d, J=4.2 Hz), 5.22(1H, d, J=4.2 Hz), 6.15(1H, dd, J=8.4, 2.4 Hz), 6.38(1H, d, J=7.8 Hz), 6.44(1H, d, J=8.4 Hz), 6.49(1H, d, J=2.4 Hz), 6.53(1H, t, J=7.8 Hz), 6.64(1H, t, J=7.8 Hz), 6.79(1H, d, J=7.8 Hz), 7.02(1H, s), 9.15(1H, s). MS(ESI) m/z 408(M+H)+.

Example 28

A compound of Example 28 (yield: 23%) was synthesized by using 4-benzyloxy-2-methoxybenzaldehyde as the starting compound in the same manner as that in Step 3 in Example 1.

1H-NMR(300 MHz, DMSO-d6) δ=3.90(3H, s), 3.97(1H, d, J=15 Hz), 4.02(1H, d, J=15 Hz), 4.97(2H, s), 5.10(1H, d, J=4.5 Hz), 5.23(1H, d, J=4.5 Hz), 6.26(1H, dd, J=2.4, 8.4 Hz), 6.40(1H, d, J=7.5 Hz), 6.47(1H, d, J=8.4 Hz), 6.53(1H, t, J=7.5 Hz), 6.58-6.69(3H, m), 6.79(1H, d, J=7.5 Hz), 7.02(1H, s), 7.26-7.43(6H, m), 9.16(1H, s). MS(ESI) m/z 414(M+H)+.

Example 29

(Step 1) Synthesis of 4-hexyloxy-2-hydroxybenzaldehyde 2,4-Dihydroxybenzaldehyde (3.00 g, 21.7 mmol) and hexyl bromide (7.62 ml, 54.3 mmol) were stirred in the presence of lithium carbonate (4.00 g, 54.3 mmol) in dimethylformamide (5 ml) at 55° C. overnight. After the neutralization with hydrochloric acid followed by the extraction with ethyl acetate, the product was purified by the silica gel column chromatography to obtain 4-hexyloxy-2-hydroxybenzaldehyde (yield: 1.77 g, 37%) in the form of a colorless oil.

1H-NMR (300 MHz, CDCl3) δ=0.91(3H, m), 1.32-1.48 (6H, m), 1.77-1.84(2H, m), 4.01(2H, t, J=6.6 Hz), 6.41(1H, d, J=2.1 Hz), 6.53(1H, dd, J=8.7, 2.1 Hz), 7.42(1H, d, J=8.7 Hz), 9.70(1H, s).

(Step 2) Synthesis of a Compound of Example 29

The compound of Example 29 (yield: 73%) was synthesized by using 4-hexyloxy-2-hydroxybenzaldehyde as the starting compound in the same manner as that in Step 3 in Example 1.

1H-NMR(300 MHz, DMSO-d6) δ=0.85(3H, t, J=6.9 Hz), 1.17-1.41(6H, m), 1.53-1.68(2H, m), 3.76(2H, t, J=6.6 Hz), 3.99(2H, brs), 5.21(2H, s), 6.04(1H, dd, J=8.4, 2.4 Hz), 6.34(1H, d, J=2.4 Hz), 6.42(1H, d, J=8.4 Hz), 6.46(1H, d, J=7.8 Hz), 6.57(1H, t, J=7.8 Hz), 6.65(1H, t, J=7.8 Hz), 6.81(1H, d, J=7.8 Hz), 7.09(1H, s), 9.16(1H, s), 9.92(1H, s). MS(ESI) m/z 394(M+H)+.

Example 30

(Step 1) Synthesis of 4-t-butyl-2-chlorobenzaldehyde

(Step 1-1) Synthesis of 2-chloro-4-t-butylphenol 4-t-Butylphenol (2.76 g, 18.4 mmol) was dissolved in dichloromethane (25 ml). Sulfuryl chloride (1.6 ml, 9.9 mmol) was added dropwise to the obtained solution, and they were stirred at room temperature for 3 days and then concentrated under reduced pressure. After the purification by the silica gel column chromatography, 2-chloro-4-t-butylphenol (yield: 2.71 g, 80%) was obtained.

1H-NMR(300 MHz, CDCl3) δ=1.28(9H, s), 5.37(1H, s), 6.94(1H, d, J=8.6 Hz), 7.19(1H, dd, J=8.6 Hz, 2.5 Hz), 7.30(1H, d, J=2.5 Hz).

(Step 1-2) Synthesis of 2-chloro-4-t-butylphenyl trifluoromethane-sulfonate The chloro-compound (1.84 g, 10 mmol) obtained in step 1-1 and pyridine (1.2 ml) were dissolved in dichloromethane (20 ml). Trifluoromethanesulfonic anhydride (2.5 ml) was slowly added dropwise to the obtained solution. After stirring at room temperature for 10 minutes, hexane (20 ml) was added to the reaction mixture. An insoluble matter was removed by the filtration, and the filtrate was concentrated under reduced pressure. After the purification by the silica gel column chromatography, 2-chloro-4-t-butylphenyl trifluoromethane-sulfonate (yield: 2.94 g, 93%) was obtained.

1H-NMR(300 MHz, CDCl3) δ=1.32(9H, s), 7.25(1H, d, J=8.6 Hz), 7.34(1H, dd, J=8.6 Hz, 2.1 Hz), 7.50(1H, d, J=2.1 Hz).

(Step 1-3) Synthesis of 2-chloro-4-t-butylbenzyl alcohol

The triflate compound (638 mg, 2 mmol) obtained in Step 1-2, palladium acetate (14 mg), 1,3-diphenylphosphinopropane (25 mg), methanol (4 ml) and triethylamine (0.6 ml) were dissolved in dimethylformamide (5 ml), and the obtained solution was stirred at 80° C. in carbon monoxide atmosphere for 16 hours. After leaving the reaction mixture to cool followed by the extraction with ethyl acetate/hexane and the purification by the silica gel column chromatography, methyl 2-chloro-4-t-butylbenzoate was obtained. The ester thus obtained was dissolved in dichloromethane (2 ml). 1 M solution (2.5 ml) of diisobutylaluminum hydride in toluene was added dropwise to the obtained solution at −78° C. in argon atmosphere, and the resulting solution was stirred at that temperature for 5 minutes. 0.5 M hydrochloric acid (20 ml) was added to the reaction mixture, and the temperature was elevated to room temperature. After the extraction with ethyl acetate followed by the purification by the silica gel column chromatography, 2-chloro-4-t-butylbenzyl alcohol (yield: 204 mg, 51%) was obtained.

1H-NMR(300 MHz, CDCl3) δ=1.31(9H, s), 1.8-2.1(1H, br), 4.75(2H, s), 7.29(1H, dd, J=7.8 Hz, 2.1 Hz), 7.36-7.41 (2H, m).

(Step 1-4) Synthesis of 2-chloro-4-t-butylbenzaldehyde

The alcohol compound (195 mg, 0.981 mmol) obtained in Step 1-3 was dissolved in chloroform (5 ml). Activated manganese dioxide (1.27 g) was added to the obtained solution, and they were violently stirred at 50° C. for 2 hours. After leaving to cool, manganese dioxide was filtered out, and the filtrate was concentrated under reduced pressure. After the purification by the silica gel column chromatography, 2-chloro-4-t-butylbenzaldehyde (yield: 152 mg, 79%) was obtained.

1H-NMR(300 MHz, CDCl3) δ=1.34(9H, s), 7.40(1H, ddd, J=8.1 Hz, 1.8 Hz, 0.9 Hz), 7.44(1H, d, J=1.8 Hz), 7.86(1H, d, J=8.1 Hz), 10.43(1H, d, J=0.9 Hz).

(Step 2) Synthesis of a Compound of Example 30

The compound of Example 30 (yield: 51%) was synthesized by using 4-t-butyl-2-chlorobenzaldehyde as the starting compound in the same manner as that in Step 3 in Example 1.

1H-NMR(300 MHz, DMSO-d6) δ=1.18(9H, s), 4.01(2H, s), 5.35(1H, d, J=4.8 Hz), 5.38(1H, d, J=4.8 Hz), 6.48-6.61 (2H, m), 6.66-6.74(2H, m), 6.85-6.90(1H, m), 7.04(1H, dd, J=8.3 Hz, 1.9 Hz), 7.09(1H, s), 7.35(1H, J=1.9 Hz), 9.32(1H, s). MS(ESI) m/z 366(M−H)⁻.

Example 31

A compound of Example 31 (yield: 56%) was synthesized by using 4-(1,1,3,3-tetramethylbutyl)-2-chlorobenzaldehyde as the starting compound in the same manner as that in Step 3 in Example 1. The starting aldehyde was synthesized from 4-(1,1,3,3-tetramethylbutyl)-phenol in the same manner as that in Step 1 in Example 30.

1H-NMR(300 MHz, DMSO-d6) δ=0.55(9H, s), 1.20(3H, s), 1.24(3H, s), 1.60(2H, s), 4.02(2H, s), 5.23(1H, d, J=4.5 Hz), 5.39(1H, d, J=4.2 Hz), 6.36(1H, d, J=7.5 Hz), 6.50(1H, t, J=7.5 Hz), 6.61(1H, d, J=8.4 Hz), 6.68(1H, t, J=7.5 Hz), 6.84(1H, d, J=8.4 Hz), 7.00(1H, d, J=7.5 Hz), 7.09(1H, s), 7.34(1H, s), 9.28(1H, s). MS(ESI) m/z 422(M−H)⁻.

Example 32

A compound of Example 32 (yield: 64%) was synthesized by using 2-pyridinecarboxaldehyde as the starting compound in the same manner as that in Step 3 in Example 1.

1H-NMR(300 MHz, DMSO-d6) δ=3.98(2H, s), 5.10(1H, d, J=4.5 Hz), 5.84(1H, d, J=4.5 Hz), 6.48-6.59(2H, m), 6.65(1H, t, J=7.5 Hz), 6.83(1H, d, J=7.5 Hz), 6.91(1H, d, J=7.5 Hz), 7.04(1H, s), 7.06-7.13(1H, m), 7.53(1H, t, J=7.5 Hz), 8.39-8.44(1H, m), 9.23(1H, s). MS(ESI) m/z 279(M+H)⁺.

Example 33

A compound of Example 33 (yield: 52%) was synthesized by using 5-bromothiophene-2-carboxyaldehyde as the starting compound in the same manner as that in Step 3 in Example 1.

1H-NMR(300 MHz, DMSO-d6) δ=3.93(2H, s), 5.16(1H, d, J=4.5 Hz), 6.02(1H, d, J=4.5 Hz), 6.61-6.87(5H, m), 6.92(1H, d, J=3.6 Hz), 7.09(1H, s), 9.26(1H, s). MS(ESI) m/z 362, 364(M+H)⁺.

Example 34

(Step 1) Synthesis of 2-phenyl-5-pyrimidinecarboxyaldehyde

A solution of tetrafluoroboric acid salt (4 mmol) of 2-dimethylaminoethylene-1,3-bis(dimethyliminio)propane produced according to a method described in "Synthesis" (1988, p. 641), benzamidine hydrochloride (4 mmol) and sodium ethoxide (12 mmol) in ethanol (5 ml) was stirred at 80° C. for 2 hours. After the extraction with ethyl acetate followed by the purification with the silica gel column chromatography, 2-phenyl-5-pyrimidinecarboxyaldehyde (Yield: 226 mg, 31%) was obtained.

1H-NMR(300 MHz, CDCl3) δ=7.50-7.60(3H, m), 8.54-8.58(2H, m), 9.22(2H, s), 10.16(1H, s).

(Step 2) Synthesis of a Compound of Example 34

The compound of Example 34 (yield: 37%) was synthesized by using 2-phenyl-5-pyrimidinecarboxyaldehyde as the starting compound in the same manner as that in Step 3 in Example 1.

1H-NMR(300 MHz, DMSO-d6) δ=4.02(2H, d, J=4.5 Hz), 5.15(1H, d, J=4.2 Hz), 6.08(1H, d, J=4.2 Hz), 6.60-6.70(2H, m), 6.72-6.78(1H, m), 6.93(1H, d, J=7.8 Hz), 7.16(1H, s), 7.44-7.51(3H, m), 8.25-8.33(2H, m), 8.58(2H, s), 9.38(1H, s). MS(ESI) m/z 354(M−H)⁻.

Example 35

A solution of pyrrolidin-2,4-dione (40 mg, 0.404 mmol) and 4,5-dimethyl-1,2-phenylenediamine (55 mg, 0.404 mmol) in dimethylformamide was stirred in the presence of molecular sieves for 9 hours. 4-Bromobenzaldehyde (75 mg, 0.404 mmol) and acetic acid (0.01 ml) were added to the reaction mixture, and they were stirred at 70° C. overnight. The reaction mixture was filtered. After the addition of water, the crystals thus formed were taken by the filtration and then washed with dichloromethane to obtain the compound of Example 35 (yield: 100 mg, 65%).

1H-NMR (300 MHz, DMSO-d6) δ=1.94(3H, s), 2.01(3H, s), 3.93(2H, s), 4.96(1H, d, J=4.2 Hz), 5.67(1H, d, J=4.2 Hz), 6.29(1H, s), 6.59(1H, s), 6.99(1H, s), 7.04(2H, d, J=7.8 Hz), 7.35(2H, d, J=7.8), 9.08(1H, s). MS(ESI) m/z 382, 384(M−H)⁻.

Example 36

(Step 1) Synthesis of 4-((1R,2R)-(2-aminocyclohexyl)amino)-3-pyrrolin-2-one

A solution of pyrrolidin-2,4-dione (40 mg, 0.404 mmol) and (1R,2R)-1,2-diaminocyclohexanediamine (46 mg, 0.404 mmol) in methanol (2 ml) was stirred at 60° C. for 2 hours. The reaction solution was concentrated. After the purification by the alumina column chromatography, 4-((1R, 2R)-(2-aminocyclohexyl)amino)-3-pyrrolin-2-on (yield: 66 mg, 84%) was obtained.

¹H-NMR (300 MHz, DMSO-d6) δ=1.09-1.91(8H, m), 2.41(1H, m), 2.63(1H, m), 3.17(2H, s), 3.70(1H, d, J=16 Hz), 3.78(1H, d, J=16 Hz), 4.39(1H, s), 6.45(1H, s), 6.61 (1H, d, J=8.1 Hz). MS(ESI) m/z 196(M+H)⁺, 194(M−H)⁻.

(Step 2) Synthesis of a Compound of Example 36

4-((1R,2R)-(2-Aminocyclohexyl)amino)-3-pyrrolin-2-one (66 mg, 0.337 mmol) obtained in step 1 and 4-bromobenzaldehyde (63 mg, 0.337 mmol) were stirred in ethanol at 70° C. overnight. The reaction mixture was concentrated. The diastereomers were separated and purified by the silica gel column chromatography. Diethyl ether was added to the obtained solid. After the filtration followed by the washing, the compound (yield: 12 mg, 10%) of Example 36 was obtained as a compound of a low polarity.

1H-NMR (300 MHz, DMSO-d6) δ=1.17-1.40(4H, m), 1.68-1.74(2H, m), 1.93-1.98(2H, m), 2.63(1H, m), 3.15(1H, m), 3.80(1H, d, J=16.6 Hz), 3.94(1H, d, J=16.6 Hz), 4.62 (1H, s), 7.26(2H, d, J=6.6 Hz), 7.40(2H, d, J=6.6 Hz). MS(ESI) m/z 362, 364(M+H)+.

Example 37

The compound (yield: 15 mg, 12%) of Example 37 was synthesized as a substance of a high polarity in the separation and purification of the diastereomers by the silica gel column chromatography in Step 2 in Example 36.

1H-NMR (300 MHz, DMSO-d6) δ=1.06-1.27(4H, m), 1.47(1H, m), 1.56-1.68(2H, m), 1.90(1H, m), 2.29(1H, m), 3.02(1H, m), 3.90(1H, d, J=16.5 Hz), 4.02(1H, d, J=16.5 Hz), 4.96(1H, s), 7.20(2H, d, J=8.4 Hz), 7.43(2H, d, J=8.4 Hz). MS(ESI) m/z 362, 364(M+H)+.

Compounds of Examples 38 to Example 41 were synthesized by the separation and purification of the diastereomers by the silica gel column chromatography in the same manner as that of Example 37 except that the starting compound was replaced with a corresponding aldehyde.

Example 42

(Step 1) Synthesis of 10-(4-bromophenyl)-1,2,3,4,9,10-tetrahydro-benzo[b]pyrrolo[3,4-e][1,4]dizepin-1-one 10-(4-Bromophenyl)-1,2,3,4,9,10-tetrahydro-benzo[b]pyrrolo[3,4-e][1,4]dizepin-1-one (yield: 95%) was synthesized in the same manner as that in Step 3 in Example 1 except that 4-bromobenzaldehyde was used as the starting compound.

1H-NMR(300 MHz, DMSO-d6) δ=3.97(2H, s), 5.03(1H, d, J=4.2 Hz), 5.89(1H, d, J=4.5 Hz), 6.51(1H, dd, J=8.1, 1.5 Hz), 6.59(1H, dt, J=7.5, 1.5 Hz), 6.68(1H, dt, J=8.4, 2.1 Hz), 6.83(1H, dd, J=7.5, 1.5 Hz), 7.06(1H, s), 7.13(2H, d, J=6.6 Hz), 7.36(2H, d, J=6.6 Hz), 9.22(1H, s). MS(ESI) m/z 356, 358(M+H)+.

(Step 2) Synthesis of a Compound in Example 42

The compound (40 mg, 0.11 mmol) obtained in Step 1 and methyl iodide (0.137 ml, 2.2 mmol) were stirred in the presence of triethylamine (0.023 ml, 0.17 mmol) in methanol for 4 hours. After the completion of the reaction, the product was purified by the silica gel chromatography. Diethyl ether was added to the obtained solid. After the filtration followed by the washing, the compound of Example 42 (yield: 5 mg, 12%) was obtained.

1H-NMR (300 MHz, DMSO-d6) δ=2.51(3H, s), 3.97(1H, d, J=17 Hz), 3.99(1H, d, J=17 Hz), 4.90(1H, s), 6.44(1H, d, J=8.4 Hz), 6.71(1H, t, J=6.9 Hz), 6.82-6.94(4H, m), 7.10 (1H, s), 7.16-7.34(2H, m), 9.27(1H, s). MS(ESI) m/z 368, 370(M-H)-.

Example 43

Acetic anhydride (0.05 ml, 0.56 mmol) was added to a solution of the compound (50 mg, 0.14 mmol) obtained in Step 1 in Example 42 in pyridine, and they were stirred for 5 hours. The reaction mixture was concentrated. Diethyl ether was added to the obtained solid. After the filtration followed by the washing, the compound of Example 43 (yield: 43 mg, 77%) was obtained.

1H-NMR (300 MHz, DMSO-d6) δ=1.70(3H, s), 4.03(2H, s), 6.77-6.79(2H, m), 6.85(1H, s), 6.95(1H, d, J=8.4 Hz), 7.04(1H, m), 7.16(1H, m), 7.36-7.39(4H, m), 9.50(1H, s). MS(ESI) m/z 396, 398(M-H)-.

Example 44

A compound (yield: 41%) of Example 44 was synthesized in the same manner as that of Example 1 except that 1,2-phenylenediamine was replaced with N-methyl-1,2-phenylenediamine in Step 2 in Example 1 and that 4-bromobenzaldehyde was used as the starting material in Step 3 in Example 1.

1H-NMR (300 MHz, DMSO-d6) δ=3.34(3H, s), 4.11(1H, d, J=18 Hz), 4.30(1H, d, J=18 Hz), 5.04(1H, d, J=4 Hz), 5.68(1H, d, J=4 Hz), 6.43(1H, dd, J=7.8, 1.5 Hz), 6.68(1H, d, J=7.2 Hz), 6.81-7.10(3H, m), 7.28-7.39(3H, m), 9.28(1H, s). MS(ESI) m/z 368, 370(M-H)-.

The chemical structures of the compounds produced in Examples 1 to 44 are as follows:

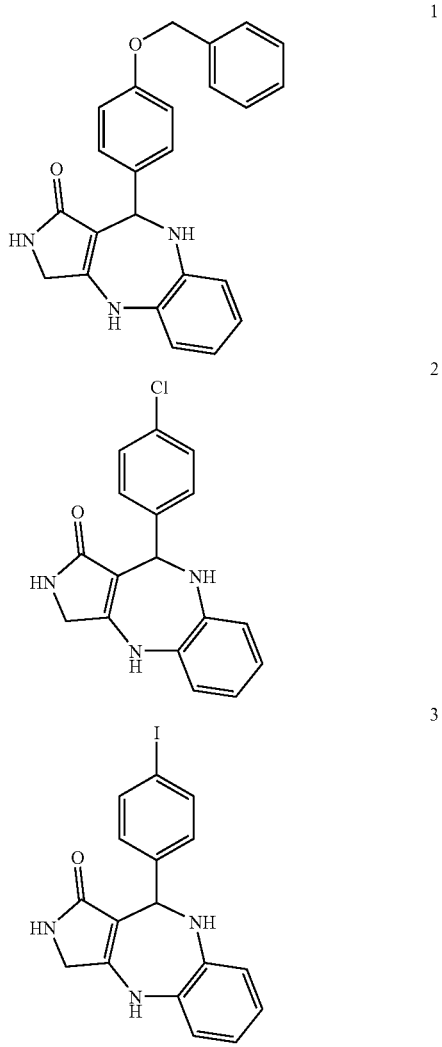

-continued
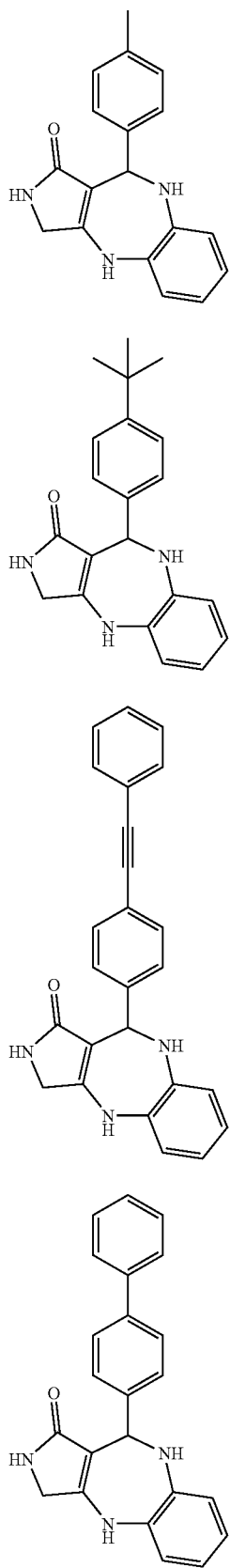
-continued
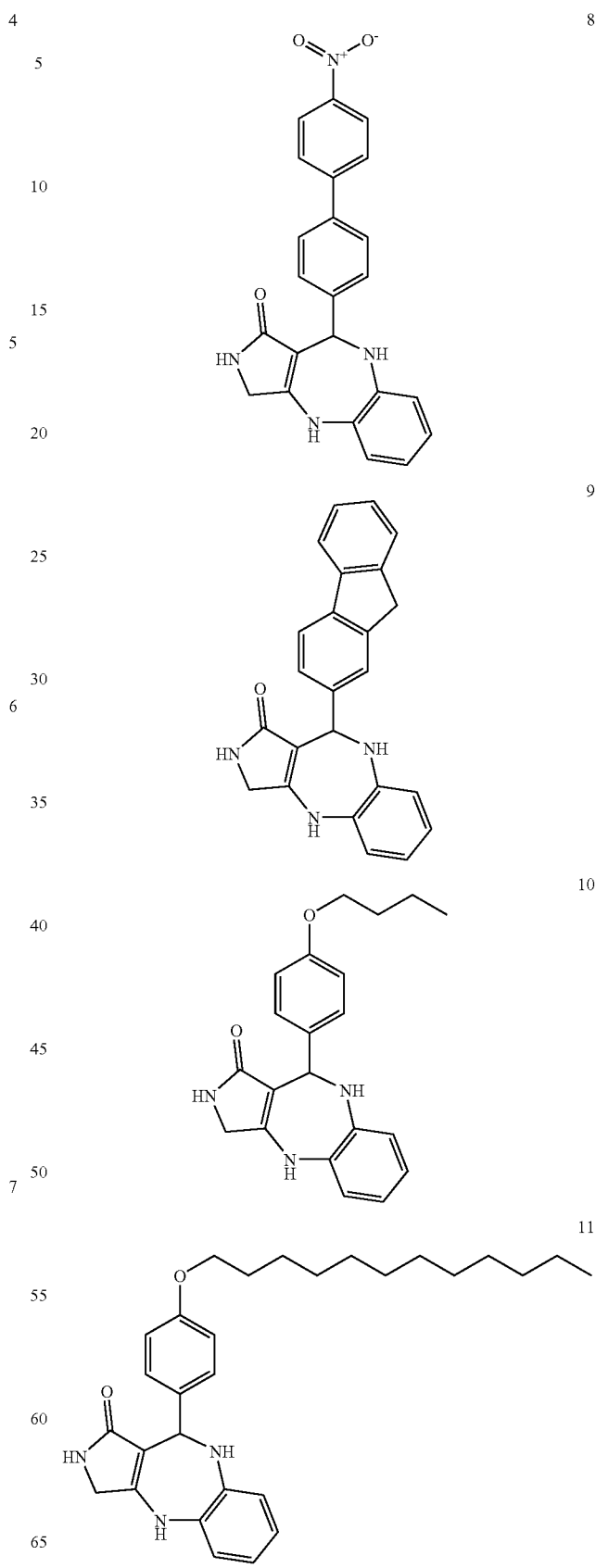

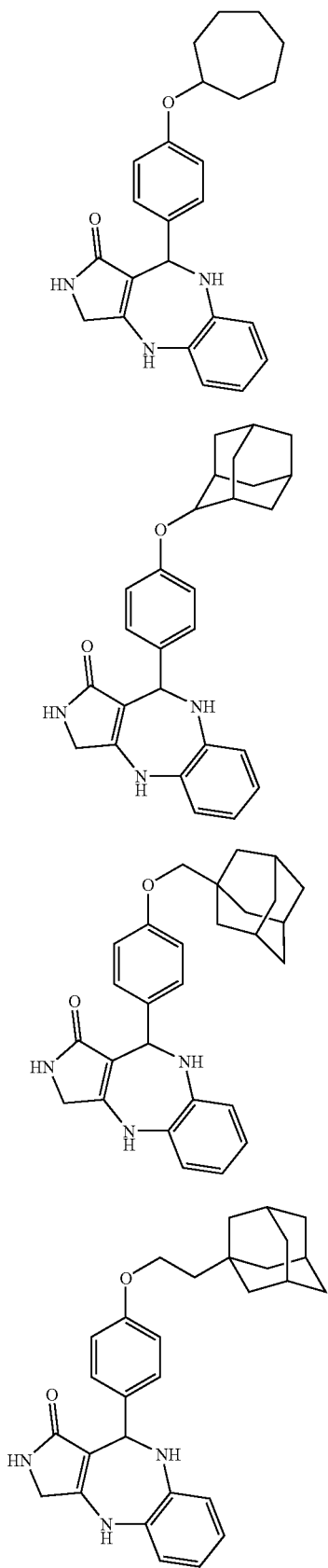
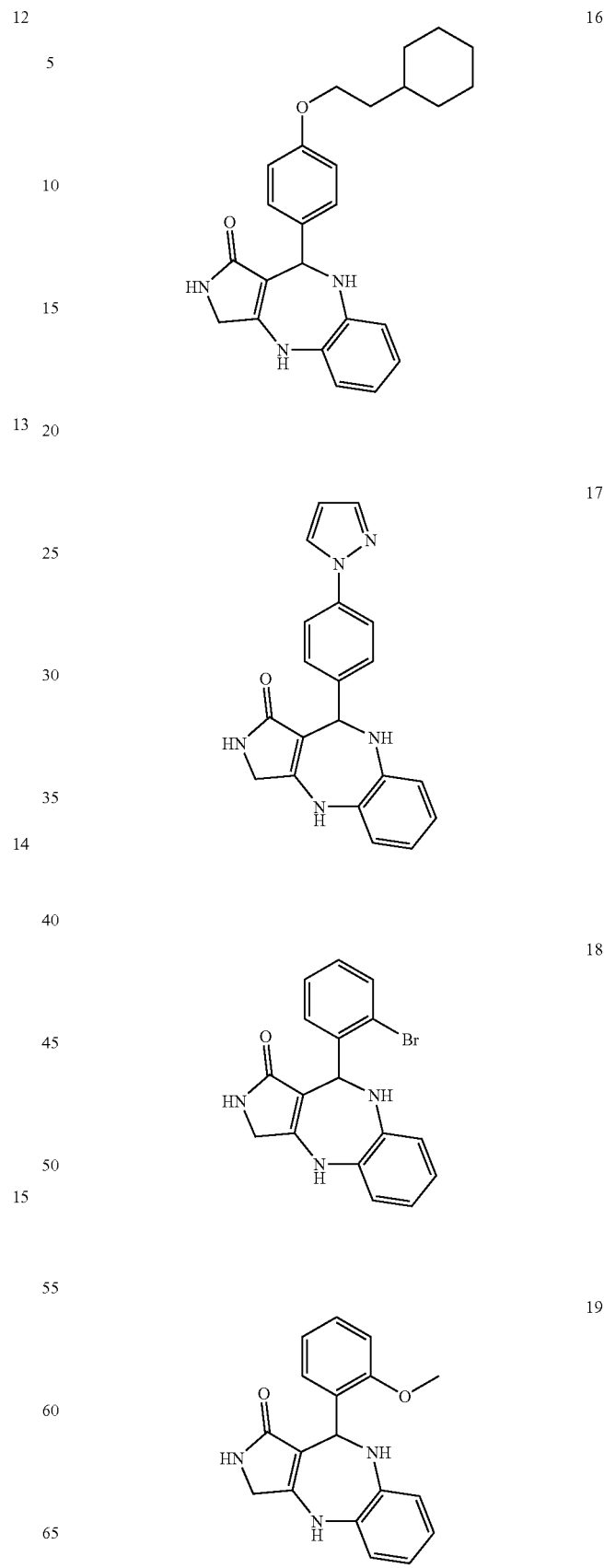

-continued
20
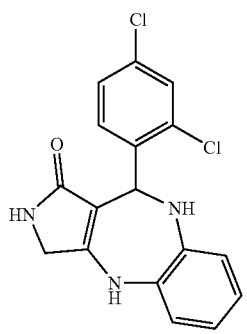
21
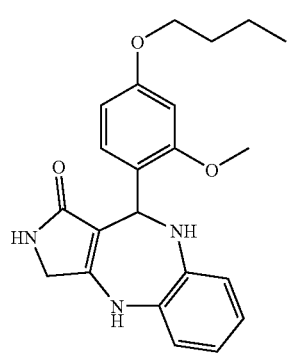
22
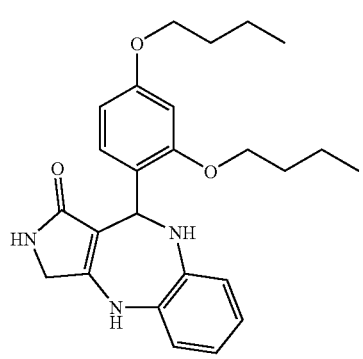
23
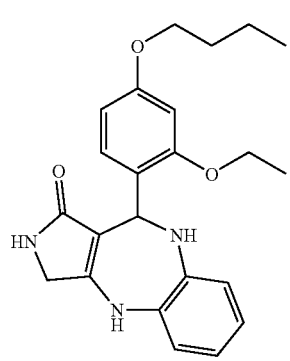
-continued
24
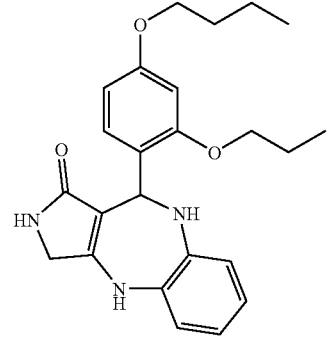
25
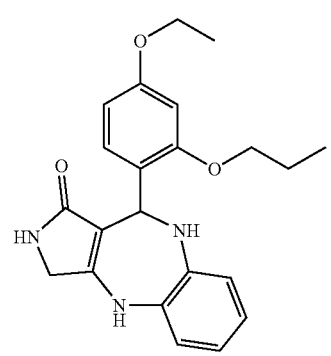
26
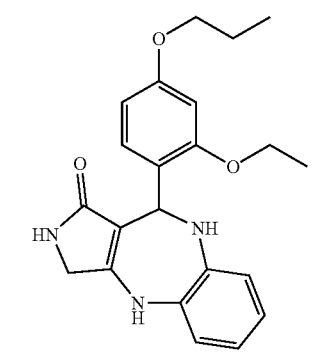
27
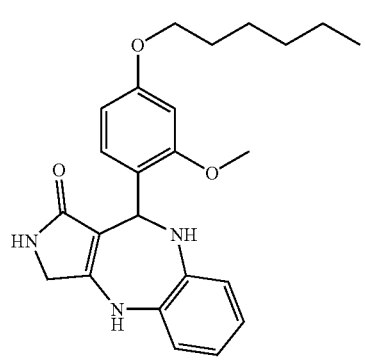

-continued
28
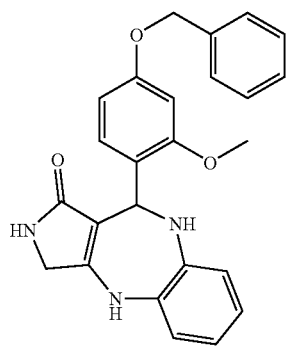
29
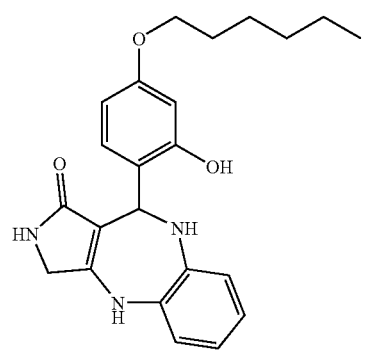
30
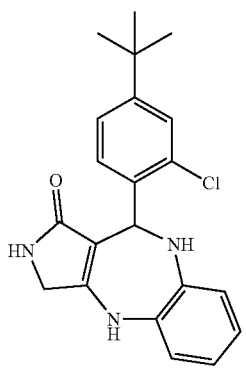
31
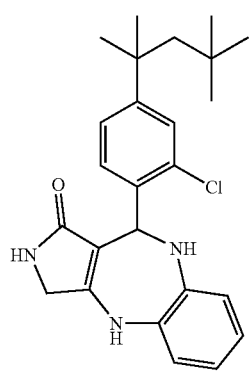
-continued
32
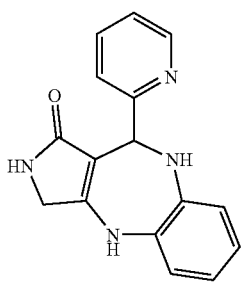
33
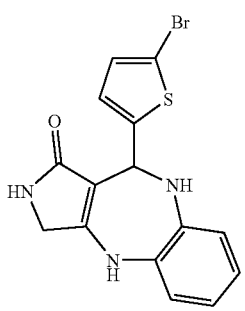
34
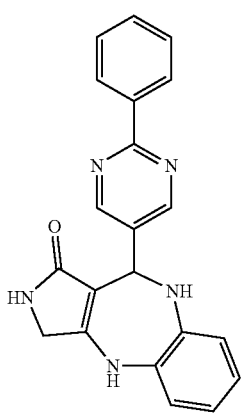
35
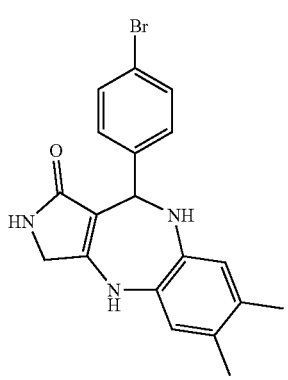

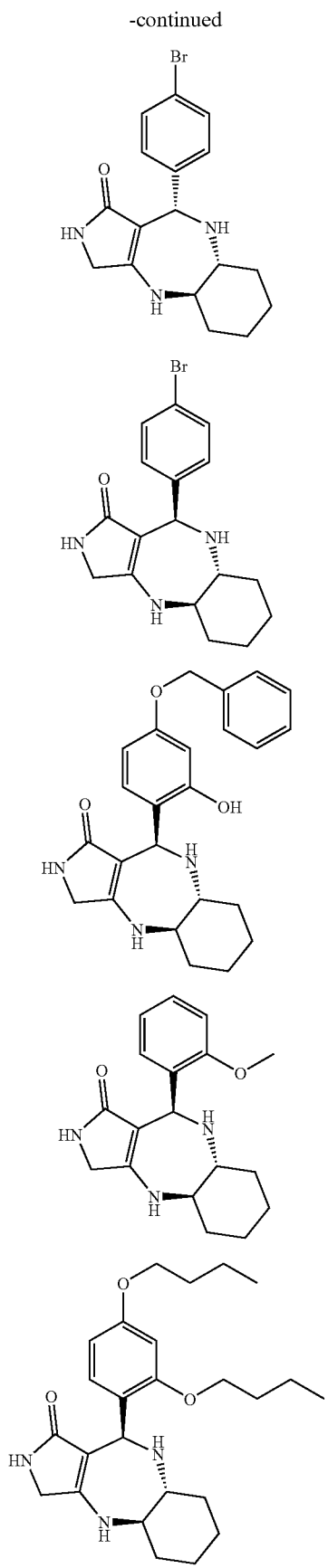
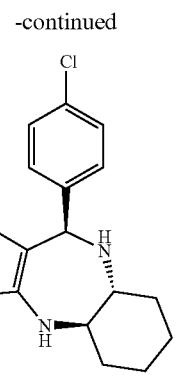
In Examples 45 to 177, the compounds were synthesized by a method that comprises reacting an enamine compound (IX) with a corresponding aldehyde to produce a cyclic compound (X) and alkylating or acylating the compound (X) as shown below:

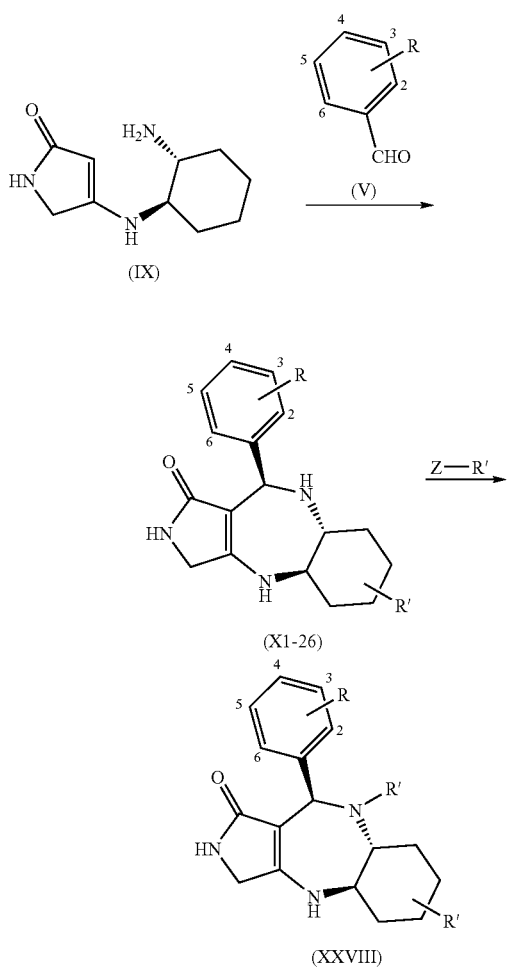

wherein R represents a substituent on the benzene ring, R' represents a substituent on nitrogen atom at the 9-position, and Z represents a halogen atom or the like.

Example 45

(Step 1) Process for producing cyclic compound (X1) (R=2-OMe)

0.5 ml of acetic acid was added to a solution of 4-((1R, 2R)-(2-aminocyclohexyl)amino)-3-pyrrolin-2-on (9.75 g, 50 mmol) obtained in Step 1 in Example 36 and 2-methoxybenzaldehyde (7.48 g, 55 mmol) in methanol (150 ml), and they were stirred at 65° C. overnight. The reaction mixture was concentrated, and 90 ml of a mixed solvent of ether/dichloromethane (1/1) was added to the resultant crystals. After the through stirring, the solid was taken by the filtration to obtain the cyclic compound (XI) (R=2-OMe) in the form of a white solid (8.80 g, 56%). This compound was the same as that obtained in Example 39.

(Step 2) Process for Producing Compound of Example 45 (R=2-OMe, R'=COCH$_3$)

Production process A (acid anhydride process): Triethylamine (5.05 g, 50 mmol) was added to a solution of the cyclic compound (X1) (R=2-OMe) (3.13 g, 10 mmol) obtained in Step 1 in Example 45 in dichloromethane (200 ml). Then acetic anhydride (4.08 g, 40 mmol) was added to the obtained mixture, and they were stirred at 45° C. for 4 hours. After cooling to ambient temperature, the crystals thus formed were taken by the filtration to obtain the compound of Example 45 as a white solid (1.96 g, 55%).

Compounds in Examples 46 to 177 were produced in the same manner as that in Steps 1 and 2 in Example 45.

In step 2, the compound was synthesized by above-described production process A or by any of the following production processes B to F:

Production process B (acid chloride method): A solution of a cyclic compound (X) (0.33 mmol) and triethylamine (0.77 mmol) in dichloromethane (15 ml) was cooled to 0° C. A corresponding acid chloride (1.28 mmol) was added thereto, and they were stirred at room temperature for 15 hours. After the distillation of the solvent, the obtained product was purified by the silica gel TLC chromatography to obtain an acylated compound (XXVIII).

Production process C (mixed acid anhydride method): Triethylamine (10 mmol) was added to a solution of a corresponding carboxylic acid (11 mmol) in anhydrous tetrahydrofuran (50 ml), and they were cooled at −15° C. Ethyl chloroformate (10 mmol) was added to the reaction mixture to form a white solid. They were stirred for 15 minutes. Then a solution of a cyclic compound (X) (2 mmol) in dichloromethane (60 ml) was added to the reaction mixture, and they were stirred at room temperature for 2 hours. After the evaporation of the solvent followed by the extraction with dichloromethane, the product was purified by the silica gel column chromatography to obtain an acylated compound (XXVIII).

Production process D (WSC condensation method): A solution of a cyclic compound (X) (0.25 mmol) in dichloromethane (10 ml) was cooled at 0° C. A corresponding carboxylic acid (1 mmol) and WSC (1-ethyl-3-(3-dimethylaminopropyl)carbodiimide hydrochloride) (1 mmol) were added to the solution, and they were stirred at room temperature for 15 hours. The solvent was evaporated, and the product was purified by the silica gel thin-layer chromatography to obtain an acylated compound (XXVIII).

Production process E (isocyanate addition method): A corresponding isocyanate (1.5 mmol) was added to a solution of a cyclic compound (X) (0.3 mmol) in dichloromethane (10 ml), and they were stirred at room temperature for 24 hours. The solvent was evaporated, and the product was purified by the silica gel thin-layer chromatography to obtain an acylated compound (XXVIII).

Production process F (diketene addition method): A diketene (10 mmol) was added to a solution of a cyclic compound (X) (1 mmol) in ethanol (10 ml), and they were heated at 70° C. for 4 hours. The solvent was evaporated, and the product was purified by the silica gel thin-layer chromatography to obtain an acylated compound (XXVIII).

The chemical structural formulae of the cyclic compounds (X1-26) produced in Step 1 and the data of the compounds are shown in Tables 1.

TABLE 1-1

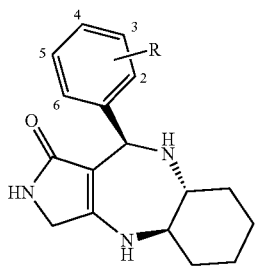

| Co | R | D |
|---|---|---|
| X1 | 2-OMe | MS: 312(M − H)−, N1: 1.07-2.82(10H, m), 3.73(1H, d, J=16.5 Hz), 3.81(1H, d, J=16.5 Hz), 3.84(3H, s), 5.01(1H, s), 6.29(1H, s), 6.66(1H, s), 6.79-7.19(4H, m) |
| X2 | 2-OEt | MS: 327(M + H)+, N1: 1.07-2.82(10H, m), 1.38(3H, t, J=7.2 Hz), 3.73(1H, d, J=16.5 Hz), 3.81(1H, d, J=16.5 Hz), 4.10(2H, m), 5.01(1H, s), 6.29(1H, s), 6.65(1H, s), 6.79-7.19(4H, m) |
| X3 | 2-OCHMe$_2$ | MS: 342(M + H)+, N1: 1.07-2.82(17H, m), 3.71(1H, d, J=16.2 Hz), 3.81(1H, d, J=16.2 Hz), 4.99(1H, s), 6.27(1H, s), 6.66(1H, s), 6.70-7.20(4H, m) |
| X4 | 2-OCH$_2$Ph | MS: 390(M + H)+, N1: 0.50-3.40(10H, m), 3.68(1H, d, J=16.2 Hz), 3.82(1H, d, J=16.2 Hz), 5.05(1H, s), 5.13(1H, d, J=15.0 Hz), 5.18(1H, d, J=15.0 Hz), 6.27(1H, s), 6.65(1H, s), 6.78-6.84(2H, m), 7.04-7.22(2H, m), 7.29-7.52(5H, m) |
| X5 | 2-OCF$_3$ | MS: 368(M + H)+, N1: 0.50-3.40(10H, m), 3.70(1H, d, J=16.0 Hz), 3.83(1H, d, J=16.0 Hz), 5.06(1H, s), 6.39(1H, s), 6.72(1H, s), 7.00-7.07(1H, m), 7.18-7.37(3H, m) |
| X6 | 2-OMe-4-F | MS: 332(M + H)+, N1: 0.85-3.48(10H, m), 3.70(1H, d, J=16.8 Hz), 3.83(1H, d, J=16.8 Hz), 3.85(3H, s), 4.95(1H, s), 6.32(1H, s), 6.58-6.66(1H, m), 6.68(1H, s), 6.74-6.82(1H, m), 6.84-6.92(1H, m) |
| X7 | 2-OMe-4-Cl | MS: 348(M + H)+, N1: 3.83(1H, d, J=16.8 Hz), 3.85(3H, s), 4.95(1H, s), 6.32(1H, s), 6.58-6.66(1H, m), 6.68(1H, s), 6.74-6.82(1H, m), 6.84-6.92(1H, m) |
| X8 | 2-OMe-4-CH$_2$Ph | MS: 420(M + H)+, N1: 0.50-3.40(10H, m), 3.67(1H, d, J=16.2 Hz), 3.79(1H, d, J=16.2 Hz), 3.80(3H, s), 4.91(1H, s), 5.04(2H, s), 6.23(1H, s), 6.40-6.70(4H, m), 7.28-7.48(5H, m) |

TABLE 1-2

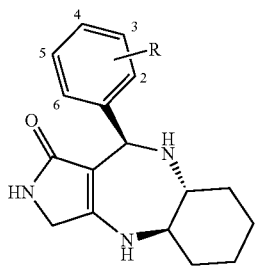

| Co | R | D |
|---|---|---|
| X9 | 2-OMe-5-F | MS: 332(M + H)+, N1: 0.50-3.40(10H, m), 3.70(1H, d, J=16.2 Hz), 3.82(3H, s), 3.85(1H, d, J=16.2 Hz), 4.96(1H, s), 6.37(1H, s), 6.48-7.02(4H, m) |
| X10 | 2,3-(OMe)$_2$ | MS: 344(M + H)+, N1: 0.50-3.40(10H, m), 3.68(1H, d, J=16.0 Hz), 3.72-3.83(7H, m), 5.04(1H, s), 6.27(1H, s), 6.42-6.50(1H, m), 6.66(1H, s), 6.82-6.94(2H, m) |
| X11 | 2,4-(OMe)$_2$ | MS: 344(M + H)+, N1: 0.50-3.40(10H, m), 3.60-3.88(2H, m), 3.71(3H, s), 3.80(3H, s), 4.93(1H, s), 6.20-6.40(2H, m), 6.51-6.58(1H, m), 6.62-6.73(2H, m) |

TABLE 1-2-continued

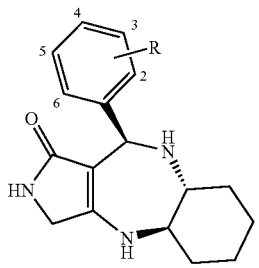

| Co | R | D |
|---|---|---|
| X12 | 2,5-(OMe)₂ | MS: 344(M + H)+, N1: 0.50-3.40(10H, m), 3.62(3H, s), 3.68(1H, d, J=16.0 Hz), 3.77(3H, s), 3.81(1H, d, J=16.0 Hz), 4.94(1H, s), 6.28(1H, s), 6.32(1H, d, J=3.0 Hz), 6.66(1H, s), 6.72(1H, dd, J=3.0, 8.7 Hz), 6.88(1H, d, J=8.7 Hz) |
| X13 | 2-Me | MS: 298(M + H)+, N1: 0.50-3.40(10H, m), 2.41(3H, s), 3.68(1H, d, J=16.0 Hz), 3.82(1H, d, J=16.0 Hz), 4.91(1H, s), 6.24(1H, s), 6.67(1H, s), 6.83-7.17(4H, m) |
| X14 | 2-Et | MS: 312(M + H)+, N1: 0.50-3.40(12H, m), 1.23(3H, t, J=7.5 Hz), 3.68(1H, d, J=16.5 Hz), 3.82(1H, d, J=16.5 Hz), 5.02(1H, s), 6.23(1H, s), 6.67(1H, s), 6.85-7.17(4H, m) |
| X15 | 2-CHMe₂ | MS: 326(M + H)+, N1: 0.50-3.60(15H, m), 3.68(1H, d, J=16.0 Hz), 3.82(1H, d, J=16.0 Hz), 5.10(1H, s), 6.25(1H, s), 6.70(1H, s), 6.80-7.30(4H, m) |
| X16 | 2-Br | MS: 362, 364(M + H)+, N1: 0.50-3.60(10H, m), 3.72(1H, d, J=16.0 Hz), 3.83(1H, d, J=16.0 Hz), 4.97(1H, s), 6.42(1H, s), 6.73(1H, s), 6.95-7.03(1H, m), 7.10-7.29(2H, m), 7.56-7.63(1H, m) |

TABLE 1-3

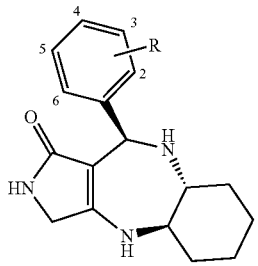

| Co | R | D |
|---|---|---|
| X17 | 2-Cl | MS: 318(M + H)+, N1: 0.50-3.40(10H, m), 3.71(1H, d, J=16.2 Hz), 3.83(1H, d, J=16.2 Hz), 5.04(1H, s), 6.41(1H, s), 6.72(1H, s), 6.96-7.02(1H, m), 7.16-7.26(2H, m), 7.39-7.44(1H, m) |
| X18 | 2-F | MS: 302(M + H)+, N1: 0.50-3.40(10H, m), 3.71(1H, d, J=16.2 Hz), 3.83(1H, d, J=16.2 Hz), 5.07(1H, s), 6.39(1H, s), 6.72(1H, s), 6.90-7.30(4H, m) |
| X19 | 2-CF₃ | MS: 352(M + H)+ |
| X20 | H | MS: 284(M + H)+, N1: 0.50-3.40(10H, m), 3.69(1H, d, J=16.0 Hz), 3.84(1H, d, J=16.0 Hz), 4.79(1H, s), 6.32(1H, s), 6.75(1H, s), 7.10-7.30(5H, m) |
| X21 | 2-NO₂ | MS: 329(M + H)+, N1: 0.50-3.40(10H, m), 3.71(1H, d, J=16.2 Hz), 3.79(1H, d, J=16.2 Hz), 5.30(1H, s), 6.43(1H, s), 6.80(1H, s), 7.06-7.13(1H, m), 7.38-7.56(2H, m), 7.70-7.78(1H, m) |
| X22 | 3-Cl | MS: 318(M + H)+, N1: 0.50-3.40(10H, m), 3.69(1H, d, J=16.2 Hz), 3.83(1H, d, J=16.2 Hz), 4.70(1H, s), 6.32(1H, s), 6.73(1H, s), 7.16-7.30(4H, m) |

TABLE 1-3-continued

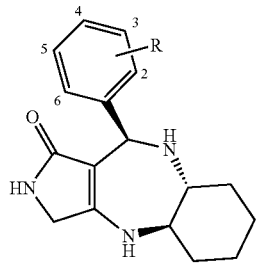

| Co | R | D |
|---|---|---|
| X23 | 4-OMe | MS: 312(M − H)−, N1: 0.50-3.40(10H, m), 3.60-3.72(4H, m), 3.79(1H, d, J=16.2 Hz), 4.66(1H, s), 6.19(1H, s), 6.65(1H, s), 6.78(2H, d, J=8.4 Hz), 7.10(2H, d, J=8.4 Hz) |
| X24 | 4-Br | MS: 362, 364(M + H)+, N1: 1.06-1.27(4H, m), 1.47(1H, m), 1.56-1.68(2H, m), 1.90(1H, m), 2.29(1H, m), 3.02(1H, m), 3.90(1H, d, J=16.5 Hz), 4.02(1H, d, J=16.5 Hz), 4.96(1H, s), 7.20(2H, d, J=8.4 Hz), 7.43(2H, d, J=8.4 Hz) |
| X25 | 4-Cl | MS: 315(M − H)−, N1: 1.01-1.10(4H, m), 1.41-1.52(3H, m), 1.85(1H, m), 2.02(1H, m), 2.80(1H, m), 3.70(1H, d, J=16.5 Hz), 3.83(1H, d, J=16.5 Hz), 4.71(1H, s), 6.30(1H, s), 6.72(1H, s), 7.23(2H, d, J=8.7 Hz), 7.30(2H, d, J=8.7 Hz) |
| X26 | 2-SMe | MS: 330(M + H)+, N1: 0.50-2.90(10H, m), 2.48(3H, s), 3.70(1H, J=16.0 Hz, d), 3.83(1H, J=16.0 Hz, d), 5.01(1H, s), 6.32(1H, s), 6.68(1H, s), 6.82-6.90(1H, m), 6.97-7.06(1H, m), 7.15-7.24(1H, m), 7.26-7.33(1H, m) |

The chemical structural formulae of the compounds obtained in Step 2 in Examples 46 to 177, the acylation process in Step 2 and the data of the compounds are shown in Tables 2-1 to 2-10.

TABLE 2-1

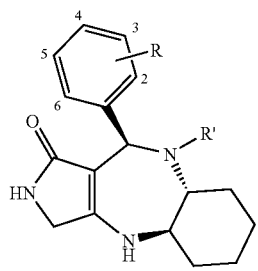

| No. | R | R' | S | D |
|---|---|---|---|---|
| 45 | 2-OMe | COCH$_3$ | A | MS: 354(M − H)−, N1: 0.90-1.97(8H, m), 2.12(3H, s), 2.82(1H, m), 3.74-3.84(5H, m), 3.99(1H, m), 5.74(1H, s), 6.66(1H, s), 6.91(1H, d, J=6.9 Hz), 6.99-7.33(4H, m), [α]D=−129.6° (c = 0.24, MeOH) |
| 46 | 2-OMe | COCH$_2$CH$_3$ | A | MS: 370(M + H)+, N1: 0.50-3.40(9H, m), 0.98(3H, t, J=7.2 Hz), 2.24-2.38(1H, m), 2.60-2.76(1H, m), 3.79(3H, s), 3.68-3.87(2H, m), 3.92-4.05(1H, m), 5.80(1H, s), 6.62(1H, s), 6.70(1H, s), 6.84-7.34(4H, m) |
| 47 | 2-OMe | COCH$_2$CH$_2$CH$_3$ | A | MS: 382(M − H)− |
| 48 | 2-OMe | COCF$_3$ | A | MS: 408(M − H)− |
| 49 | 2-OMe | COCH$_2$CF$_3$ | D | MS: 424(M + H)+, N1: 0.50-3.40(9H, m), 3.84(3H, s), 3.55-3.90(4H, m), 3.93-4.06(1H, m), 5.62(1H, s), 6.73(1H, s), 6.78(1H, s), 6.90-7.36(4H, m) |
| 50 | 2-OMe | COCF$_2$CF$_3$ | A | MS: 460(M + H)+, N1: 0.50-3.40(9H, m), 3.79(3H, s), 3.76-3.95(3H, m), 6.08(1H, s), 6.83(1H, s), 6.86(1H, s), 6.90-7.40(4H, m) |
| 51 | 2-OMe | COCH$_2$OH | *1 | MS: 370(M − H)−, N1: 0.73-3.07(9H, m), 3.88-4.22(8H, m), 5.73(1H, s), 6.93(1H, m), 7.10-7.12(3H, m), 7.32-7.35(2H, m) |
| 52 | 2-OMe | COCH$_2$OAc | C | MS: 412(M − H)−, N1: 0.65-2.95(12H, m), 3.81-3.93(6H, m), 4.65(1H, d, J=15 Hz), 5.25(1H, d, J=15 Hz), 5.61(1H, s), 6.80(2H, m), 6.98(1H, m), 7.06-7.12(2H, m), 7.35-7.41(1H, m) |

TABLE 2-2

| No. | R | R' | S | D |
|---|---|---|---|---|
| 53 | 2-OMe | COCH$_2$OMe | C | MS: 386(M + H)+, <br> N1: 0.50-3.40(9H, m), 3.31(3H, s), 3.72-3.88(2H, m), 3.84(3H, s), 3.94-4.04(1H, m), 4.08(1H, d, H=14.4 Hz), 4.34(1H, d, J=14.4 Hz), 5.58(1H, s), 6.69(1H, s), 6.73(1H, s), 6.88-7.34(4H, m) |
| 54 | 2-OMe | COCH$_2$OEt | C | MS: 398(M − H)− |
| 55 | 2-OMe | COCH$_2$OPh | C | MS: 446(M − H)− |
| 56 | 2-OMe | COCH$_2$Ph | C | MS: 430(M − H)− |
| 57 | 2-OMe | COCH=CHPh | C | MS: 442(M − H)− |
| 58 | 2-OMe | COC≡CPh | C | MS: 440(M − H)− |
| 59 | 2-OMe | COCH=CHCH$_3$ | C | MS: 380(M − H)−, <br> N1: 0.77-3.08(12H, m), 3.85(3H, s), 3.97(1H, d, J=17 Hz), 3.97(1H, d, J=17 Hz), 4.23(1H, m), 6.22(1H, s), 6.87-7.13(4H, m) |
| 60 | 2-OMe | COCH$_2$CH$_2$COOMe | C | MS: 428(M + H)+ |
| 61 | 2-OMe | COCH$_2$CH$_2$COOH | *2 | MS: 412(M − H)− |
| 62 | 2-OMe | COCH$_2$CH$_2$CH$_2$OH | *3 | MS: 400(M + H)+ |
| 63 | 2-OMe | COCH$_2$NHZ | C | MS: 503(M − H)− |
| 64 | 2-OMe | COCH$_2$NH$_2$ | *4 | MS: 369(M − H)− |
| 65 | 2-OMe | COCH$_2$CH$_2$NHZ | C | MS: 519(M + H)+ |
| 66 | 2-OMe | COCH$_2$CH$_2$NH$_2$ | *5 | MS: 384(M − H)−, <br> N1: 0.67-3.32(13H, m), 3.75-3.86(6H, m), 6.19(1H, s), 6.53(1H, m), 6.66(1H, m), 6.87(1H, m), 6.93-6.99(2H, m), 7.26(1H, m) |
| 67 | 2-OMe | COCH$_2$CH$_2$OMe | C | MS: 400(M + H)+ |
| 68 | 2-OMe | COCH$_2$CH$_2$Ph | C | MS: 444(M − H)−, <br> N1: 0.88-2.97(13H, m), 3.71-3.86(5H, m), 4.07(1H, m), 5.83(1H, d, J=5.4 Hz), 6.68-6.78(1H, m), 6.88-7.03(3H, m), 7.17-7.34(7H, m) |

TABLE 2-3

| No. | R | R' | S | D |
|---|---|---|---|---|
| 69 | 2-OMe | COCH$_2$CH$_2$-(2-OMe—Ph) | C | MS: 476(M + H)+ |
| 70 | 2-OMe | COCH$_2$CH$_2$-(3,4-F$_2$—Ph) | C | MS: 482(M + H)+ |
| 71 | 2-OMe | COCH$_2$CH$_2$SMe | C | MS: 414(M − H)− |
| 72 | 2-OMe | COCH$_2$COCH$_3$ | F | MS: 398(M + H)+ |
| 73 | 2-OMe | COCH$_2$COOEt | B | MS: 428(M + H)+ |

TABLE 2-3-continued

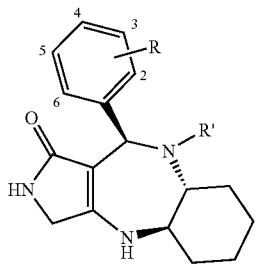

| No. | R | R' | S | D |
|---|---|---|---|---|
| 74 | 2-OMe | COCOOEt | B | MS: 412(M − H)− |
| 75 | 2-OMe | COPh | C | MS: 416(M − H)− |
| 76 | 2-OMe | CO-2-pyridyl | C | MS: 417(M − H)−, N1: 0.95-2.99(9H, m), 3.68(3H, s), 3.83-3.85(2H, m), 4.08(1H, m), 5.56(1H, s), 6.65-6.71(2H, m), 6.83-7.01(3H, m), 7.25(1H, m), 7.37-7.42(2H, m), 7.90(1H, m), 8.50(1H, m) |
| 77 | 2-OMe | CO-3-pyridyl | C | MS: 417(M − H)− |
| 78 | 2-OMe | CO-4-pyridyl | C | MS: 417(M − H)− |
| 79 | 2-OMe | CO-2-pyrazyl | C | MS: 418(M − H)− |
| 80 | 2-OMe | COOMe | B | MS: 370(M − H)− |
| 81 | 2-OMe | COOEt | B | MS: 384(M − H)−, N1: 0.98-3.08(13H, m), 3.68-4.20(7H, m), 6.43(1H, s), 6.67-7.39(4H, m) |
| 82 | 2-OMe | COOCH$_2$Ph | B | MS: 446(M − H)− |
| 83 | 2-OMe | COOPh | B | MS: 432(M − H)− |
| 84 | 2-OMe | CONHEt | E | MS: 383(M − H)−, N1: 0.76-3.20(14H, m), 3.89-3.96(5H, m), 4.21(1H, m), 5.88(1H, s), 6.26(1H, s), 6.89-7.12(3H, m), 7.30(1H, m) |
| 85 | 2-OMe | CONHCH$_2$CH$_2$CH$_3$ | E | MS: 399(M + H)+ |

TABLE 2-4

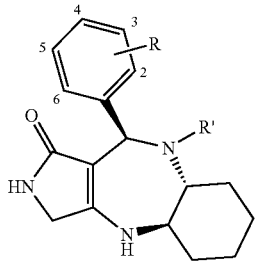

| No. | R | R' | S | D |
|---|---|---|---|---|
| 86 | 2-OMe | SO$_2$CH$_3$ | B | MS: 432(M + CH3CN1 + H)+, N1: 0.73-2.90(9H, m), 3.26(3H, s), 3.67-3.84(6H, m), 5.02(1H, s), 6.30(1H, s), 6.68(1H, s), 6.81-6.83(2H, m), 7.00(1H, m), 7.18(1H, m) |
| 87 | 2-OEt | COCH$_3$ | A | MS: 370(M + H)+ |
| 88 | 2-OEt | COCH$_2$CH$_3$ | A | MS: 382(M − H)−, N1: 0.57-3.42(17H, m), 3.75(1H, d, J=17 Hz), 3.83(1H, d, J=17 Hz), 3.97-4.14(3H, m), 5.81(1H, s), 6.64(1H, s), 6.72(1H, s), 6.88(1H, m), 6.98-7.01(2H, m), 7.27(1H, m) |
| 89 | 2-OEt | COCH$_2$CH$_2$CH$_3$ | A | MS: 398(M + H)+, N1: 0.61-2.82(19H, m), 3.79(2H, d, J=26, 18 Hz), 4.02-4.11(3H, m), 5.81(1H, s), |

TABLE 2-4-continued

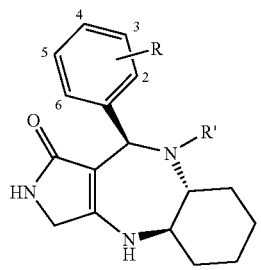

| No. | R | R' | S | D |
|---|---|---|---|---|
| | | | | 6.63(1H, s), 6.71(1H, s), 6.88(1H, m), 6.98-7.01(2H, m), 7.27(1H, m) |
| 90 | 2-OEt | COCF₃ | A | MS: 424(M + H)+ |
| 91 | 2-OEt | COCH₂OAc | C | MS: 428(M + H)+ |
| 92 | 2-OEt | COCH₂OH | *6 | MS: 386(M + H)+ |
| 93 | 2-OEt | COCH₂OMe | C | MS: 400(M + H)+ |
| 94 | 2-OEt | COCH₂OEt | C | MS: 414(M + H)+ |
| 95 | 2-OEt | COOMe | B | MS: 384(M − H)−, N1: 0.62-3.42(12H, m), 3.61(3H, s), 3.71-4.06(5H, m), 6.16(1H, s), 6.56(1H, s), 6.69(1H, s), 6.85(1H, m), 6.93-6.97(2H, m), 7.24(1H, m) |
| 96 | 2-OEt | COOEt | B | MS: 400(M + H)+ |
| 97 | 2-OEt | CONHEt | E | MS: 399(M + H)+ |
| 98 | 2-OCHMe₂ | COCH₃ | A | MS: 384(M + H)+ |

TABLE 2-5

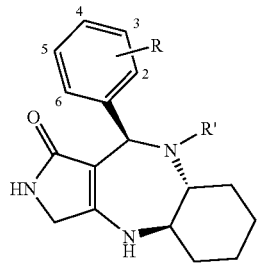

| No. | R | R' | S | D |
|---|---|---|---|---|
| 99 | 2-OCHMe₂ | COCH₂CH₃ | A | MS: 398(M + H)+, N1: 0.95-3.32(20H, m), 3.77-3.85(2H, m), 3.99(1H, m), 4.71(1H, m), 5.78(1H, m), 6.62(1H, s), 6.71(1H, s), 6.84(1H, m), 6.98-7.03(2H, m), 7.25(1H, m) |
| 100 | 2-OCHMe₂ | COCH₂OEt | C | MS: 428(M + H)+, N1: 0.62-3.51(20H, m), 3.74(1H, d, J=16 Hz), 3.83(1H, d, J=16 Hz), 3.97(1H, m), 4.17(1H, d, J=18 Hz), 4.36(1H, d, J=18 Hz), 4.73(1H, m), 5.58(1H, s), 6.66(1H, s), 6.74(1H, s), 6.85(1H, m), 6.99-7.04(2H, m), 7.26(1H, m) |
| 101 | 2-OCHMe₂ | COOMe | B | MS: 400(M + H)+ |
| 102 | 2-OCH₂Ph | COCH₂OEt | C | MS: 476(M + H)+ |
| 103 | 2-OCH₂Ph | COCH₃ | A | MS: 432(M + H)+ |
| 104 | 2-OH | COCH₂OEt | *7 | MS: 386(M + H)+, N1: 0.58-3.49(11H, m), 1.09(3H, t, J=6.9 Hz), 3.75(2H, q, J=16.5 Hz), 3.90-4.03(1H, m) 3.96(1H, d, J=13.8 Hz), 4.38(1H, d, J=13.8 Hz), 5.63(1H, s), |

TABLE 2-5-continued

| No. | R | R' | S | D |
|---|---|---|---|---|
| | | | | 6.63(1H, s), 6.70(1H, s), 6.75-6.88(2H, m), 6.89-6.98(1H, m), 7.07-7.18(1H, m), 9.71(1H, brs) |
| 105 | 2-OH | COCH$_3$ | *8 | MS: 342(M + H)+ |
| 106 | 2-OCF$_3$ | COCH$_3$ | A | MS: 410(M + H)+ |
| 107 | 2-OMe-4-F | COCH$_2$CH$_3$ | A | MS: 386(M − H)−, N1: 0.50-3.40(11H, m), 0.99(3H, t, J=7.2 Hz), 3.83(3H, s), 3.71-3.87(2H, m), 3.94-4.06(1H, m), 5.75(1H, s), 6.62-7.04(5H, m) |
| 108 | 2-OMe-4-F | COCH$_2$OEt | C | MS: 418(M + H)+ |

TABLE 2-6

| No. | R | R' | S | D |
|---|---|---|---|---|
| 109 | 2-OMe-4-F | COCH$_3$ | A | MS: 374(M + H)+, N1: 0.58-3.45(9H, m), 2.13(3H, s), 3.73-3.92(2H, m), 3.86(3H, s), 3.93-3.98(1H, m), 5.67(1H, s), 6.69(1H, brs), 6.75(1H, brs), 6.91-7.04(3H, m) |
| 110 | 2-OMe-4-Cl | COCH$_3$ | A | MS: 390(M + H)+ |
| 111 | 2-OMe-4-OCH$_2$Ph | COCH$_3$ | A | MS: 462(M + H)+ |
| 112 | 2-OMe-4-OH | COCH$_3$ | *9 | MS: 372(M + H)+ |
| 113 | 2-OMe-5-F | COCH$_3$ | A | MS: 373(M + H)+ |
| 114 | 2,3-(OMe)$_2$ | COCH$_3$ | A | MS: 386(M + H)+ |
| 115 | 2,4-(OMe)$_2$ | COCH$_3$ | A | MS: 385(M + H)+ |
| 116 | 2,5-(OMe)$_2$ | COCH$_3$ | A | MS: 386(M + H)+ |
| 117 | 2-Me | COCF$_3$ | A | MS: 394(M + H)+ |
| 118 | 2-Me | COCH$_2$CH$_3$ | A | MS: 354(M + H)+, N1: 0.50-3.42(11H, m), 0.99(3H, t, J=6.9 Hz), 2.35(3H, s), 3.77(1H, d, J=16.2 Hz), 3.88(1H, d, J=16.2 Hz), 3.94-4.08(1H, m), 5.65(1H, s), 6.68(1H, s), 6.78(1H, s), 7.01-7.08(1H, m), 7.12-7.30(3H, m) |
| 119 | 2-Me | COCH$_2$OEt | C | MS: 384(M + H)+, N1: 0.43-3.55(11H, m), 1.09(3H, t, J=6.9 Hz), 2.35(3H, s), 3.81(2H, q, J=16.2 Hz), 3.99-4.07(2H, m), 4.33(1H, d, J=14.4 Hz), 5.51(1H, s), 6.70(1H, s), 6.78(1H, s), 6.98-7.07(1H, m), 7.09-7.30(3H, m) |
| 120 | 2-Me | COCH$_2$OAc | C | MS: 398(M + H)+ |
| 121 | 2-Me | COCH$_2$OH | *10 | MS: 356(M + H)+ |
| 122 | 2-Me | COCH$_2$OMe | C | MS: 368(M − H)− |
| 123 | 2-Me | COCH$_3$ | A | MS: 340(M + H)+ |
| 124 | 2-Me | COOEt | B | MS: 370(M + H)+ |

TABLE 2-7

| No. | R | R' | S | D |
|---|---|---|---|---|
| 125 | 2-Me | COOMe | B | MS: 356(M + H)+, N1: 0.50-3.50(10H, m), 2.25(3H, brs), 3.64(3H, s), 3.72(1H, d, J=15.0 Hz), 3.80(1H, d, J=15.0 Hz), 6.01(1H, brs), 6.60(1H, brs), 6.73(1H, brs), 6.98-7.22(4H, m) |
| 126 | 2-Et | COCH$_2$CH$_2$CH$_3$ | A | MS: 382(M + H)+ |
| 127 | 2-Et | COCH$_2$CH$_3$ | A | MS: 368(M + H)+ |
| 128 | 2-Et | COCH$_2$COOMe | C | MS: 417(M − H)−, N1: 0.53-3.40(16H, m), 3.60(3H, s), 3.72-3.97(3H, m), 5.56(1H, s), 6.77(1H, s), 6.82(1H, s), 7.05-7.18(1H, m), 7.28-7.42(2H, m) |
| 129 | 2-Et | COCH$_2$OEt | C | MS: 398(M + H)+, N1: 0.50-3.60(19H, m), 3.73(1H, d, J=15.0 Hz), 3.85(1H, d, J=15.0 Hz), 3.90-4.04(2H, m), 4.26(1H, d, J=14.1 Hz), 5.60(1H, brs), 6.70(1H, brs), 6.78(1H, brs), 7.00-7.30(4H, m) |
| 130 | 2-Et | COCH$_2$OMe | C | MS: 384(M + H)+ |
| 131 | 2-Et | COCH$_3$ | A | MS: 354(M + H)+, N1: 0.50-3.40(14H, m), 2.10(3H, s), 3.77(1H, d, J=15.0 Hz), 3.85(1H, d, J=15.0 Hz), 3.91-4.03(1H, m), 5.64(1H, brs), 6.69(1H, brs), 6.77(1H, brs), 7.00-7.30(4H, m) |
| 132 | 2-Et | COOMe | B | MS: 370(M + H)+ |
| 133 | 2-CHMe$_2$ | COCH$_3$ | A | MS: 366(M − H)− |
| 134 | 2-Br | COCH$_2$CF$_3$ | C | MS: 472(M − H)−, N1: 0.62-3.51(11H, m), 3.82-3.99(3H, m), 5.47(1H, m), 6.86(1H, s), 6.90(1H, s), 7.20(1H, m), 7.31-7.41(2H, m), 7.70(1H, m) |

TABLE 2-8

| No. | R | R' | S | D |
|---|---|---|---|---|
| 135 | 2-Br | COCH$_2$CH$_3$ | A | MS: 418(M + H)+, N1: 0.52-3.42(11H, m), 0.98(3H, t, J=7.2 Hz), 3.79(1H, d, J=15.9 Hz), 3.87(1H, d, J=15.9 Hz), 3.94-4.08(1H, m), 5.62(1H, s), 6.80(1H, s), 6.84(1H, s), 7.16-7.23(1H, m), 7.24-7.35(1H, m), 7.26-7.45(1H, m), 7.66-7.74(1H, m) |

TABLE 2-8-continued

[Structure: tricyclic compound with phenyl group bearing R substituent at positions 2-6, N-R' group, and fused cyclohexane ring with NH]

| No. | R | R' | S | D |
|-----|---|-----|---|---|
| 136 | 2-Br | COCH$_2$COOMe | C | MS: 462(M + H)+, N1: 0.60-3.43(9H, m), 3.51(1H, d, J=15 Hz), 3.59(3H, s), 3.79-3.98(4H, m), 5.43(1H, s), 6.89(1H, s), 6.90(1H, s), 7.21(1H, m), 7.31-7.45(2H, m), 7.70(1H, m) |
| 137 | 2-Br | COCH$_2$OEt | C | MS: 448(M + H)+, N1: 0.50-3.50(11H, m), 1.07(3H, t, J=6.6 Hz), 3.76(1H, d, J=16.0 Hz), 3.86(1H, d, J=16.0 Hz), 3.91-4.03(1H, m), 4.13(1H, d, J=15.0 Hz), 4.42(1H, d, J=15.0 Hz), 5.42(1H, brs), 6.82(1H, brs), 6.84(1H, brs), 7.15-7.41(3H, m), 7.64-7.70(1H, m) |
| 138 | 2-Br | COCH$_2$OMe | C | MS: 434(M − H)− |
| 139 | 2-Br | COCH$_3$ | A | MS: 402(M − H)− |
| 140 | 2-Cl | COCH$_3$ | A | MS: 360(M + H)+, N1: 0.48-3.64(9H, m), 2.16(3H, s), 3.81(1H, d, J=16.2 Hz), 3.89(1H, d, J=−16.2 Hz), 3.94-4.08(1H, m), 5.64(1H, s), 6.85(1H, s), 6.86(1H, s), 7.16-7.23(1H, m), 7.30-7.42(2H, m), 7.46-7.56(1H, m) |
| 141 | 2-Cl | COCH$_2$CH$_3$ | A | MS: 374(M + H)+ |

TABLE 2-9

[Structure: tricyclic compound analogous to above]

| No. | R | R' | S | D |
|-----|---|-----|---|---|
| 142 | 2-Cl | COCH$_2$CH$_2$CH$_3$ | A | MS: 388(M + H)+, N1: 0.50-3.50(16H, m), 3.77(1H, d, J=15.9 Hz), 3.85(1H, d, J=15.9 Hz), 5.71(1H, brs), 6.78(1H, brs), 6.81(1H, brs), 7.14-7.22(1H, m), 7.28-7.40(2H, m), 7.45-7.53(1H, m) |
| 143 | 2-Cl | COCH$_2$CF$_3$ | C | MS: 426(M − H)−, N1: 0.62-3.55(11H, m), 3.81-4.07(3H, m), 5.03(1H, s), 6.89-6.95(2H, m), 7.27(1H, m), 7.43-7.44(2H, m), 7.58(1H, m) |
| 144 | 2-Cl | COCH$_2$OMe | C | MS: 388(M − H)− |

TABLE 2-9-continued

[Structure: tricyclic compound analogous to above]

| No. | R | R' | S | D |
|-----|---|-----|---|---|
| 145 | 2-Cl | COCH$_2$OEt | C | MS: 404(M + H)+, N1: 0.50-3.50(11H, m), 1.07(3H, t, J=6.6 Hz), 3.76(1H, d, J=16.0 Hz), 3.86(1H, d, J=16.0 Hz), 3.91-4.03(1H, m), 4.16(1H, d, J=14.4 Hz), 4.32(1H, d, J=14.4 Hz), 5.55(1H, brs), 6.80(1H, brs), 6.83(1H, brs), 7.14-7.52(4H, m) |
| 146 | 2-Cl | COCH$_2$COOMe | C | MS: 416(M − H)−, N1: 0.61-3.52(10H, m), 3.59-3.99(4H, m), 5.52(1H, m), 6.87(1H, s), 6.88(1H, s), 7.52(1H, m) |
| 147 | 2-Cl | COOMe | B | MS: 376(M + H)+ |
| 148 | 2-F | COCH$_3$ | A | MS: 344(M + H)+ |
| 149 | 2-F | COCH$_2$CH$_3$ | A | MS: 358(M + H)+, N1: 0.63-3.39(14H, m), 3.81-3.89(2H, m), 4.03(1H, m), 5.86(1H, s), 6.77(1H, s), 6.82(1H, s), 7.09-7.25(3H, m), 7.38(1H, m) |

TABLE 2-10

[Structure: tricyclic compound analogous to above]

| No. | R | R' | S | D |
|-----|---|-----|---|---|
| 150 | 2-F | COCH$_2$OEt | C | MS: 388(M + H)+, N1: 0.67-3.49(14H, m), 3.76(1H, d, J=16 Hz), 3.85(1H, d, J=16 Hz), 4.01(1H, m), 4.18(2H, m), 5.80(1H, s), 6.79(1H, s), 6.83(1H, s), 7.11-7.26(3H, m), 7.36(1H, m) |
| 151 | 2-F | COOMe | B | MS: 360(M + H)+, N1: 0.62-3.92(10H, m), 3.64(3H, s), 3.76(1H, d, J=16.8 Hz), 3.83(1H, d, J=16.8 Hz), 6.16-7.01(1H, m), 6.69(1H, s), 6.79(1H, s), 7.07-7.26(3H, m), 7.31-7.44(1H, m) |
| 152 | 2-CF$_3$ | COCH$_3$ | A | MS: 394(M + H)+ |
| 153 | H | COCH$_3$ | A | MS: 326(M + H)+ |
| 154 | H | COCH$_2$CH$_3$ | A | MS: 340(M + H)+, |

TABLE 2-10-continued

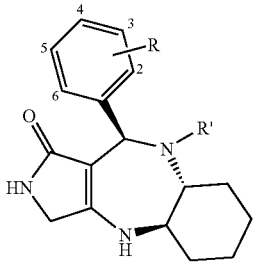

| No. | R | R' | S | D |
|---|---|---|---|---|
| 155 | H | COCH$_2$OEt | C | N1: 0.63-3.32(14H, m), 3.73-3.87(2H, m), 4.00(1H, m), 5.68(1H, s), 6.69(1H, s), 6.79(1H, s), 7.26-7.37(3H, m) MS: 370(M + H)+, N1: 0.60-3.58(14H, m), 3.74-4.00(4H, m), 4.27(1H, d, J=14 Hz), 5.74(1H, s), 6.72(1H, s), 6.80(1H, s), 7.25-7.38(5H, m) |
| 156 | H | COOMe | B | MS: 342(M + H)+, N1: 0.58-3.88(10H, m), 3.42(3H, s), 3.74(1H, d, J=16.5 Hz), 3.82(1H, d, J=16.5 Hz), 5.93-6.06(1H, m), 6.64(1H, s), 6.77(1H, s), 7.14-7.37(5H, m) |
| 157 | 2-NO$_2$ | COCH$_3$ | A | MS: 371(M + H)+ |
| 158 | 2-NH$_2$ | COCH$_3$ | *11 | MS: 341(M + H)+ |
| 159 | 3-Cl | COCH$_3$ | A | MS: 360(M + H)+ |
| 160 | 4-OMe | COCH$_3$ | A | MS: 356(M + H)+ |
| 161 | 4-Br | COCH$_3$ | A | MS: 404(M − H)− |
| 162 | 4-Cl | COCH$_3$ | A | MS: 358(M − H)− |
| 163 | 4-Cl | COCH$_2$OEt | C | MS: 404(M + H)+ |
| 164 | 2-SMe | COCH$_2$OH | *12 | MS: 388(M + H)+, N1: 0.50-3.40(9H, m), 2.48(3H, s), 3.72-3.99(5H, m), 4.37-4.45(1H, m), 4.69-4.82(1H, m), 5.33(1H, s), 6.80(1H, s), 6.83(1H, s), 7.00-7.19(2H, m), 7.29-7.41(2H, m) |
| 165 | H | COCH$_2$OH | *13 | MS: 342(M + H)+, N1: 0.50-2.79(9H, m), 3.75-4.05(4H, m), 4.42(1H, m), 4.72(1H, m), 5.54(1H, s), 6.74(1H, s), 6.80(1H, s), 7.22-7.37(5H, m) |
| 166 | 2-OMe | 3-(oxazol-2-yl)propanoyl | D | MS: 437(M + H)+, N1: 0.50-3.05(14H, m), 3.75(1H, d, J=16.5 Hz), 3.82(1H, d, J=16.5 Hz), 3.83(3H, s), 3.90-4.05(1H, m), 5.83(1H, s), 6.65(1H, s), 6.72(1H, s), 6.86-7.32(4H, m), 7.07(1H, s), 7.95(1H, s) |
| 167 | 2-OEt | 3-(oxazol-2-yl)propanoyl | D | MS: 451(M + H)+, N1: 0.50-3.40(13H, m), 1.31(3H, t), 3.73-4.18(5H, m), 5.84(1H, s), 6.68(1H, s), 6.75(1H, s), 6.89(1H, t), 7.01(2H, d), 7.08(1H, t), 7.26(1H, t), 7.96(1H, s) |
| 168 | 2-SMe | 3-(oxazol-2-yl)propanoyl | D | MS: 453(M + H)+, N1: 0.50-3.40(16H, m), 3.76-4.00(4H, m), 5.70(1H, brs), 6.75(1H, brs), 6.80(1H, brs), 7.03-7.44(5H, m), 7.96(1H, s) |
| 169 | 2-OMe | 3-(thiazol-2-yl)propanoyl | D | MS: 453(M + H)+, N1: 0.50-3.40(9H, m), 3.73(3H, s), 3.70-3.85(2H, m), 3.90-4.05(1H, m), 5.81(1H, s), 6.67(1H, s), 6.71(1H, s), 6.86-7.31(4H, m), 7.53(1H, d, J=3.3 Hz), 7.67(1H, d, J=3.3 Hz) |
| 170 | 2-Me | 3-(thiazol-2-yl)propanoyl | D | MS: 435(M − H)−, N1: 0.45-3.20(13H, m), 2.33(3H, s), 3.75(1H, d, J=16.5 Hz), 3.85(1H, d, J=16.5 Hz), 3.90-4.05(1H, m), 5.66(1H, s), 6.71(1H, s), 6.77(1H, s), 7.00-7.24(4H, m), 7.52(1H, d, J=3.3 Hz), 7.66(1H, d, J=3.3 Hz) |
| 171 | 2-OCF3 | 3-(thiazol-2-yl)propanoyl | D | MS: 505(M − H)−, N1: 0.55-3.30(13H, m), 3.77(1H, d, J=16.5 Hz), 3.85(1H, d, J=16.5 Hz), 3.95-4.05(1H, m), 5.84(1H, s), 6.82(1H, s), 6.83(1H, s), 7.20-7.50(4H, m), 7.52(1H, d, J=3.3 Hz), 7.65(1H, d, J=3.3 Hz) |
| 172 | 2-OEt | 3-(thiazol-2-yl)propanoyl | D | MS: 465(M − H)−, N1: 0.50-3.25(13H, m), 1.22(3H, t, J=6.9 Hz), 3.75(1H, d, J=16.2 Hz), 3.82(1H, d, J=16.2 Hz), 3.90-4.10(3H, m), 5.80(1H, s), 6.67(1H, s), 6.72(1H, s), 6.82-7.30(4H, m), 7.53(1H, d, J=3.3 Hz), 7.66(1H, d, J=3.3 Hz) |
| 173 | 2-SMe | 3-(thiazol-2-yl)propanoyl | D | MS: 469(M + H)+, N1: 0.50-3.40(16H, m), 3.77(1H, d, J=16.7 Hz), 3.88(1H, d, J=16.7 Hz), 3.96(1H, m), 5.69(1H, brs), 6.73(1H, brs), 6.79(1H, brs), 7.02-7.42(4H, m), 7.52-7.68(2H, m) |
| 174 | 2-OMe | 3-(5-Me-thiazol-2-yl)propanoyl | D | MS: 465(M − H)−, N1: 0.50-3.30(13H, m), 2.37(3H, s), 3.73(1H, d, J=16.5 Hz), 3.74(3H, s), 3.82(1H, d, J=16.5 Hz), 3.90-4.05(1H, m), 5.81(1H, s), 6.66(1H, s), 6.71(1H, s), 6.84-7.34(4H, m), 7.31(1H, d, J=1.5 Hz) |
| 175 | 2-Me | 3-(pyridine-2-yl)propanoyl | D | MS: 431(M + H)+, N1: 0.45-3.20(13H, m), 2.34(3H, s), 3.76(1H, d, J=16.8 Hz), 3.86(1H, d, J=16.8 Hz), 3.90-4.05(1H, m), 5.69(1H, s), 6.69(1H, s), 6.76(1H, s), 7.00-7.26(4H, m), 7.14-8.46(4H, m) |
| 176 | 2-OMe | 3-(pyridine-2-yl)propanoyl | D | MS: 445(M − H)−, N1: 0.50-3.30(13H, m), 3.75(1H, d, J=16.5 Hz), 3.78(3H, s), 3.82(1H, d, J=16.5 Hz), 3.90-4.05(1H, m), 5.84(1H, s), 6.65(1H, s), 6.70(1H, s), 6.84-7.22(4H, m), 7.23-8.50(4H, m) |
| 177 | 2-OMe | 3-(pyrimidine-2-yl)propanoyl | D | MS: 448(M + H)+, N1: 0.50-3.40(13H, m), 3.70-3.90(2H, m), 3.85(3H, s), 3.90-4.05(1H, m), 5.90(1H, s), 6.65(1H, s), |

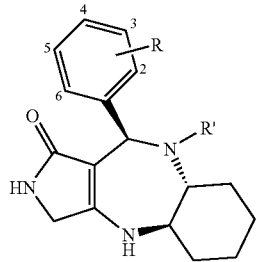

TABLE 2-10-continued

| No. | R | R' | S | D |
|---|---|---|---|---|
| | | | | 6.72(1H, s), 6.88-7.34(5H, m), 8.72(2H, d, J=5.1 Hz) |

Symbols in the above tables have the following meanings:
Co: compound number
No: Example number,
R: substituent on the benzene ring,
R': substituent on nitrogen atom,
D: compound data,
S: production process in Step 2,
ST: Chemical structural formula,
MS: ESI-MS m/z,
N1: $^1$H-NMR (DMSO-d6, TMS internal standard, □ ppm), and
*: notes.

The numerals before the substituents indicate the positions of the substituents on the benzene ring. For example, 2,5-(OMe)2 indicates that methoxyl groups are on the 2- and 5-positions, and COCH$_2$CH$_2$-(3,4-F$_2$-Ph) indicates 3-(3,4-difluorophenyl)propanoyl group. Z represents benzyloxycarbonyl group. The notes (*1 to *11) in the tables indicate as follows:

*1: The compound was synthesized by the hydrolysis of the compound of Example 52 with sodium hydroxide by an ordinary method.
*2: The compound was synthesized by the hydrolysis of the compound of Example 60 with sodium hydroxide by an ordinary method.
*3: The compound was synthesized by the reduction of the compound of Example 60 with lithium aluminum hydride by an ordinary method.
*4: The compound was synthesized by removing the protecting group of the compound of Example 63 by the palladium carbon/hydrogenation by an ordinary method.
*5: The compound was synthesized by removing the protecting group of the compound of Example 65 by the palladium carbon/hydrogenation by an ordinary method.
*6: The compound was synthesized by the hydrolysis of the compound of Example 91 with sodium hydroxide by an ordinary method.
*7: The compound was synthesized by removing the protecting group of the compound of Example 102 by the palladium carbon/hydrogenation by an ordinary method.
*8: The compound was synthesized by removing the protecting group of the compound of Example 103 by the palladium carbon/hydrogenation by an ordinary method.
*9: The compound was synthesized by removing the protecting group of the compound of Example 111 by the palladium carbon/hydrogenation by an ordinary method.
*10: The compound was synthesized by the hydrolysis of the compound of Example 120 with sodium hydroxide by an ordinary method.
*11: The compound was synthesized by the reduction of the compound of Example 157 with palladium carbon/hydrogenation by an ordinary method.
*12: The compound of Example 164 was synthesized by acylation of compound (X26) using Production process D, and then subjecting the resultant to solvolysis with potassium carbonate/methanol.
*13: The compound of Example 165 was synthesized by acylation of compound (X20) using Production process D, and then subjecting the resultant to solvolysis with potassium carbonate/methanol.

Compounds of Examples 178 to 182 were synthesized by the same process as that in Example 45.

Example 183

Acetic anhydride (130 mg, 1,3 mmol) was added to a solution of the compound of Example 39 (20 mg, 0.06 mmol) in pyridine (1 ml), and they were stirred at 90° C. for 4 hours. The solvent was evaporated, and the product was purified by the silica gel thin-layer chromatography to obtain the compound of Example 183 (23 mg, 89%) in the form of a white solid.

Examples 184 and 185

Compounds of Examples 184 and 185 were synthesized by methylating the compound of Example 45 with methyl iodide by an ordinary method.

Example 186

Methyl iodide (0.08 ml, 1.3 mmol) was added to a solution of the compound of Example 39 (40 mg, 0.13 mmol) in dichloromethane (1 ml), and they were stirred at room temperature for 48 hours. The solvent was evaporated, and the product was purified by the alumina thin-layer chromatography to obtain the compound of Example 186 in the form of a white solid (9 mg, 21%).

Example 187

The compound of Example 187 was synthesized in the same manner as that of Example 186 except that methyl iodide used for the alkylation was replaced with ethyl bromoacetate.

Example 188

The compound of Example 188 was synthesized by the same reaction as that in Step 1 in Example 36 and in Example 45 except that tetramic acid was replaced with 1,3-cyclopentanedione.

Example 189

The compound of Example 189 was synthesized by the same reaction as that in Example 1 except that 1,2-phenylenediamine was replaced with 2-aminothiophenol and that 4-bromobenzaldehyde was used as the aldehyde.

Example 190

The compound of Example 190 was synthesized by the same reaction as that in Example 1 except that 1,2-phenylenediamine was replaced with 2-aminophenol and that 4-bromobenzaldehyde was used as the aldehyde.

Example 191

Acetic acid (10 mg) and 4-bromobenzaldehyde (54 mg, 0.29 mmol) were added to a solution of 5-(2-aminophenyl) methyl-1,2-dihydropyrazol-3-one (50 mg, 0.25 mmol) in methanol (3 ml), and they were stirred at 70° C. for 20 hours. After the completion of the reaction, the solvent was evaporated, and diethyl ether was added to the obtained solid. After the filtration, the product was washed to obtain the compound of Example 191 (1 mg, 2%).

Tables 3-1 to 3-3 show the chemical structural formulae of the compounds obtained in Examples 178 to 191 and the data of the compounds.

TABLE 3-1

| No | ST | D |
|---|---|---|
| 178 | 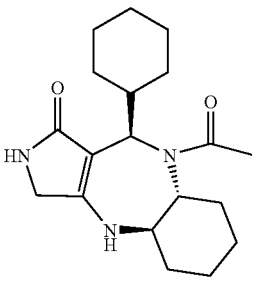 | MS: 332(M + H)+, N1: 0.50-3.40(20H, m), 1.88(3H, s), 3.50-3.71(2H, m), 3.78-3.94(1H, m), 4.02-4.20(1H, m), 6.40(1H, s), 6.57(1H, s) |
| 179 | 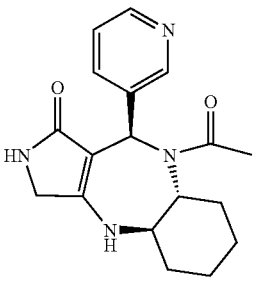 | MS: 327(M + H)+, N1: 0.50-3.40(9H, m), 2.16(3H, s), 3.77(1H, d, J=15.0 Hz), 3.83(1H, d, J=15.0 Hz), 3.93-4.08(1H, m), 5.65(1H, s), 6.78(1H, s), 6.84(1H, s), 7.32-7.44(1H, m), 7.60-7.69(1H, m), 8.40-8.54(2H, m) |
| 180 | 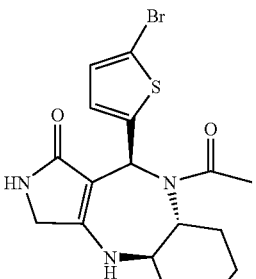 | MS: 410(M + H)+, N1: 0.50-3.40(9H, m), 2.08(3H, s), 3.75(2H, s), 3.90-4.04(1H, m), 5.68(1H, s), 6.72(1H, d, J=3.9 Hz), 6.81(1H, s), 6.82(1H, s), 7.07(1H, d, J=3.9 Hz) |
| 181 | 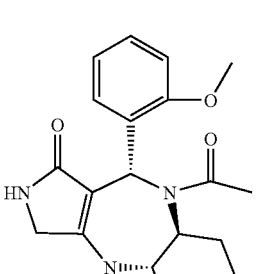 | MS: 354(M − H)−, N1: 0.90-2.90(9H, m), 2.12(3H, s), 3.74-3.84(5H, m), 3.99(1H, m), 5.75(1H, s), 6.64(1H, s), 6.92(1H, 2s), 6.99-7.33(4H, m), [α]D=+127.9° (c=0.215, MeOH) |

TABLE 3-1-continued

| No | ST | D |
|---|---|---|
| 182 | (structure) | MS: 350(M + H)+, N1: 1.60(3H, s), 3.82(3H, s), 3.99(1H, d, J=16.2 Hz), 4.02(1H, d, J=-16.2 Hz), 6.50-7.10(9H, m), 7.22(1H, s), 9.40(1H, s) |

TABLE 3-2

| No | ST | D |
|---|---|---|
| 183 | (structure) | MS: 398(M + H)+, N1: 0.57-3.46(9H, m), 2.18(3H, s), 2.30(3H, s), 3.86(3H, s), 4.03-4.14(1H, m), 4.20(1H, d, J=15.6 Hz), 4.28(1H, d, J=15.6 Hz), 5.80(1H, s), 6.88-6.98(1H, m), 7.03-7.14(2H, m), 7.29-7.38(1H, m), 7.53(1H, s) |
| 184 | (structure) | MS: 384(M + H)+, N1: 0.50-3.40(9H, m), 2.12(3H, s), 2.75(3H, s), 2.80(3H, s), 3.82(3H, s), 3.88-4.14(3H, m), 5.68(1H, s), 6.84-6.92(1H, m), 6.98-7.05(2H, m), 7.24-7.32(1H, m) |
| 185 | (structure) | MS: 370(M + H)+, N1: 0.50-3.40(9H, m), 2.12(3H, s), 2.71(3H, s), 3.72-4.04(6H, m), 5.72(1H, s), 6.68(1H, s), 6.84-7.06(3H, m), 7.24-7.32(1H, m) |

TABLE 3-2-continued
| No | ST | D |
|---|---|---|
| 186 | 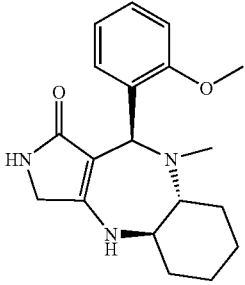 | MS: 326(M + H)+, N1: 0.98-3.14(12H, m), 3.84-4.00(5H, m), 5.09(1H, s), 6.81(1H, m), 6.94-7.02(2H, m), 7.20(1H, m) |
| 187 | 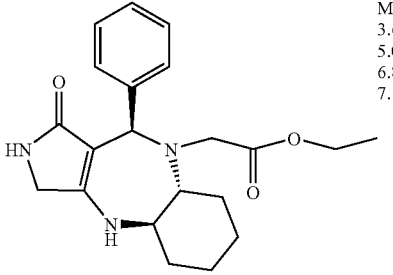 | MS: 400(M + H)+, N1: 0.83-3.50(14H, m), 3.69-3.84(5H, m), 4.04-4.17(3H, m), 5.00(1H, s), 6.30(1H, s), 6.62(1H, m), 6.80(1H, m), 6.91-6.94(2H, m), 7.18(1H, m) |
TABLE 3-3
| No | ST | D |
|---|---|---|
| 188 | 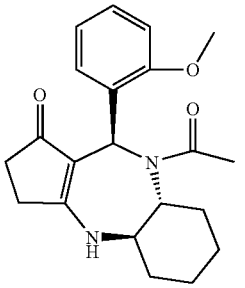 | MS: 355(M + H)+, N1: 0.90-2.90(13H, m), 2.11(3H, s), 3.83(3H, s), 4.01(1H, m), 5.76(1H, s), 6.80-7.30(4H, m), 7.45(1H, s) |
| 189 | 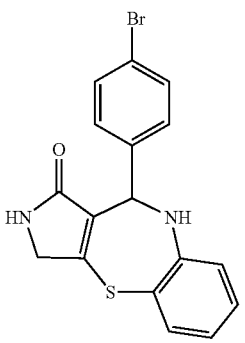 | MS: 374(M + H)+, N1: 4.02(2H, s), 5.30(1H, s), 6.22(1H, s), 6.77-7.18(8H, m), 7.60(1H, s) |

TABLE 3-3-continued

| No | ST | D |
|---|---|---|
| 190 | (structure: 4-bromophenyl attached to pyrrolone fused with benzoxazepine) | MS: 357, 359(M + H)+, N1: 4.08(2H, s), 6.05(1H, s), 6.51-7.45(8H, m), 7.30(1H, s), 9.58(1H, s) |
| 191 | (structure: 4-bromophenyl attached to pyrazolone fused with benzazepine) | MS: 357(M + H)+, N1: 3.75(1H, d, J=16.2 Hz), 3.88(1H, d, J=16.2 Hz), 5.10-5.21(2H, m), 6.62-6.69(1H, m), 6.76-6.85(1H, m), 6.92-7.00(1H, m), 7.05-7.14(3H, m), 7.35-7.42(2H, m) |

The compounds of Examples 192 to 208 shown in Table 3-4 were synthesized by a process substantially similar to those described in the above-mentioned Examples or by a process self-evident for those skilled art.

TABLE 3-4

| No. | R1 | R2 | R3 | R4 |
|---|---|---|---|---|
| 192 | 2-OMe | CO-cyclopropyl | H | H |
| 193 | 2-cyclopropoxy | COCH$_3$ | H | H |
| 194 | 2-cyclopropoxy | COCH2OH | H | H |
| 195 | 2-OCF3 | COCH2OH | H | H |
| 196 | 2-OCF3 | COCH$_2$OMe | H | H |
| 197 | 2-SMe | COCH$_3$ | H | H |
| 198 | 2-Me | COCH$_2$CH$_3$ | H | Me |
| 199 | 2-Me | COCH2OH | H | Me |
| 200 | 2-Et | COCH$_3$ | (S)—Me | H |
| 201 | 2-Et | COCH$_2$CH$_3$ | (S)—Me | H |
| 202 | 2-Et | COCH$_3$ | H | Et |
| 203 | 2-cyclopropyl | COCH2OH | H | H |
| 204 | 2-cyclopropyl | COCH$_3$ | H | H |
| 205 | 2-Me, 3-F | COCH$_2$CH$_3$ | H | H |
| 206 | 2-Me, 3-F | COCH$_3$ | H | H |

TABLE 3-4-continued

| No. | R1 | R2 | R3 | R4 |
|---|---|---|---|---|
| 207 | 2-Me-3-Cl | COCH$_2$OEt | H | H |
| 208 | 2-F | CO-cyclopropyl | H | H |

Symbols in the above tables have the following meanings:
No: Example number,
ST: Chemical structural formula,
D: compound data,
MS: ESI-MS m/z, and
N1: $^1$H-NMR (DMSO-d6, TMS internal standard, δ ppm).

Compounds of chemical structural formulae shown in Tables 4 and 5 can be easily produced by a process substantially similar to those described in the above Examples or by a process self-evident for those skilled in the art.

Symbols in the tables have the following meanings:
REF: Referential Example number,
R: substituent on the benzene ring,
R': substituent on nitrogen atom, and
ST: chemical structural formula.

TABLE 4

| REF | R | R' |
|---|---|---|
| 1 | 2-SMe | COCH₃ |
| 2 | 2-SO₂Me | COCH₃ |
| 3 | 2-COMe | COCH₃ |
| 4 | 2-COOMe | COCH₃ |
| 5 | 2-COOH | COCH₃ |
| 6 | 3-OMe | COCH₃ |
| 7 | 3-OEt | COCH₃ |
| 8 | 3-Me | COCH₃ |
| 9 | 3-Et | COCH₃ |
| 10 | 3-CHMe₂ | COCH₃ |
| 11 | 3-Br | COCH₃ |
| 12 | 3-OH | COCH₃ |
| 13 | 4-Me | COCH₃ |
| 14 | 4-Et | COCH₃ |
| 15 | 4-CHMe₂ | COCH₃ |
| 16 | 4-OH | COCH₃ |
| 17 | 4-COOMe | COCH₃ |
| 18 | 2,4-Me₂ | COCH₃ |
| 19 | 2,5-Me₂ | COCH₃ |
| 20 | 2,6-Me₂ | COCH₂OEt |
| 21 | 2-SMe | COCH₂OEt |
| 22 | 2-SO₂Me | COCH₂OEt |
| 23 | 2-COMe | COCH₂OEt |
| 24 | 2-COOMe | COCH₂OEt |
| 25 | 2-COOH | COCH₂OEt |
| 26 | 3-OMe | COCH₂OEt |
| 27 | 3-OEt | COCH₂OEt |
| 28 | 3-Me | COCH₂OEt |
| 29 | 3-Et | COCH₂OEt |
| 30 | 3-CHMe₂ | COCH₂OEt |
| 31 | 3-Br | COCH₂OEt |
| 32 | 3-OH | COCH₂OEt |
| 33 | 4-Me | COCH₂OEt |
| 34 | 4-Et | COCH₂OEt |
| 35 | 4-CHMe₂ | COCH₂OEt |
| 36 | 4-OH | COCH₂OEt |
| 37 | 4-COOMe | COCH₂OEt |
| 38 | 2,4-Me₂ | COCH₂OEt |
| 39 | 2,5-Me₂ | COCH₂OEt |
| 40 | 2,6-Me₂ | COCH₂OEt |
| 41 | 2-SMe | COOMe |
| 42 | 2-SO₂Me | COOMe |
| 43 | 2-COMe | COOMe |
| 44 | 2-COOMe | COOMe |
| 45 | 2-COOH | COOMe |
| 46 | 3-OMe | COOMe |
| 47 | 3-OEt | COOMe |
| 48 | 3-Me | COOMe |
| 49 | 3-Et | COOMe |
| 50 | 3-CHMe₂ | COOMe |
| 51 | 3-Br | COOMe |
| 52 | 3-OH | COOMe |
| 53 | 4-Me | COOMe |
| 54 | 4-Et | COOMe |
| 55 | 4-CHMe₂ | COOMe |
| 56 | 4-OH | COOMe |
| 57 | 4-COOMe | COOMe |
| 58 | 2,4-Me₂ | COOMe |
| 59 | 2,5-Me₂ | COOMe |
| 60 | 2,6-Me₂ | COOMe |

TABLE 5-1

| REF | ST |
|---|---|
| 61 | |
| 62 | |
| 63 | |
| 64 | |
| 65 | |

TABLE 5-1-continued
| REF | ST |
|---|---|
| 66 | 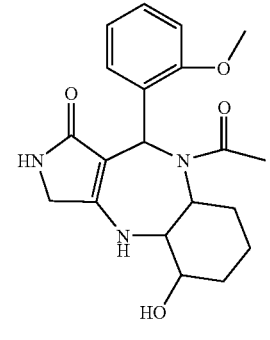 |
| 67 | 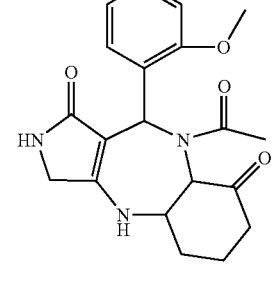 |
| 68 | 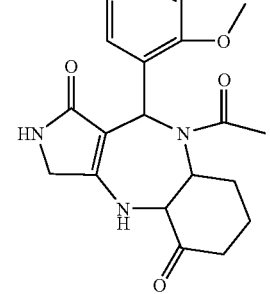 |
TABLE 5-2
| REF | ST |
|---|---|
| 69 | 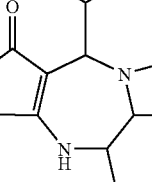 |
TABLE 5-2-continued
| REF | ST |
|---|---|
| 70 | 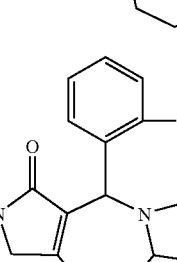 |
| 71 | 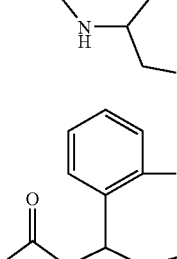 |
| 72 | 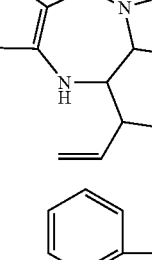 |
| 73 | |
| 74 | |

TABLE 5-2-continued

| REF | ST |
|---|---|
| 75 | (structure) |
| 76 | (structure) |

Test Example 1

Evaluation of the Sugar-Transporting Activity:

1. Preparation of Adipose Cells of Rats:

After the decapitation and venesection of 6 male Wistar rats (body weight: 150 to 200 g), an incision was made in the abdomen of each rat to extract 6 g in total of epididymal adipose tissues. The tissues were finely cut into 2 mm×2 mm pieces in 6 ml of KRH (Krebs-Ringer Hepes, composition: 130 mM of sodium chloride, 4.7 mM of potassium chloride, 1.2 mM of potassium dihydrogenphosphate, 1.2 mM of magnesium sulfate, 1 mM of calcium chloride and 25 mM of Hepes, pH=7.6) containing 5% of BSA (bovine serum albumin). 24 mg of collagenase (type I) was added thereto and the digestion treatment was conducted for about 40 minutes to obtain about 6 ml of isolated adipose cells. The collagenase was removed by the buffer exchange. 2% BSA/KRH solution was added to the residue for the re-suspension to obtain 45 ml of an adipose cell suspension.

2. Evaluation of the Sugar-Transporting Activity:

The sugar-transporting activity of the compounds of the present invention was evaluated with reference to a method described in a literature [Annual Review of Biochemistry, Vol. 55, p. 1059 (1986)]. In the test, 200 µl of the adipose cell suspension was poured in each polystyrene test tube, 100 µl of the solution of the test substance (by dilution of 10 mg/ml substance dimethyl sulfoxide solution with KRH) was added thereto, and the obtained mixture was shaken and then cultured at 37° C. for 30 minutes.

The sugar-transporting activity was evaluated by measuring the quantity of 2-[$^{14}$C(U)]-deoxy-D-glucose incorporated per a unit time. Namely, 2-[$^{14}$C(U)]-deoxy-D-glucose was added to the adipose cell suspension after the pre-culture (the final concentration: 0.5 µCi/sample). 5 minutes after, cytochalasin B (final concentration: 10 µM) was added to the mixture to terminate the sugar transportation. After forming a dinonyl phthalate layer, the obtained mixture was centrifuged to separate the adipose cells from the buffer. The quantity of 2-[$^{14}$C(U)]-deoxy-D-glucose contained in the adipose cell layer was determined with a liquid scintillation counter to determine the quantity of the incorporated sugar. In this evaluation system, when insulin (100 nM) having the effect of increasing the sugar transportation was used, the effect was about 7 times as high as that obtained in the insulin-free control group.

The results of the evaluation of the sugar-transporting activity obtained by using 100 µg/ml of each compound of the present invention are shown in Table 6. The sugar transporting activity in Table 6 was evaluated on the basis of the reinforcing effect of insulin (100 nM). "+" indicates that the effect was 20 to 40%, "++" indicates that the effect was 40 to 70%, and "+++" indicates that the effect was at least 70% based on the reinforcing effect of insulin. The symbols in Table 6 are as follows:

No: Example No., and

A: sugar transporting activity.

TABLE 6

| No | A |
|---|---|
| 1 | ++ |
| 2 | + |
| 3 | + |
| 5 | + |
| 6 | ++ |
| 7 | ++ |
| 8 | +++ |
| 9 | ++ |
| 10 | + |
| 11 | ++ |
| 12 | + |
| 13 | ++ |
| 14 | +++ |
| 15 | ++ |
| 16 | ++ |
| 17 | + |
| 20 | + |
| 21 | ++ |
| 22 | +++ |
| 23 | +++ |
| 24 | +++ |
| 25 | ++ |
| 26 | ++ |
| 27 | ++ |
| 28 | ++ |
| 29 | + |
| 30 | + |
| 31 | +++ |
| 34 | + |
| 37 | ++ |
| 38 | +++ |
| 39 | +++ |
| 40 | +++ |
| 41 | +++ |
| 43 | ++ |
| 44 | + |

The results of the evaluation of the sugar-transporting activity obtained by using each compound of the present invention are shown in Table 7. The sugar transporting activity in Table 7 was determined in terms of the concentration (EC50: µg/ml) of a test compound, having a reinforcing effect corresponding to 50% on the basis of the reinforcing effect of insulin having a reinforcing effect of 100%.

The symbols in Table 7 are as follows:
No: Example No., and
A: sugar transporting activity.

TABLE 7

| No | A |
| --- | --- |
| 45 | 1.3 |
| 46 | 0.77 |
| 47 | 4.6 |
| 48 | 4.5 |
| 49 | 0.47 |
| 50 | 9.5 |
| 51 | 2 |
| 52 | 5.9 |
| 53 | 2 |
| 54 | 2.2 |
| 55 | 4.6 |
| 56 | 5 |
| 59 | 1.1 |
| 60 | 4.8 |
| 62 | 4.8 |
| 65 | 8 |
| 66 | 8 |
| 67 | 3.4 |
| 68 | 0.9 |
| 69 | 4 |
| 70 | 4.2 |
| 71 | 2.6 |
| 72 | 5.5 |
| 76 | 10 |
| 77 | 20 |
| 78 | 18 |
| 79 | 8.6 |
| 80 | 6 |
| 81 | 4.2 |
| 82 | 6 |
| 83 | 11 |
| 84 | 3.6 |
| 85 | 7 |
| 87 | 15 |
| 88 | 1.9 |
| 89 | 1.3 |
| 90 | 5 |
| 91 | 13 |
| 92 | 3.8 |
| 93 | 3.6 |
| 94 | 4 |
| 95 | 1.5 |
| 96 | 7 |
| 97 | 12 |
| 98 | 14 |
| 99 | 2 |
| 100 | 2 |
| 101 | 4.8 |
| 102 | 4 |
| 103 | 3.6 |
| 104 | 1 |
| 105 | 3.7 |
| 106 | 20 |
| 107 | 0.82 |
| 108 | 7.8 |
| 109 | 8 |
| 110 | 6 |
| 112 | 20 |
| 113 | 10 |
| 114 | 12 |
| 115 | 10 |
| 117 | 6 |
| 118 | 2 |
| 119 | 4 |
| 120 | 8 |
| 121 | 2.5 |
| 122 | 6 |
| 123 | 5 |
| 124 | 7 |
| 125 | 2 |
| 126 | 5 |
| 127 | 2.2 |
| 128 | 2 |

TABLE 7-continued

| No | A |
| --- | --- |
| 129 | 5.4 |
| 130 | 6 |
| 131 | 4 |
| 132 | 4 |
| 133 | 20 |
| 134 | 0.5 |
| 135 | 1.5 |
| 136 | 1.5 |
| 137 | 8.6 |
| 138 | 6 |
| 139 | 6 |
| 140 | 20 |
| 141 | 3 |
| 142 | 4 |
| 143 | 0.5 |
| 144 | 5 |
| 145 | 10.7 |
| 146 | 2 |
| 147 | 2.4 |
| 148 | 20 |
| 149 | 2 |
| 150 | 2 |
| 151 | 2 |
| 153 | 20 |
| 154 | 1.5 |
| 155 | 2.7 |
| 156 | 2 |
| 157 | 20 |
| 158 | 12 |
| 160 | 4.4 |
| 161 | 17 |
| 163 | 6 |
| 164 | 2 |
| 165 | 1.5 |
| 166 | 0.064 |
| 167 | 0.10 |
| 168 | 0.070 |
| 169 | 0.0060 |
| 170 | 0.090 |
| 171 | 0.070 |
| 172 | 0.060 |
| 173 | 0.060 |
| 174 | 0.050 |
| 175 | 0.020 |
| 176 | 0.021 |
| 177 | 0.10 |
| 180 | 19 |

In the above evaluation tests, the compounds of the present invention exhibited the effect of increasing the sugar-transporting activity.

Test Example 2

Evaluation of Hypoglycemic Effect in db/db Mice

A test compound was orally administered to C57BL/KsJ-db/dbJcl mice after the fasting for 20 hours. The blood sample was taken from the tail vein of each mouse immediately before the administration and also 30, 60, 120 and 180 minutes after the administration to determine the blood sugar level. The test compound was administered in the form of a suspension in 0.5% methylcellulose solution or a solution in Polyethylene glycol 400.

When 100 mg/kg of each of the compounds produced in Examples 80, 88, 119, 129, 131, 137, 140, 154, 155 and 156 was given once, it exhibited an effect of lowering the blood sugar level by at least 30% as compared with that in control groups.

It is apparent from those results that the compounds of the present invention have the effect of increasing the sugar-transporting activity and that they are useful for treating patients suffering from diabetes. Namely, since they are capable of lowering the blood sugar level by the effect of increasing the sugar-transporting activity, they are useful as agents for preventing and/or treating diabetes, diabetic peripheral neuropathy, diabetic nephropathy, diabetic retinopathy, diabetic macroangiopathy, impaired glucose tolerance or adiposis.

What is claimed is:

1. A compound of formula (I) or a pharmaceutically acceptable salt thereof:

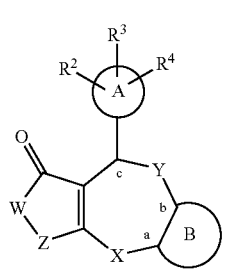

(I)

wherein A represents an aromatic ring, a heterocyclic ring or an aliphatic ring; $R^2$, $R^3$ and $R^4$ may be the same or different from one another and independently represent a hydrogen atom, a halogen atom, a hydroxyl group, an alkyl group, a mercapto group, an alkoxyl group, an alkylthio group, an alkylsulfonyl group, an acyl group, an acyloxyl group, an amino group, an alkylamino group, a carboxyl group, an alkoxycarbonyl group, a carbamoyl group, a nitro group, a cyano group, a trifluoromethyl group, an alkenyl group which may have a substituent(s), an alkynyl group which may have a substituent(s), an aryl group which may have a substituent(s), a heteroaryl group which may have a substituent(s), a benzyloxyl group which may have a substituent(s), an aryloxyl group which may have a substituent(s), a heteroaryloxyl group which may have a substituent(s), an arylamino group which may have a substituent(s), an arylvinyl group which may have a substituent(s) or an arylethynyl group which may have a substituent(s); B represents a fused aliphatic ring which may have a substituent(s); —X— and —Y— may be the same or different from one another and they independently represent —NH— and —NR$^5$—, wherein R$^5$ represents a lower alkyl group which may have a substituent(s), an acyl group which may have a substituent(s), an alkoxycarbonyl group which may have a substituent(s), a carbamoyl group which may have a substituent(s) or a sulfonyl group which may have a substituent(s); —Z— represents —CH$_2$— or —CR$^6$R$^7$—, wherein R$^6$ and R$^7$ may be the same or different from each other and they independently represent a hydrogen atom, a halogen atom, a hydroxyl group, an alkyl group which may have a substituent(s), an aryl group, a mercapto group, an alkoxyl group, an alkylthio group, an alkylsulfonyl group, an acyl group, an acyloxyl group, an amino group, an alkylamino group, a carboxyl group, an alkoxycarbonyl group, a carbamoyl group, a nitro group, a cyano group or a trifluoromethyl group; —W— represents —NR$^1$—, wherein R$^1$ represents a hydrogen atom, a lower alkyl group which may have a substituent(s) or an aryl group which may have a substituent(s); and a, b and c each represent the position of carbon atom;

said heterocyclic ring is selected from the group consisting of pyridine ring, dihydropyran ring, pyridazine ring, pyrimidine ring, pyrazine ring, pyrrole ring, furan ring, thiophene ring, oxazole ring, isoxazole ring, pyrazole ring, imidazole ring, thiazole ring, isothiazole ring, thiadiazole ring, pyrrolidine ring, piperidine ring, piperazine ring, indole ring, isoindole ring, benzofuran ring, isobenzofuran ring, benzothiophene ring, benzopyrazole ring, benzoimidazole ring, benzoxazole ring, benzothiazole ring, purine ring, pyrazolopyridine ring, quinoline ring, isoquinoline ring, naphthyridine ring, quinazoline ring, benzodiazepine ring, carbazole ring, and dibenzofuran ring;

said acyl group is selected from the group consisting of formyl group, acetyl group, propionyl group, butyryl group, isobutyryl group, valeryl group, isovaleryl group, pivaloyl group, hexanoyl group, acryloyl group, methacryloyl group, crotonoyl group, isocrotonoyl group, benzoyl group, naphthoyl group, furanyl carbonyl group, thienyl carbonyl group, isoxazolyl carbonyl group, and thiazolyl carbonyl group;

said acyloxyl group is selected from the group consisting of formyloxyl group, acetyloxy group, propionyloxyl group, butyryloxyl group, isobutyryloxyl group, valeryloxyl group, isovaleryloxyl group, pivaloyloxyl group, hexanoyloxyl group, acryloyloxyl group, methacryloyloxyl group, crotonoyloxyl group, isocrotonoyloxyl group, benzoyloxyl group, and naphthoyloxyl group;

said heteroaryl group is selected from the group consisting of pyridyl group, pyridazinyl group, pyrimidinyl group, pyrazinyl group, pyrrolyl group, furanyl group, thienyl group, oxazolyl group, isoxazolyl group, pyrazolyl group, imidazolyl group, thiazolyl group, isothiazolyl group, thiadiazolyl group, indolyl group, isoindolyl group, benzofuryl group, isobenzofuryl group, benzothienyl group, benzopyrazolyl group, benzoimidazolyl group, benzoxazolyl group, benzothiazolyl group, quinolyl group, isoquinolyl group, naphthylidinyl group, quinazolyl group, oxadiazolyl group, and pyridonyl group;

said fused aliphatic ring is selected from the group consisting of cyclopropane ring, cyclobutane ring, cyclopentane ring, cyclohexane ring, cycloheptane ring, cyclooctane ring, and decalin ring, and wherein the substituent(s) is selected from the group consisting of halogen atoms, hydroxyl group, alkyl groups, mercapto group, alkoxyl groups, alkylthio groups, alkylsulfonyl groups, acyl groups, acyloxyl groups, amino group, alkylamino groups, carboxyl group, alkoxycarbonyl groups, carbamoyl groups, nitro group, cyano group, trifluoromethyl group, aryl groups and heteroaryl groups.

2. A pharmaceutical composition comprising a compound or pharmaceutically acceptable salt thereof according to claim 1 and a pharmaceutically acceptable carrier.

3. A method for treating hypoglycemia, comprising administering to a subject in need thereof an effective amount of a compound or pharmaceutically acceptable salt thereof according to claim 1.

4. A method for treating diabetes, diabetic peripheral neuropathy, diabetic nephropathy, diabetic retinopathy, diabetic macroangiopathy, impaired glucose tolerance or adiposis, which comprises administering to a subject in need thereof an effective amount of a compound or pharmaceutically acceptable salt thereof according to claim 1.

5. The compound or pharmaceutically acceptable salt thereof according to claim 1, wherein in general formula (I), $R^2$, $R^3$ and $R^4$ may be the same or different from one another and independently represent a hydrogen atom, a halogen atom, a hydroxyl group, an alkyl group, a mercapto group, an alkoxyl group, an alkylthio group, an alkylsulfonyl group, an acyl group, an acyloxyl group, an amino group, an alkylamino group, a carboxyl group, an alkoxycarbonyl group, a carbamoyl group, a nitro group, a cyano group, a trifluoromethyl group, an aryl group which may have a substituent(s), a heteroaryl group which may have a substituent(s), a benzyloxyl group which may have a substituent(s), an aryloxyl group which may have a substituent(s), a heteroaryloxyl group which may have a substituent(s), an arylamino group which may have a substituent(s), an arylvinyl group which may have a substituent(s) or an arylethynyl group which may have a substituent(s); —X— and —Y— may be the same or different from one another and they independently represent —NH— or —NR$^5$—, wherein R$^5$ represents a lower alkyl group or an acyl group which may have a substituent(s); —Z— represents —CH$_2$— or —CR$^6$R$^7$—, wherein R$^6$ and R$^7$ may be the same or different from each other and they independently represent a hydrogen atom, a halogen atom, a hydroxyl group, an alkyl group, an aryl group, a mercapto group, an alkoxyl group, an alkylthio group, an alkylsulfonyl group, an acyl group, an acyloxyl group, an amino group, an alkylamino group, a carboxyl group, an alkoxycarbonyl group, a carbamoyl group, a nitro group, a cyano group or a trifluoromethyl group; and wherein:
  (i) the substituent(s) is selected from the group consisting of halogen atoms, hydroxyl group, alkyl groups, aryl groups, mercapto group, alkoxyl groups, alkylthio groups, alkylsulfonyl groups, acyl groups, acyloxyl groups, amino group, alkylamino groups, carboxyl group, alkoxycarbonyl groups, carbamoyl groups, nitro group, cyano group and trifluoromethyl group.

6. A pharmaceutical composition comprising a compound or pharmaceutically acceptable salt thereof according to claim 5 and a pharmaceutically acceptable carrier.

7. A method for treating hypoglycemia, comprising administering to a subject in need thereof an effective amount of a compound or pharmaceutically acceptable salt thereof according to claim 5.

8. A method for treating diabetes, diabetic peripheral neuropathy, diabetic nephropathy, diabetic retinopathy, diabetic macroangiopathy, impaired glucose tolerance or adiposis, which comprises administering to a subject in need thereof an effective amount of a compound or pharmaceutically acceptable salt thereof according to claim 5.

9. The compound or pharmaceutically acceptable salt thereof according to claim 1, wherein in general formula (I), —Z— represents —CH$_2$— or —CR$^6$R$^7$— wherein R$^6$ and R$^7$ may be the same or different from each other and they independently represent a hydrogen atom, a halogen atom, a hydroxyl group, an alkyl group, a mercapto group, an alkoxyl group, an alkylthio group, an alkylsulfonyl group, an acyl group, an acyloxyl group, an amino group, an alkylamino group, a carboxyl group, an alkoxycarbonyl group, a carbamoyl group, a nitro group, a cyano group or a trifluoromethyl group.

10. A pharmaceutical composition comprising a compound or pharmaceutically acceptable salt thereof according to claim 9 and a pharmaceutically acceptable carrier.

11. A method for treating hypoglycemia, comprising administering to a subject in need thereof an effective amount of a compound or pharmaceutically acceptable salt thereof according to claim 9.

12. A method for treating diabetes, diabetic peripheral neuropathy, diabetic nephropathy, diabetic retinopathy, diabetic macroangiopathy, impaired glucose tolerance or adiposis, which comprises administering to a subject in need thereof an effective amount of a compound or pharmaceutically acceptable salt thereof according to claim 9.

13. The compound or pharmaceutically acceptable salt thereof according to claim 9, wherein —Y— is —NR$^5$—, wherein R$^5$ represents an acyl group having 1 to 7 carbon atoms which may have a substituent selected from the group consisting of halogen atoms, lower alkyloxy groups, hydroxy group, furyl group, thienyl group, oxazolyl group, isoxazolyl group, thiazolyl group, pyridyl group, pyrimidyl group and imidazolyl group.

14. A pharmaceutical composition comprising a compound or pharmaceutically acceptable salt thereof according to claim 13 and a pharmaceutically acceptable carrier.

15. A method for treating hypoglycemia, comprising administering to a subject in need thereof an effective amount of a compound or pharmaceutically acceptable salt thereof according to claim 13.

16. A method for treating diabetes, diabetic peripheral neuropathy, diabetic nephropathy, diabetic retinopathy, diabetic macroangiopathy, impaired glucose tolerance or adiposis, which comprises administering to a subject in need thereof an effective amount of a compound or pharmaceutically acceptable salt thereof according to claim 13.

17. The compound or pharmaceutically acceptable salt thereof according to claim 9, wherein in general formula (I), B represents a cyclohexane ring which may have a substituent(s).

18. A pharmaceutical composition comprising a compound or pharmaceutically acceptable salt thereof according to claim 17 and a pharmaceutically acceptable carrier.

19. A method for treating hypoglycemia, comprising administering to a subject in need thereof an effective amount of a compound or pharmaceutically acceptable salt thereof according to claim 17.

20. A method for treating diabetes, diabetic peripheral neuropathy, diabetic nephropathy, diabetic retinopathy, diabetic macroangiopathy, impaired glucose tolerance or adiposis, which comprises administering to a subject in need thereof an effective amount of a compound or pharmaceutically acceptable salt thereof according to claim 17.

21. The compound or pharmaceutically acceptable salt thereof according to claim 17, wherein in general formula (I), A represents a benzene ring.

22. A pharmaceutical composition comprising a compound or pharmaceutically acceptable salt thereof according to claim 21 and a pharmaceutically acceptable carrier.

23. A method for treating hypoglycemia, comprising administering to a subject in need thereof an effective amount of a compound or pharmaceutically acceptable salt thereof according to claim 21.

24. A method for treating diabetes, diabetic peripheral neuropathy, diabetic nephropathy, diabetic retinopathy, diabetic macroangiopathy, impaired glucose tolerance or adiposis, which comprises administering to a subject in need thereof an effective amount of a compound or pharmaceutically acceptable salt thereof according to claim 21.

25. The compound or pharmaceutically acceptable salt thereof according to claim 21, wherein the absolute configuration of carbon atoms at a, b and c in general formula (I) is R or S independently from each other.

26. A pharmaceutical composition comprising a compound or pharmaceutically acceptable salt thereof according to claim 25 and a pharmaceutically acceptable carrier.

27. A method for treating hypoglycemia, comprising administering to a subject in need thereof an effective amount of a compound or pharmaceutically acceptable salt thereof according to claim 25.

28. A method for treating diabetes, diabetic peripheral neuropathy, diabetic nephropathy, diabetic retinopathy, diabetic macroangiopathy, impaired glucose tolerance or adiposis, which comprises administering to a subject in need thereof an effective amount of a compound or pharmaceutically acceptable salt thereof according to claim 25.

29. The compound or pharmaceutically acceptable salt thereof according to claim 25, wherein the absolute configuration of carbon atoms at both a and b in general formula (I) is R and the absolute configuration of carbon atom at c is R or S.

30. A pharmaceutical composition comprising a compound or pharmaceutically acceptable salt thereof according to claim 29 and a pharmaceutically acceptable carrier.

31. A method for treating hypoglycemia, comprising administering to a subject in need thereof an effective amount of a compound or pharmaceutically acceptable salt thereof according to claim 29.

32. A method for treating diabetes, diabetic peripheral neuropathy, diabetic nephropathy, diabetic retinopathy, diabetic macroangiopathy, impaired glucose tolerance or adiposis, which comprises administering to a subject in need thereof an effective amount of a compound or pharmaceutically acceptable salt thereof according to claim 29.

33. The compound or pharmaceutically acceptable salt thereof according to claim 25, wherein the absolute configuration of carbon atoms at both a and b in general formula (I) is S and the absolute configuration of carbon atoms in c is R or S.

34. A pharmaceutical composition comprising a compound or pharmaceutically acceptable salt thereof according to claim 33 and a pharmaceutically acceptable carrier.

35. A method for treating hypoglycemia, comprising administering to a subject in need thereof an effective amount of a compound or pharmaceutically acceptable salt thereof according to claim 33.

36. A method for treating diabetes, diabetic peripheral neuropathy, diabetic nephropathy, diabetic retinopathy, diabetic macroangiopathy, impaired glucose tolerance or adiposis, which comprises administering to a subject in need thereof an effective amount of a compound or pharmaceutically acceptable salt thereof according to claim 33.

* * * * *